US007951595B2

(12) United States Patent
Moriyama et al.

(10) Patent No.: US 7,951,595 B2
(45) Date of Patent: May 31, 2011

(54) METHODS FOR SCREENING MODULATORS OF SLC17-TYPE ANION TRANSPORT ACTIVITY

(75) Inventors: Yoshinori Moriyama, Okayama (JP); Hiroshi Omote, Okayama (JP); Keisuke Sawada, Okayama (JP)

(73) Assignee: National University Corporation Okayama University, Okayama-shi (JP)

( * ) Notice: Subject to any disclaimer, the term of this patent is extended or adjusted under 35 U.S.C. 154(b) by 0 days.

(21) Appl. No.: 12/594,149

(22) PCT Filed: Mar. 4, 2008

(86) PCT No.: PCT/JP2008/053878
§ 371 (c)(1),
(2), (4) Date: Feb. 12, 2010

(87) PCT Pub. No.: WO2008/126517
PCT Pub. Date: Oct. 23, 2008

(65) Prior Publication Data
US 2010/0167411 A1    Jul. 1, 2010

(30) Foreign Application Priority Data

Mar. 30, 2007  (JP) ................................. 2007-095055

(51) Int. Cl.
| | | |
|---|---|---|
| C12N 15/88 | (2006.01) | |
| G01N 33/53 | (2006.01) | |
| G01N 33/567 | (2006.01) | |
| C07K 1/00 | (2006.01) | |
| C07K 14/00 | (2006.01) | |
| C07K 17/00 | (2006.01) | |
| C07H 21/04 | (2006.01) | |

(52) U.S. Cl. ......... 435/458; 435/7.1; 530/350; 536/23.5
(58) Field of Classification Search ........................ None
See application file for complete search history.

(56) References Cited

U.S. PATENT DOCUMENTS

| 6,420,544 | B1 * | 7/2002 | Ellens et al. ................. 536/23.5 |
| 6,972,187 | B2 * | 12/2005 | Curtis et al. ................. 435/69.1 |
| 2002/0082405 | A1 * | 6/2002 | Donoho et al. ............. 536/23.2 |

FOREIGN PATENT DOCUMENTS

| WO | WO 01/66744 A2 | 9/2001 |
| WO | WO 01/75164 A2 | 10/2001 |

OTHER PUBLICATIONS

Elbashir et al., "Duplexes of 21-nucleotide RNAs mediate RNA interference in cultured mammalian cells," Nature 411: 494-498, May 24, 2001.
Elbashir et al., "RNA interference is mediated by 21- and 22-nucleotide RNAs," Genes & Development 15: 188-200, 2001.
Juge et al., "Vesicular Glutamate Transporter Contains Two Independent Transport Machineries," Journal of Biological Chemistry 281(51): 39499-39506, Dec. 22, 2006.
Moriyama, Y., "Membrane Energization by Proton Pumps Is Important for Compartmentalization of Drugs and Toxins: A New Type of Active Transport," The Journal of Experimental Biology 199: 1447-1454, 1996.
Sakata et al., "Cloning of a lymphatic peptide/histidine transporter," Biochem J 356: 53-60, 2001.
Bankston, Laurie A., et al., "Characterization of ATP Transport into Chromaffin Granule Ghosts. Synergy of ATP and Serotonin Accumulation in Chromaffin Granule Ghosts," The Journal of Biological Chemistry 271(29):17132-17138, Jul. 19, 1996.
Moriyama, Yoshinori et al., "Purification and Properties of a Vanadate- and N-Ethylmaleimide-Sensitive ATPase from Chromaffin Granule Membranes," The Journal of Biological Chemistry 263(17):8521-8527, Jun. 15, 1988.
Moriyama, Yoshinori et al., "One-step Purification of Escherichia coli H(+)-ATPase ($F_0F_1$) and Its Reconstitution into Liposomes with Neurotransmitter Transporters," The Journal of Biological Chemistry 266(33):22141-22146, Nov. 25, 1991.
Moriyama, Yoshinori et al., "Vesicular L-Glutamate Transporter in Microvesicles from Bovine Pineal Glands. Driving Force, Mechanism of Chloride Anion Activation, and Substrate Specificity," The Journal of Biological Chemistry 270(38):22314-22320, Sep. 22, 1995.
Nelson, Nathan et al., "Chromaffin Granule Proton Pump," Methods in Enzymology 157:619-633, 1988.

* cited by examiner

Primary Examiner — Robert Landsman
(74) Attorney, Agent, or Firm — Seed IP Law Group PLLC

(57) ABSTRACT

It is an object of the invention to isolate a transporter responsible for ATP transport and a gene encoding the transporter. It is another object of the invention to provide a method for the screening of a medicament for treating and/or regulating pain in central nerves, blood coagulation by platelet-derived ATP, or the like, the method employing such a transporter. According to the invention, a transporter responsible for ATP transport and a gene encoding the transporter were isolated. Furthermore, there is provided a method for the screening of a medicament for treating and/or regulating pain in central nerves, blood coagulation by platelet-derived ATP, or the like, the method employing such a transporter.

5 Claims, 22 Drawing Sheets

SLC17 family

| Human gene name | Protein name | Predominant substrate | Tissue distribution |
| --- | --- | --- | --- |
| SLC17A1 | NPT1 | phosphate chloride | kidney, liver |
| SLC17A2 | NPT3 | unknown | heart, muscle, brain, lung placenta, liver, kidney |
| SLC17A3 | NPT4 | unknown | liver, kidney, testis small intestine |
| SLC17A4 | NPT homologue | unknown | small intestine, liver pancreas |
| SLC17A5 | Sialin | sialic acid | heart, brain, liver, lung pancreas, placenta |
| SLC17A6 | VGLUT2 | glutamate | brain, endocrine |
| SLC17A7 | VGLUT1 | glutamate | brain, endocrine |
| SLC17A8 | VGLUT3 | glutamate | brain, liver, kidney |
| SLC17A9 | | unknown | unknown ← The present Invention |

Fig. 2

```
         10         20         30         40         50         60         70         80         90
atgaccctga caagcaggcg ccaggacagt caggaggcca ggcccgagtg ccaggcatgg acggggacgc tgctgctggg cacgtgcctt 100        110        120        130        140        150        160        170        180
ctgtactgcg cccgctccag catgcccatc tgcaccgtct ccatgagcca ggacttcggc tggaacaaga aggaggccgg catcgtgctc 190        200        210        220        230        240        250        260        270
agcagcttct tctggggcta ctgcctgaca caggttgtgg gcggccacct cggggatcgg attgggggtg agaaggtcat cctgctgtca 280        290        300        310        320        330        340        350        360
gcctctgcct ggggctccat cacggccgtc accccactgc tcgcccacct gagcagtgcc cacctggcct tcatgacctt ctcacgcatc 370        380        390        400        410        420        430        440        450
ctcatgggct tgctccaagg ggtttacttc cctgccctga ccagcctgct gtcgcagaag gtgcgggaga gtgagcgagc cttcacctac 460        470        480        490        500        510        520        530        540
agcatcgtgg gcgccggctc ccagtttggg acgctgctga ccggggcggt gggctccctg ctcctggaat ggtacggctg gcagagcatc 550        560        570        580        590        600        610        620        630
ttctatttct ccggcggcct caccttgctt tgggtgtggt acgtgtacag gtacctgctg agtgaaaaag atctcatcct ggccttgggt 640        650        660        670        680        690        700        710        720
gtcctggccc aaagccggcc ggtgtccagg cacagcagag tccctggag acggctcttc cggaagcctg ctgtctgggc agccgtcgtc 730        740        750        760        770        780        790        800        810
tcccagctct ctgcagcctg ctccttcttc atcctcctct cctggctgcc caccttcttc gaggagacct tccccgacgc caagggctgg 820        830        840        850        860        870        880        890        900
atcttcaacg tggttccttg gttggtggcg attccggcca gtctattcag cgggtttctc tctgatcatc tcatcaatca gggttacaga 910        920        930        940        950        960        970        980        990
gccatcacgg tgcggaagct catgcagggc atgggccttg gcctctccag cgtcttttgct ctgtgcctgg ccacacctc cagcttctgt 1000       1010       1020       1030       1040       1050       1060       1070       1080
gagtctgtgg tctttgcatc agcctccatc ggcctccaga ccttcaacca cagtggcatt tctgttaaca tccaggactt ggccccgtcc 1090       1100       1110       1120       1130       1140       1150       1160       1170
tgcgccggct ttctgtttgg tgtggccaac acagccgggg ccttggcagg tgtcgtgggt gtgtgtctag gcggctactt gatggagacc 1180       1190       1200       1210       1220       1230       1240       1250       1260
acgggctcct ggacttgcct gttcaacctt gtggccatca tcagcaacct ggggctgtgc accttcctgg tgtttggaca ggctcagagg 1270       1280       1290       1300       1310       1320       1330       1340       1350
gtggacctga gctctaccca tgaggacctc tag
```

Fig. 4

Primary amino acid sequence of human SLC17A9

```
1
MTLTSRRQDS QEARPECQAW TGTLLLGTCL LYCARSSMPI CTVSMSQDFG WNKKEAGIVL SSFFWGYCLT
                       TMD1                                        TMD2
71
QVVGGHLGDR IGGEKVILLS ASAWGSITAV TPLLAHLSSA HLAFMTFSRI LMGLLQGVYF PALTSLLSQK
              TMD3                              TMD4
141
VRESERAFTY SIVGAGSQFG TLLTGAVGSL LLEWYGWQSI FYFSGGLTLL WVWYVYRYLL SEKDLILALG
                TMD5                 TMD6
211
VLAQSRPVSR HSRVPWRRLF RKPAVWAAVV SQLSAACSFF ILLSWLPTFF EETFPDAKGW IFNVVPWLVA
                           TMD7                                      TMD8
281
IPASLFSGFL SDHLINQGYR AITVRKLMQG MGLGLSSVFA LCLGHTSSFC ESVVFASASI GLQTFNHSGI
                              TMD9                        TMD10
351
SVNIQDLAPS CAGFLFGVAN TAGALAGVVG VCLGGYLMET TGSWTCLFNL VAIISNLGLC TFLVFGQAQR
              TMD11                             TMD12
421
VDLSSTHEDL
```

Fig. 5

| Homo sapiens | 1 | ------------------------------------------------------------ | |
| Mus musculus | 1 | ------------------------------------------------------------ | |
| Rattus norvegicus | 1 | ------------------------------------------------------------ | |
| Bos Taurus | 1 | ------------------------------------------------------------ | |
| Canis familiaris | 1 | MQVTLRSFGHRKEQSFLFKGTFRLWLFGEVRSPAPLRLGLQGSPVGCGGHPAPTSEAHAPVNAQRGSRGSPCQVQTGYQRFEWAWGTRLRLQGPGSSARL | 100 |

| Homo sapiens | 1 | ------------------------------------------------------------ | |
| Mus musculus | 1 | ------------------------------------------------------------ | |
| Rattus norvegicus | 1 | ------MPSQRSSLMQPIPEETRKTPSAAAEEDKRWSRYPDCPEVPPAEPTPRPECQLWTGMLLLGTLLLGTLLLYCARVSMPVCAASMSQDFGWNKKEAGIV | 91 |
| Bos Taurus | 1 | ------------------MQPIPEETRKTPSAAAEEDTRWSR--------------------------------------------------------- | 26 |
| Canis familiaris | 101 | HLVHRVPVSWSTGSPPPQLTALTSHQVLPPPLFQGPHASFLASACSSQESPDMDRPECQVWTGTLLLGTLLLGTLLLYCARVSMPVCTVSMSQDFGWNKKEAGIV | 200 |

(Figure continues with multiple alignment blocks showing sequences from Homo sapiens, Mus musculus, Rattus norvegicus, Bos Taurus, and Canis familiaris)

| Homo sapiens | 260 | FEETFPDAKGHWTFNVVPWLVAIPASLFSGFLSDHLINQGYRAITVRKLMQGMGLGLSSVFALCLGHTSSFCESVVFASASIGLQTFNHSGISVNIQDLAP | 359 |
| Mus musculus | 269 | FKETFPNSKGWVFNVVPWMLAIPASLFSGFISDRLISQGYRVITVRKFMQVMGLGLSSFALCLGHTSFLKAMIFASASIGFQTFNHSGISVNIQDLAP | 368 |
| Rattus norvegicus | 292 | FKETFPHSKGWVFNVVPWLLAIPASLFSGFISDRLISQGYRVITVRKFMQVMGLGLSSIFALCLGHTTSFLKSMIFASASIGFQTFNHSGISVNIQDLAP | 391 |
| Bos Taurus | 401 | FKETFPSSKGWVFNVVPWLVAIPASLLSGLSDHLINQGYRTITVRKFMQVMGLGLSSVFALCLGHTSSFCNSVVFASASIGLQTFNHSGISVNIQDLAP | 500 |
| Canis familiaris | 285 | FQETFPSSKGWVFNVVPWLVAIPASLFSGFLSDHLINQGYRTIAVRKFMQVMGLGLSSYVFALCLGHTSSFCKSVVFASASIGLQTFNHSGISVNIQDLAP | 384 |

| Homo sapiens | 360 | SCAGFLFGVANTAGALAGVVGVCLGGYLMETTGSWTCLFNLVAIISNLGLCTFLVFGGQAQRVDLSSTHEDL | 430 |
| Mus musculus | 369 | SCAGFLFGVANTAGALAGVVGVCLSGYLIETTGSWTCVFHLVAIISNLGLGTFLVFGKAQRVDLVPTHEDL | 439 |
| Rattus norvegicus | 392 | SCAGFLFGVANTAGALAGVVGVCLGGYLIETTGSWTCVFHLVAIVSNLGLGTFLVFGKAQRVDLVPTHEDL | 462 |
| Bos Taurus | 501 | SCAGFLFGVANTAGALAGVVGVCLGGYLIETTGSWTSMFNLVAAISGLGLCTFLLFGEAQRVDLSPAHEDL | 571 |
| Canis familiaris | 385 | SCAGFLFGVANTAGALAGVVGVCLGGYLIETTGSWTSMENLVAAISGLGLCTFLLFGEAQRVDLSPTHEDL | 455 |

FIGURE 6

Mit : mitochondrion    Bar = 1 μm (A)　　　　　　　　(B)
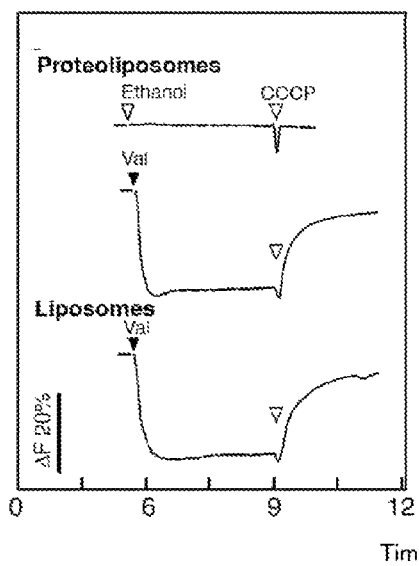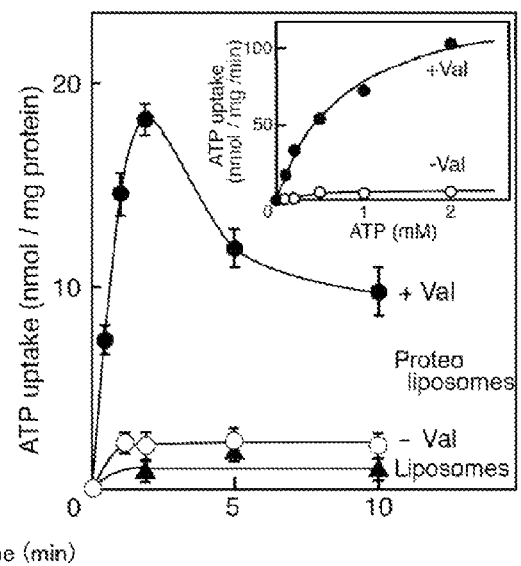
Fig.13

METHODS FOR SCREENING MODULATORS OF SLC17-TYPE ANION TRANSPORT ACTIVITY

TECHNICAL FIELD

The present invention relates to the field of a novel anion transporter. More particularly, the present invention relates to the field of an anion transporter capable of transporting a nucleotide (examples include ATP (adenosine triphosphate), GTP, UTP and ADP, but are not limited thereto). The invention also relates to the screening of a medicament capable of controlling pain or blood platelet coagulation.

BACKGROUND ART

Nucleotides such as ATP (adenosine triphosphate) and ADP (adenosine diphosphate) are chemical transmitters present in all mammalian tissues. These molecules are released from cells, and then bind to two kinds of P2 receptor families (purinergic receptors), that is, the G protein-coupled type P2Y receptor subfamily and the ion transport type P2X receptor subfamily, present in the cellular membrane of other cells, to thereby cause various important physiological actions and pathological actions. Examples of these physiological actions include pain in central nerves, blood coagulation caused by platelet-derived ATP, and the like (Non-Patent Documents 1 and 2). In order to induce the physiological actions caused by these ATP and/or ADP, ATP or ADP needs to be released (or secreted) from cells. Therefore, a medicament regulating the transport of ATP and/or ADP is thought to be useful as a medicament for treating or preventing pain in central nerves, or as a medicament capable of regulating blood coagulation caused by platelet-derived ATP.

However, although it is known that there exist a number of mechanisms for the release of ATP or ADP (Non-Patent Documents 1 and 2), many issues still remain unclear in regard to the mechanisms and the molecules involved in the mechanisms.

One of the mechanisms involves the release of ATP from endothelial cells, epithelial cells, hepatic cells or the like, due to stresses such as tension or hypotonic treatment. A second mechanism involves continual ATP secretion from osteoblasts or epithelial cells. A third mechanism is based on the regulatory exocytosis observed in nerve cells or neuroendocrine cells, glial cells or the like (FIG. 1). Exocytosis of ATP is the most important process from pharmacological and physiological aspects, but its molecular mechanism is not well known. In order for the exocytosis of ATP to occur, ATP first needs to be accumulated in the secretory vesicles. In fact, it is known that ATP is concentrated in the synaptic vesicles or dense-cored vesicles of nerves, the synaptic vesicle-like organelles (synaptic-like microvesicles) of glial cells, and the like. The process for the concentration of ATP is unclear, but it is thought that a certain active transporter is involved in the process.

The only transporter in mammals that has been confirmed so far to have ATP transport ability is the ATP/ADP exchanger (Non-Patent Documents 1 and 2). This transporter is a transporter that is present in the inner membrane of mitochondria, and exchanges the ADP present in the cytoplasm with the ATP synthesized in the mitochondria. In regard to transporters other than this, it has been recently reported that Mcd4 membrane protein and Sad p membrane protein are in charge of ATP transport in the Golgi body and the endoplasmic reticulum (Non-Patent Documents 3 to 5). Mcd4 is a kind of ATPAse, while Sad p is a transporter of the same type as the ATP/ADP exchanger. However, none of these transporters are proteins that directly participate in the exocytosis of ATP. The nature of the transporters, which transport ATP in various secretory vesicles, is still not known. Once these ATP transporters are elucidated, it will then be possible to understand the mechanism of chemical transmission involving ATP at a molecular level, and it will be also possible to artificially control the physiological phenomena and pathological phenomena in which the chemical transmission involving ATP takes part. For example, when the nature of these transporters is understood, it will be possible to search and develop a specific inhibitor by employing its transporter. Such an inhibitor is expected to be useful as a medicament for controlling pain or platelet coagulation.

Bibliographical information on the technologies of the related art, to which the invention of this application is pertained, is as follows.

[Non-Patent Document 1] Burnstock G. (2006) TIPS 27, 166-176.

[Non-Patent Document 2] Lazarowski E (2006) Purinergic signaling in neuron-glia interactions. Wiley. Chibester (Novartis Foundation Symposium 276), p. 73-90.

[Non-Patent Document 3] Mayinger P, Bankaitis V A, Meyer D I. (1995) J. Cell Biol. 131, 1377-1386.

[Non-Patent Document 4] Puglielli L, Mandon E C, Hirschberg C B. (1999) J. Biol. Chem. 274, 12665-12669.

[Non-Patent Document 5] Coco S et al. (2003) J. Biol. Chem. 278, 1354-1362.

DISCLOSURE OF THE INVENTION

Problems to be Solved by the Invention

It is an object of the present invention to isolate a transporter which takes charge of the transport of a nucleotide (examples include ATP (adenosine triphosphate), GTP, UTP and ADP, but are not limited thereto), and a gene encoding the transporter. It is another object of the present invention to provide a method for the screening of a medicament for treating and/or regulating a disease and/or condition (for example, pain in central nerves, blood coagulation caused by platelet-derived ATP, or the like), the method making use of such a transporter.

Means for Solving the Problems

The inventors of the present invention carried out cloning of an anion transporter and a functional analysis thereof by a creative method that will be described in the following Examples, and thereby completed the present invention.

The present invention provides the following.

(Item 1) An isolated and/or purified nucleic acid, selected from the group consisting of:

a nucleic acid that hybridizes under stringent conditions with a complementary strand of a nucleic acid having the nucleic acid sequence set forth in SEQ ID NO: 1, 7, 9, 11 or 13, and encodes a polypeptide having anion transport activity;

a nucleic acid that has a sequence having at least 80% homology with the nucleic acid sequence set forth in SEQ ID NO: 1, 7, 9, 11 or 13, and encodes a polypeptide having anion transport activity;

a nucleic acid that encodes a polypeptide having the amino acid sequence set forth in SEQ ID NO: 2, 8, 10, 12 or 14; and a nucleic acid that encodes a polypeptide having an amino acid sequence containing one or several amino acid modifications, substitutions, insertions or deletions relative to the amino acid sequence set forth in SEQ ID NO: 2, 8, 10, 12 or 14, and having anion transport activity.

(Item 2) The nucleic acid according to item 1, wherein the anion is a nucleotide.

(Item 3) The nucleic acid according to item 2, wherein the nucleotide is a nucleotide selected from the group consisting of ATP, GTP and ADP.

(Item 4) The nucleic acid according to item 2, wherein the nucleotide is ATP.

(Item 5) A nucleic acid having the nucleic acid sequence set forth in SEQ ID NO: 1.

(Item 6) A vector containing the nucleic acid according to item 1.

(Item 7) A cell containing the nucleic acid according to item 1.

(Item 8) A polypeptide encoded by the nucleic acid according to item 1.

(Item 9) An artificial membrane containing the polypeptide according to item 8.

(Item 10) The artificial membrane according to item 9, which is a membrane vesicle.

(Item 11) The artificial membrane according to item 9, which is a liposome.

(Item 12) An antibody that reacts specifically with the polypeptide according to item 8.

(Item 13) A method for the screening of an activity regulator of an anion transport protein, the method including:

(a) providing the artificial membrane according to item 9;

(b) contacting the artificial membrane with a candidate drug;

(c) measuring the anion transport activity of the artificial membrane; and (d) determining, from the anion transport activity measured in step (c), whether the candidate drug is an activity regulator of an anion transport protein.

(Item 14) The method according to item 13, wherein the activity regulator is an inhibitor.

(Item 15) The method according to item 13, wherein the activity regulator is an activity promoter.

(Item 16) The method according to item 13, wherein the anion transport activity is nucleotide transport activity.

(Item 17) The method according to item 16, wherein the nucleotide is a nucleotide selected from the group consisting of ATP, GTP and ADP.

(Item 18) The method according to item 13, wherein the anion transport activity is ATP transport activity.

(Item 19) An activity regulator of an anion transport protein, obtained by the method according to item 10.

(Item 20) siRNA that suppresses the expression of the nucleic acid according to item 1.

Effects of the Invention

According to the present invention, a transporter which takes charge of the transport of a nucleotide (examples include ATP (adenosine triphosphate), GTP, UTP and ADP, but are not limited thereto), and a gene encoding the transporter were isolated. Also provided herein, is a method for the screening of a medicament for treating and/or regulating pain in central nerves, blood coagulation caused by platelet-derived ATP, or the like, the method making use of such a transporter.

Furthermore, an inhibitor that suppresses the functions of the polypeptide and/or nucleic acid of the present invention is provided, and this inhibitor can provide an anti-inflammatory agent, as well as a therapeutic drug for a disease selected from the group consisting of tremor, epilepsy, Parkinson's disease, Alzheimer's disease, osteopetrosis and osteoporosis.

BRIEF DESCRIPTION OF THE DRAWINGS

FIG. 2 is a diagram showing SLC17A9 of the present invention and various known SLC17A family proteins.

FIG. 4 is a diagram showing the nucleic acid sequence of human SLC17A9 (SEQ ID NO:1).

FIG. 5 is a diagram showing the amino acid sequence of human SLC17A9(SEQ ID NO:2).

FIG. 6 is a diagram showing an alignment of the amino acid sequences of SLC17A9 derived from various species of organisms *Homo sapiens*: SEQ ID NO:2; *Mus musculus*: SEQ ID NO:8; *Rattus norvegicus*: SEQ ID NO:10;*Bos taurus*:SEQ ID NO:12; *Canis familiaris*:SEQ ID NO:14.

FIG. 13(A) is a diagram showing that a difference in the membrane potential is formed in a reconstituted liposome by adding valinomycin, which is a $K^+$ ionophore, shown through the measurement of fluorescence quenching by Oxonol V.

FIG. 13(B) is a graph showing the results obtained by an observation of the uptake of radioactive ATP (100 μM) over time, using proteoliposomes reconstituted with human SLC17A9.

ordinary blood serum (pre-immune) only, (I) anti-SLCA19 antibody only, (J) anti-synaptophysin antibody only, and (K) double staining with anti-SLCA19 antibody and anti-synaptophysin antibody. The white bar represents 10 μm.

Figure 19:
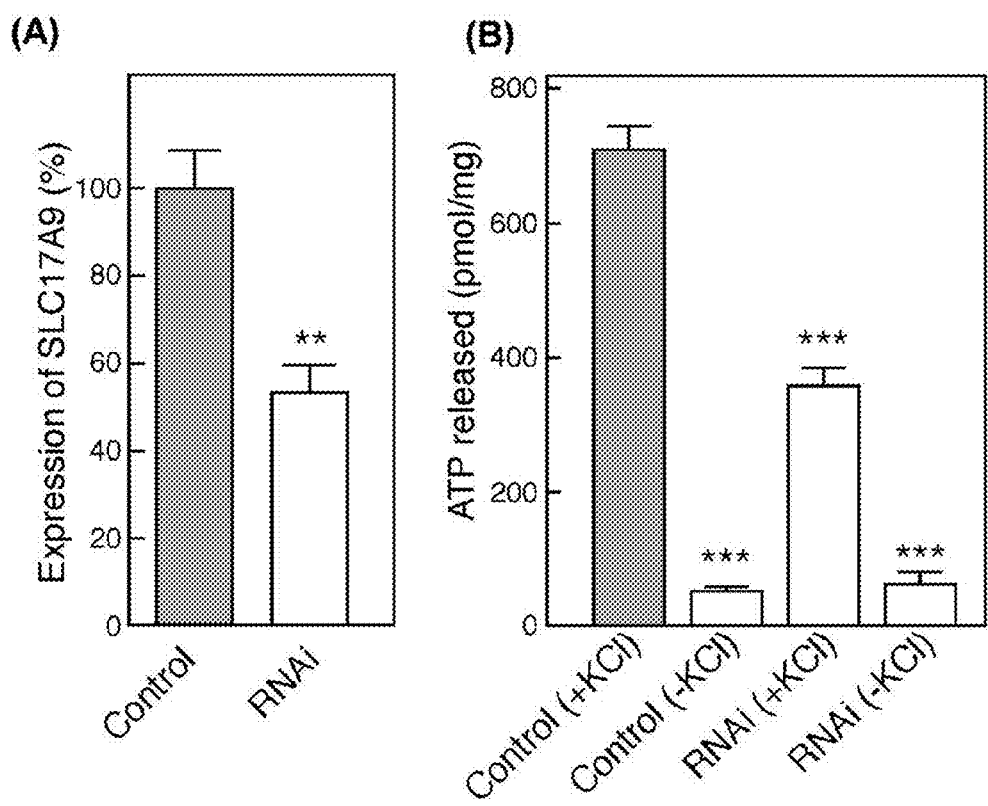

FIG. 19(A) shows the results exhibiting the effect on the expression of SLC17A9 in the case of using SLC17A9 RNAi. FIG. 19(B) shows the results exhibiting the effect on the ATP transport in the case of using RNAi.

Figure 20:
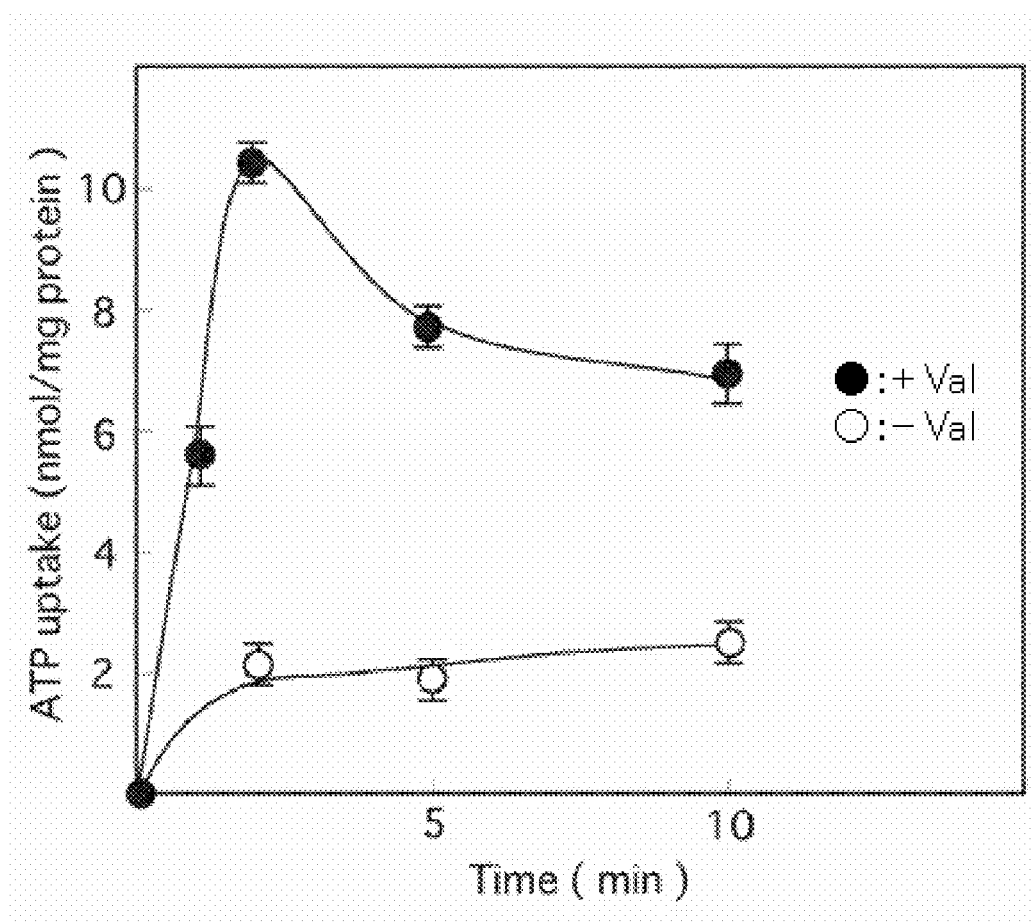

FIG. 20 is a graph showing changes over time in the ATP transport by reconstituted mSLC17A9 protein. The horizontal axis represents time (minutes), and the vertical axis represents the amount of ATP uptake (nmol/mg of protein). Filled circles (●) represent the results obtained with the addition of valinomycin, and open circles (○) represent the results obtained without the addition of valinomycin.

Figure 21:
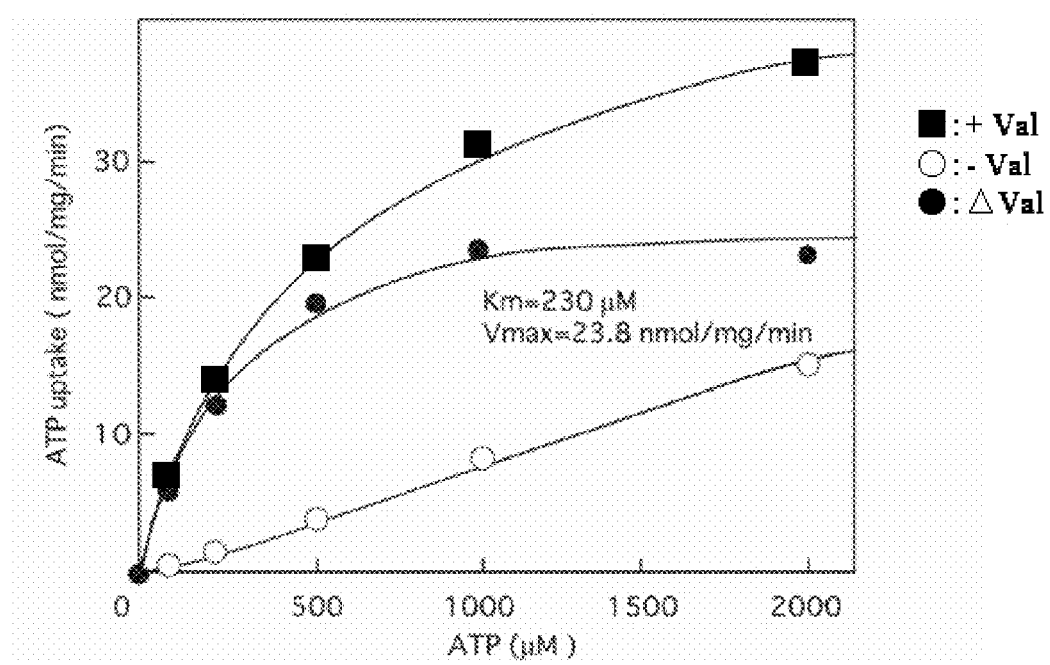

FIG. 21 shows the kinetics of the ATP transport by reconstituted mSLC17A9 protein. Filled squares (■) represent the amount of ATP uptake obtained with the addition of valinomycin; open circles (○) represent the amount of ATP uptake obtained without the addition of valinomycin; and filled circles (●) represent their differences, that is, the ATP concentration-dependency of the membrane potential-dependent transport. The horizontal axis represents the amount of ATP (μM), and the vertical axis represents the rate of ATP uptake (nmol/mg of protein/minute).

Figure 22:
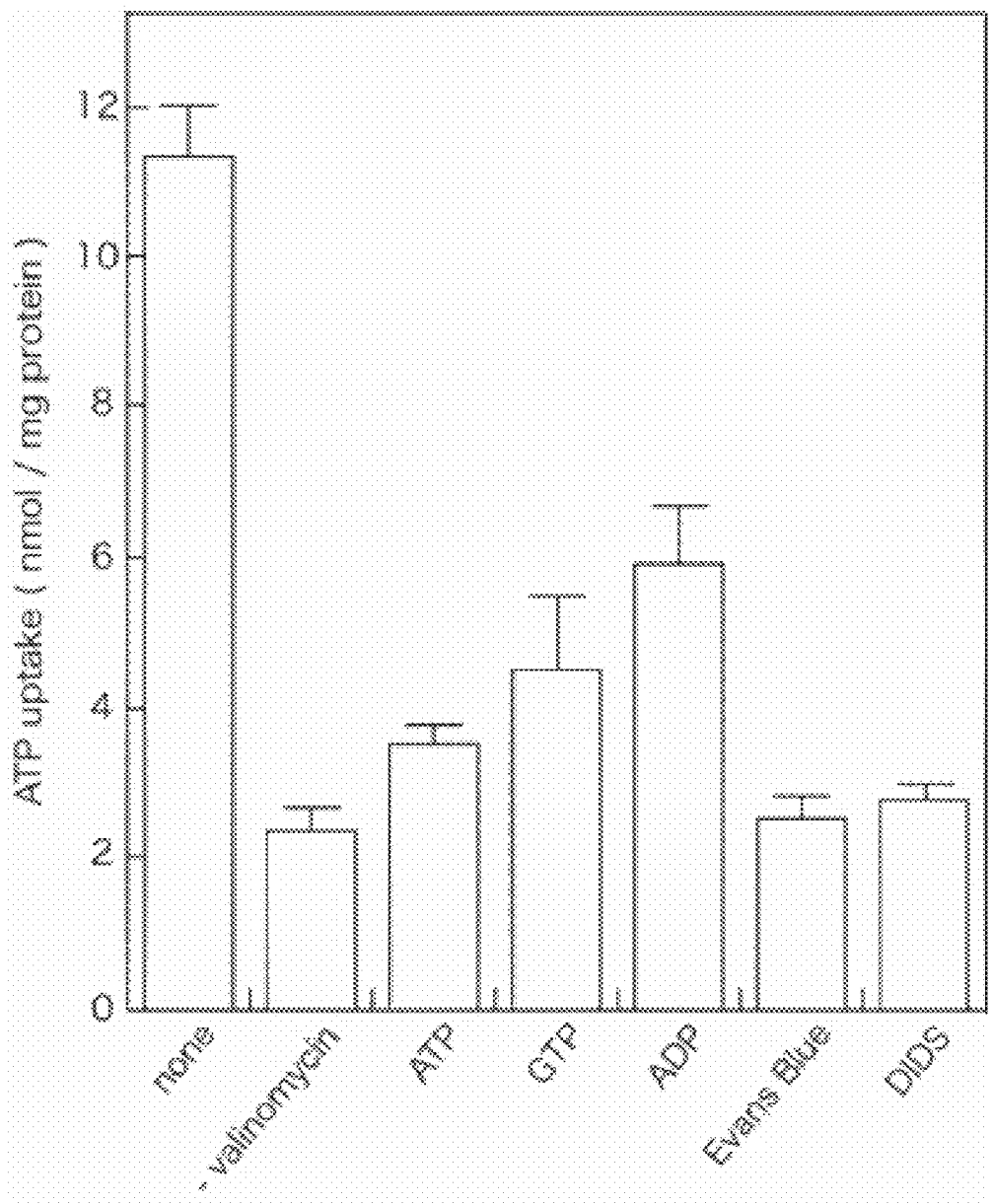

FIG. 22 is a graph showing the results of an experiment on the inhibition of ATP transport by reconstituted mSLC17A9 protein. The vertical axis represents the amount of ATP uptake (nmol/mg of protein). The amounts of the added inhibitors are ATP (2 mM), GTP (2 mM), ADP (2 mM), Evans Blue (2 μM), and DIDS (2 μM).

SEQUENCE LISTING FREE TEXT

SEQ ID NO: 1 is the nucleic acid sequence of human SLC17A9.
SEQ ID NO: 2 is the amino acid sequence of human SLC17A9.
SEQ ID NO: 3 is the sequence of a forward primer used in the cloning of human SLC17A9 gene.
SEQ ID NO: 4 is the sequence of a reverse primer used in the cloning of human SLC17A9 gene.
SEQ ID NO: 5 is the amino-terminal sequence of human SLC17A9 used in the production of anti-human SLC17A9 antibody.
SEQ ID NO: 6 is the amino-terminal sequence of mouse SLC17A9 used in the production of anti-mouse SLC17A9.
SEQ ID NO: 7 is the nucleic acid sequence of mouse SLC17A9.
SEQ ID NO: 8 is the amino acid sequence of mouse SLC17A9.
SEQ ID NO: 9 is the nucleic acid sequence of rat SLC17A9.
SEQ ID NO: 10 is the amino acid sequence of rat SLC17A9.
SEQ ID NO: 11 is the nucleic acid sequence of bovine SLC17A9.
SEQ ID NO: 12 is the amino acid sequence of bovine SLC17A9.
SEQ ID NO: 13 is the nucleic acid sequence of dog SLC17A9.
SEQ ID NO: 14 is the amino acid sequence of dog SLC17A9.
SEQ ID NO: 15 is the RNA sequence used for the knockdown in Example 18.
SEQ ID NO: 16 is the primer sequence used in the cloning of mouse SLC17A9 in Example 19.
SEQ ID NO: 17 is the primer sequence used in the cloning of mouse SLC17A9 in Example 19.

BEST MODE FOR CARRYING OUT THE INVENTION

Hereinafter, the present invention will be described. Throughout the specification, it should be understood that unless particularly stated otherwise, an expression in its singular form also includes the conception of plurality. It should be understood that unless particularly stated otherwise, the terms used in the specification are used to have the meanings that are conventionally used in the art. Therefore, unless defined otherwise, all technical and scientific terms used in the present specification have the same meanings as commonly understood by those having ordinary skill in the art to which the present invention pertains. In the case of conflict, the present specification, including the definitions, will control.

(Definitions of Terms)

Hereinafter, the definitions of the terms that are used particularly in the present specification will be listed.

The term "transporter" as used herein means a substance which transports a substance that cannot permeate through a lipid bilayer membrane (for example, ATP), across a lipid bilayer membrane. Typically, a transporter is a membrane protein present in the lipid bilayer membrane. The transporter, which is a protein, is used interchangeably with "transport protein" in the present specification.

The term "transport activity" as used herein means an activity of transporting a substance that cannot permeate through a lipid bilayer membrane (for example, an anion such as ATP), across a lipid bilayer membrane. The transport activity concerning anions will be referred to in the present specification as "anion transport activity," and the transport activity concerning ATP will be referred to in the present specification as "ATP transport activity."

The term "proton pump" as used herein means a protein that has a transport activity of transporting $H^+$ using ATP as an energy source. Representative examples of the proton pump include, but are not limited to, $F_oF_1$-ATPase that is present in *Escherichia coli*, mitochondria and chloroplasts; V-ATPase that is present in vacuoles and chromaffin granules; and Na/K-ATPase and H/K-ATPase that are present in the cellular membrane.

The term "artificial membrane" as used herein is a membrane artificially produced using lipids as raw materials, and is preferably a lipid bilayer membrane, but is not limited thereto. An example of the "artificial membrane" may be a liposome, but is not limited thereto.

The term "activity regulator of an anion transport protein" as used herein means a substance that exerts influence on the transport activity of an anion transport protein. The "activity regulator of an anion transport protein" may be a substance that promotes the transport activity, or may be a substance that inhibits the transport activity.

When used in the present specification, a "kit" means a product that includes a plurality of vessels, and an instruction manual given by the manufacturer, while each of the vessels contains the nucleic acid and/or protein of the present invention. If necessary, the kit of the present invention includes an artificial membrane such as liposomes, or lipids for use in the production of an artificial membrane. Furthermore, if necessary, the kit of the present invention includes an ATPase (for example, $F_oF_1$-ATPase) for use in the formation of electrochemical potential of protons in the artificial membrane.

A "polynucleotide," "nucleic acid" or "nucleic acid molecule" may refer to a ribonucleotide (adenosine, guanosine, uridine or cytidine; "RNA molecule") or a deoxyribonucleotide (deoxyadenosine, deoxyguanosine, deoxythymidine or deoxycytidine ("DNA molecule") in the form of a phosphoric acid ester polymer, which is in a single strand form, a double strand form or some other form, or any phosphoester analogues thereof (for example, phosphorothioate and thioester).

A "polynucleotide sequence," "nucleic acid sequence" or "nucleotide sequence" is a series of nucleotide bases (also referred to as "nucleosides") present in a nucleic acid (for example, DNA or RNA), and means any strand of two or more nucleotides or a complementary strand thereof. Preferable nucleic acids of the present invention include the nucleic acid shown in any of SEQ ID NO: 1, 7, 9, 11 or 13, and a complementary strand, variants and fragments thereof.

A "complementary strand" means a strand of nucleotides that is likely to form base pairs with a certain nucleic acid sequence. For example, the respective strands of a double-stranded DNA have base sequences that are complementary to each other, and from the viewpoint of one strand, the other strand is a complementary strand.

A "coding sequence," or a sequence that "encodes" an expression product (for example, RNA, polypeptide, protein or enzyme), is a nucleotide sequence leading to the generation of the product when expressed.

A "protein," "peptide" or "polypeptide" contains a consecutive string of two or more amino acids. Preferable peptides of the present invention include the peptide shown in any of SEQ ID NO: 2, 8, 10, 12 or 14, and variants and fragments thereof.

A "protein sequence," "peptide sequence," or "polypeptide sequence" or "amino acid sequence" refers to a series of two or more amino acids present in a protein, a peptide or a polypeptide.

The "homology" of genes (for example, nucleic acid sequence, amino acid sequence, or the like) as used herein refers to the degree of identity with each other between two or more gene sequences. Furthermore, the identity of sequences (nucleic acid sequences, amino acid sequences, and the like) as used herein refers to the degree of sequences (individual nucleic acids, amino acids, and the like) being identical with each other, between two or more comparable sequences. Therefore, as the homology of two certain genes is higher, the identity or similarity of those sequences is high. Whether two kinds of genes are homologous may be investigated by directly comparing the sequences, or in the case of nucleic acids, according to a method of hybridization under stringent conditions. In the case of directly comparing two gene sequences, if the DNA sequence between those gene sequences is representatively at least 50% identical, preferably if at least 70% identical, and more preferably if at least 80%, 90%, 95%, 96%, 97%, 98% or 99% identical, those genes are homologous. In the present specification, the "similarity" of genes (for example, nucleic acid sequences, amino acid sequences, or the like) refers, with respect to the homology, to the degree of identity with each other of two or more gene sequences when conservative substitution is regarded as positive (identical). Therefore, if there is conservative substitution, homology and similarity differ from each other owing to the presence of the conservative substitution. Furthermore, if there is no conservative substitution, homology and similarity represent the same value.

In the present specification, comparison of the similarity, identity and homology of amino acid sequences and base sequences is calculated using FASTA, which is a tool for sequence analysis, and using default parameters.

In the present specification, the term "fragment" refers to a polypeptide or polynucleotide having a sequence length of 1 to n−1 units, with respect to the full length polypeptide or polynucleotide (having a length of n units). The length of the fragment may be appropriately modified according to the purpose, and for example, the lower limit of the length in the case of a polypeptide may be 3, 4, 5, 6, 7, 8, 9, 10, 15, 20, 25, 30, 40, 50 and more amino acids, while those lengths represented by integers that are not specifically listed herein (for example, 11 or the like) may also be appropriate as the lower limit. Also, in the case of a polynucleotide, the lower limit may be 5, 6, 7, 8, 9, 10, 15, 20, 25, 30, 40, 50, 75, 100 and more nucleotides, and those lengths represented by integers that are not specifically listed herein (for example, 11 or the like) may also be appropriate as the lower limit. In the present specification, the lengths of a polypeptide and a polynucleotide can be represented by the number of amino acids and the number of nucleic acids, respectively, as described above; however, such a referred number is not to be regarded as absolute, and as long as the same functions are exhibited, the referred number as the upper limit or lower limit is intended to include those having several units above or below (or, for example, 10% above or below) the referred number. In order to express such intention, in the present specification, the expression "about" may come before the number. However, in the present specification, it should be understood that the presence or absence of the expression "about" is not intended to affect the interpretation of the value. A useful length of a fragment for use in the present specification can be determined on the basis of whether at least one function among the functions of the full length protein, which serves as the reference of the fragment, is maintained.

An "isolated" biological factor (for example, nucleic acid, protein or the like) as used herein refers to a product that has been substantially separated or purified from other naturally occurring biological factors in the cells of an organism (for example, in the case of a nucleic acid, factors other than nucleic acids, and nucleic acids having nucleic acid sequences other than that of a nucleic acid of interest; in the case of a protein, factors other than proteins, and proteins having amino acid sequences other than that of a protein of interest; and the like). "Isolated" nucleic acids and proteins include nucleic acids and proteins that have been purified according to standard purification methods. Therefore, isolated nucleic acids and proteins include chemically synthesized nucleic acids and proteins.

A "purified" biological factor (for example, nucleic acid, protein or the like) as used herein refers to a product obtained by removing at least a part of factors that are naturally accompanying the biological factor. Therefore, the purity of a biological factor in regard to the biological factor in its purified state is usually higher than the purity of the biological factor in its usual state (that is, the factor is concentrated).

The terms "purified" and "isolated" as used herein imply that a biological factor of a same type is present at a proportion of preferably at least 75% by weight, more preferably at least 85% by weight, even more preferably at least 95%, and most preferably at least 98% by weight.

In the present specification, the phrase "polynucleotide that hybridizes under stringent conditions" implies the well known conditions that are conventionally used in the art. Such a polynucleotide can be obtained by using a colony hybridization method, a plaque hybridization method, a Southern blot hybridization method or the like, while using a polynucleotide selected from the polynucleotides of the present invention as a probe. Specifically, such a polynucleotide means a polynucleotide that can be identified by carrying out hybridization at 65° C. in the presence of 0.7 to 1.0 M NaCl, using a filter having a colony- or plaque-derived DNA immobilized thereon, and then washing the filter under the conditions of 65° C. using an SSC (saline-sodium citrate) solution at a 0.1- to 2-fold concentration (the composition of an SSC solution at a one-fold concentration includes 150 mM sodium chloride and 15 mM sodium citrate). Hybridization can be carried out according to methods described in experiment manuals such as Molecular Cloning $2^{nd}$ ed., Current Protocols in Molecular Biology, Supplement 1-38, and DNA Cloning 1: Core Techniques, A practical Approach, Second Edition, Oxford University Press (1995). Here, from the sequence that hybridizes under stringent conditions, preferably, a sequence which includes a sequence of A only or a sequence of T only is excluded. A "hybridizable polynucleotide" refers to a polynucleotide which can hybridize to another polynucleotide under the above-described hybridization conditions. Specific examples of the hybridizable polynucleotide include a polynucleotide having at least 60% homology with the base sequence of a DNA that encodes a polypeptide having the amino acid sequence specifically shown in the present invention, preferably such a polynucleotide having at least 80% homology, and more preferably such a polynucleotide having at least 95% homology.

The term "highly stringent conditions" as used herein refers to the conditions designed to allow hybridization of a DNA strand having high complementarity to a nucleic acid sequence, but to exclude hybridization of DNA with significant mismatch bases. The stringency of hybridization is determined mainly by the conditions of temperature, ion strength, and a denaturant such as formamide. Examples of such "highly stringent conditions" in terms of hybridization and washing may be 0.0015 M sodium chloride and 0.0015 M sodium citrate at 65 to 68° C., or 0.015 M sodium chloride, 0.0015 M sodium citrate and 50% formamide at 42° C. In regard to such highly stringent conditions, reference may be made to Sambrook et al., Molecular Cloning: A Laboratory Manual, $2^{nd}$ Edition, Cold Spring Harbor Laboratory (Cold Spring Harbor, N.Y., 1989); and Anderson et al., Nucleic Acid Hybridization: A Practical Approach, IV, IRL Press Limited (Oxford, England) Limited, Oxford, England. If necessary, more stringent conditions (for example, higher temperature, lower ion strength, more formamide, or another denaturant) may also be used. Other agents may be included in the hybridization buffer solution and washing buffer solution, for the purpose of reducing non-specific hybridization and/or background hybridization. Examples of such other agents include 0.1% bovine serum albumin, 0.1% polyvinylpyrrolidone, 0.1% sodium pyrophosphate, 0.1% sodium dodecyl sulfate ($NaDodSO_4$ or SDS), Ficoll, Denhardt solution, ultrasonication-treated salmon sperm DNA (or other non-complementary DNA), and dextran sulfate, but other appropriate agents may also be used. The concentration and form of these additives may be modified without substantially affecting the stringency of the hybridization conditions. Hybridization experiments are usually performed at pH 6.8 to 7.4, but under representative ion strength conditions, the rate of hybridization is almost pH-independent. See Anderson et al., Nucleic Acid Hybridization: A practical Approach, Chapter 4, IRL Press Limited (Oxford, England).

As factors affecting the stability of double-stranded DNA, there may be mentioned the composition of bases, length, and the degree of base pair mismatch. The conditions of hybridization may be adjusted by a person of ordinary skill in the art, and by applying these variables, it can be made possible that DNA with different sequence relatedness form hybrids. The melting temperature of a completely matched double-stranded DNA can be estimated by the following formula:

$$T_m(° C.)=81.5+16.6(\log [Na^+])+0.41(\% G+C)-600/N-0.72(\% \text{ formamide})$$

Here, N is the length of the double strand being formed; [Na+] is the molar concentration of sodium ions in the hybridization solution or washing solution; and % G+C is the percentage of (guanine+cytosine) bases in the hybrid.

In regard to an incompletely matched hybrid, the melting temperature is decreased by about 1° C. for every 1% mismatch.

The term "moderately stringent conditions" as used herein refers to the conditions in which a double-stranded DNA having a higher degree of base pair mismatch than that may occur under "highly stringent conditions," may be formed. Representative examples of the "moderately stringent conditions" may be 0.015 M sodium chloride, 0.0015 M sodium citrate at 50 to 65° C., or 0.015 M sodium chloride, 0.0015 M sodium citrate and 20% formamide at 37 to 50° C. For instance, "moderately stringent" conditions of 0.015 M sodium ions and 50° C. allow about 21% mismatch.

It will be understood by a person of ordinary skill in the art that there may be no complete distinction between the "highly" stringent conditions and the "moderately" stringent conditions in the present specification. For example, with 0.015 M sodium ions (no formamide), the melting temperature of a completely matched, long DNA is about 71° C. Under washing at 65° C. (the same ion strength), this condition allows about 6% mismatch. In order to capture more distantly related sequences, a person having ordinary skill in the art may simply lower the temperature, or may increase the ion strength.

In regard to an oligonucleotide probe having up to about 20 nucleotides, an appropriate estimation of the melting temperature at 1 M NaCl is provided by the expression: Tm=(2° C. for a single A-T base)+(4° C. for a single G-C base pair). In addition, the sodium ion concentration in 6× citric acid sodium salt (SSC) is 1 M (see Suggs, et al., Developmental Biology Using Purified Genes, page 683, edited by Brown and Fox (1981)).

A natural nucleic acid that encodes a protein such as a polypeptide having the amino acid sequence of SEQ ID NO: 2, 8, 10, 12 or 14, or a variant or fragment thereof, is easily separated from, for example, a cDNA library having a PCR primer containing a part of the nucleic acid sequence of SEQ ID NO: 1, 7, 9, 11 or 13, or a variant thereof, and a hybridization probe. The nucleic acid that encodes a polypeptide having the amino acid sequence of SEQ ID NO: 2, 8, 10, 12 or 14, or a variant or fragment thereof or the like, may be hybridized with one of the sequences shown in SEQ ID NO: 1, 7, 9, 11 or 13, or a part thereof, under less stringent conditions that are defined by a hybridization buffer solution essentially containing 1% bovine serum albumin (BSA); 500 mM sodium phosphate ($NaPO_4$); 1 mM EDTA; and 7% SDS at a temperature of 42° C., and a washing buffer solution essentially containing 2×SSC (600 mM NaCl; 60 mM sodium citrate); and 0.1% SDS at 50° C., more preferably under less stringent conditions that are defined by a hybridization buffer solution essentially containing 1% bovine serum albumin (BSA); 500 mM sodium phosphate ($NaPO_4$); 15% formamide; 1 mM EDTA; and 7% SDS at a temperature of 50° C., and a washing buffer solution essentially containing 1×SSC (300 mM NaCl; 30 mM sodium citrate); and 1% SDS at 50° C., and most preferably under less stringent conditions that are defined by a hybridization buffer solution essentially containing 1% bovine serum albumin (BSA); 200 mM sodium phosphate (NaPO₄); 15% formamide; 1 mM EDTA; and 7% SDS at a temperature of 50° C., and a washing buffer solution essentially containing 0.5×SSC (150 mM NaCl; 15 mM sodium citrate); and 0.1% SDS at 65° C.

The percentages of "identity," "homology" and "similarity" of sequences (amino acid, nucleic acid, or the like) in the present specification are determined by comparing two sequences that are optimally aligned over a comparison window. Here, the portion of the polynucleotide sequence or polypeptide sequence within the comparison window may include additions or deletions (that is, gaps), as compared with the reference sequence for the optimal alignment of the two sequences (if the other sequence includes additions, gaps may occur, but the reference sequence as used herein is defined to have neither additions nor deletions). The number of matched positions is determined by determining the number of positions where the same nucleic acid bases or amino acid residues are recognized in both of the sequences, and the number of matched positions is divided by the total number of positions in the comparison window, followed by multiplication of the obtained result by 100, to thereby calculate the percentage of identity. In the case of use in the search, the homology is evaluated using appropriate ones among those various sequence comparing algorithms and programs that are well known in the art. Examples of these algorithms and programs include TBLASTN, BLASTP, FASTA, TFASTA and CLUSTALW (Pearson and Lipman, 1988, Proc. Natl. Acad. Sci. USA, 85(8): 2444-2448; Altschul et al., 1990, J. Mol. Biol., 215(3): 403-410; Thompson et al., 1994, Nucleic Acids Res., 22(2): 4673-4680; Higgins et al., 1996, Methods Enzymol., 266: 383-402; Altschul et al., 1990, J. Mol. Biol., 215(3): 403-410; and Altschul et al., 1993, Nature Genetics, 3: 266-272), but these examples are not intended to be limiting. In a particularly preferred exemplary embodiment, the homology of protein and nucleic acid sequences is evaluated using Basic local Alignment Search Tool (BLAST) that is conventionally well known in the art (see, for example, *Karlin and Altschul,* 1990, Proc. Natl. Acad. Sci. USA, 87: 2267-2268; Altschul et al., 1990, J. Mol. Biol., 215: 403-410; Altschul et al., 1993, Nature Genetics, 3: 266-272; and Altschul et al., 1997, Nuc. Acids Res., 25: 3389-3402). Particularly, comparison or search may be achieved by performing the following operations using five customized BLAST programs.

(1) Compare an amino acid query sequence against a protein sequence database using BLASTP and BLAST3;

(2) Compare a nucleotide query sequence against a nucleotide sequence database using BLASTN;

(3) Compare a conceptual translation product obtained by converting a nucleotide query sequence (both strands) into six reading frames, against a protein sequence database using BLASTX;

(4) Compare a protein query sequence against a nucleotide sequence database converted in all six reading frames (both strands), using TBLASTN; and (5) Compare a six-reading frame conversion product of a nucleotide query sequence, against a nucleotide sequence database converted in six reading frames, using TBLASTX.

BLAST programs are designed to identify homologous sequences by specifying similar segments called "high-score segment pairs" between an amino acid query sequence or a nucleic acid query sequence, and preferably a subject sequence obtained from a protein sequence database or a nucleic acid sequence database. It will be preferable if many high-score segment pairs are identified (that is, aligned) by a scoring matrix that is well known in the art. Preferably, BLOSUM62 matrix (Gonnet et al., 1992, Science, 256: 1443-1445; and Henikoff and Henikoff, 1993, Proteins, 17: 49-61) is used as the scoring matrix. This matrix is second to none as a preferable matrix, but PAM matrix or PAM250 matrix may also be used (see, for example, Schwartz and Dayhoff, eds., 1978, Matrices for Detecting Distance Relationships: Atlas of Protein Sequence and Structure, Washington: National Biomedical Research Foundation). The BLAST programs evaluate the statistical significance of all identified high-score segment pairs, and selects a segment which satisfies the threshold level of the significance that a user uniquely sets up, preferably such as the homology ratio unique to the user. It is preferable to evaluate the statistical significance of high-score segment pairs using Karlin's formula, which determines statistical significance (see Karlin and Altschul, 1990, Proc. Natl. Acad. Sci. USA, 87: 2267-2268).

The term "primer" as used herein refers to a substance required for the initiation of a reaction of a high molecular weight compound to be synthesized, in an enzymatic reaction for high molecular weight compound synthesis. In a reaction for synthesizing a nucleic acid molecule, a nucleic acid molecule (for example, DNA, RNA or the like) which is complementary to the sequence of a part of the high molecular weight compound to be synthesized may be used.

A nucleic acid molecule that is usually used as a primer may be one such molecule having a nucleic acid sequence having a length of at least 8 contiguous nucleotides, which is complementary to the nucleic acid sequence of a gene of interest. Such a nucleic acid sequence may be a nucleic acid sequence having preferably a length of at least 9 contiguous nucleotides, more preferably a length of 10 contiguous nucleotides, even more preferably a length of 11 contiguous nucleotides, a length of 12 contiguous nucleotides, a length of 13 contiguous nucleotides, a length of 14 contiguous nucleotides, a length of 15 contiguous nucleotides, a length of 16 contiguous nucleotides, a length of 17 contiguous nucleotides, a length of 18 contiguous nucleotides, a length of 19 contiguous nucleotides, a length of 20 contiguous nucleotides, a length of 25 contiguous nucleotides, a length of 30 contiguous nucleotides, a length of 40 contiguous nucleotides, or a length of 50 contiguous nucleotides. The nucleic acid sequence used as a primer includes a nucleic acid sequence that is at least 70% homologous, more preferably at least 80% homologous, even more preferably 90% homologous, and most preferably 95% homologous, to the sequence described above. A sequence appropriate as a primer may vary depending on the nature of the sequence intended to be synthesized (amplified), but a person having ordinary skill in the art can design an adequate primer in accordance with the intended sequence. Design of such a primer is well known in the art, and may be carried out manually or using a computer program (for example, LASERGENE, PrimerSelect, or DNAStar).

In the present specification, the term "substitution, addition or deletion" of a polypeptide or a polynucleotide means that an amino acid or a substitute thereof, or a nucleotide or a substitute thereof is respectively substituted, added or removed with respect to the original polypeptide or polynucleotide. Such technologies of substitution, addition or deletion are well known in the art, and examples of such technologies include site-specific mutagenesis technologies and the like. The substitution, addition or deletion may occur at any number as long as it is one or greater, and such a number can be made large, as long as the function of interest (for example, signal transduction functions of hormone and cytokines, and the like) is maintained in a variant having the substitution, addition or deletion. For example, that number could be 1 or several, and preferably within 20% or within 10% of the full length, or 100 or smaller, 50 or smaller, 25 or smaller, or the like.

The molecular biological techniques, biochemical techniques and microbiological techniques as used herein are well known and conventionally used in the art, and are described in, for example, Sambrook J. et al., (1989). Molecular Cloning: A Laboratory Manual, Cold Spring Harbor and its $3^{rd}$ Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press; Supplement Experimental Medicine "Experimental Methods in Transfection & Expression Analysis," Yodosha, 1997; and the like, the disclosure of which is incorporated herein by reference, in part (maybe in their entirety) as related to the present specification.

The DNA synthesis technologies and nucleic acid chemistry for the production of artificially synthesized genes are described in, for example, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press; and the like, the disclosure of which is incorporated herein by reference, in part as related to the present specification.

To confirm the presence of nucleic acid in the present specification, evaluation may be made by any appropriate methods, including molecular biological measurement methods such as a radiation method, a fluorescence method, a Northern blotting method, a dot blotting method, and a PCR method.

The term "antibody" includes an antibody and fragments thereof (preferably, antigen binding fragments), but is not limited to these. This term includes a monoclonal antibody, a polyclonal antibody, a double-specific antibody, a Fab antibody fragment, a $F(ab)_2$ antibody fragment, a Fv antibody fragment (for example, $V_H$ or $V_L$), a single chain Fv antibody fragment, and a dsFv antibody fragment. Furthermore, the antibody molecules of the present invention may be a complete human antibody, a mouse antibody, a rat antibody, a rabbit antibody, a goat antibody, a chicken antibody, a humanized antibody, or a chimeric antibody. The antibodies of the present invention react specifically to a polypeptide having the amino acid sequence of SEQ ID NO: 2, 8, 10, 12 or 14.

A gene of the present invention can have its expression knocked down (suppressed) using a siRNA. The methods for producing a siRNA from a predetermined gene are well known, and for example, annealed synthetic double-stranded siRNAs are available from siRNA suppliers that are known in the art (for example, Nippon EGT Co., Ltd., Toyama, Japan). Such a synthetic siRNA is dissolved in an RNAse-free solution, and the solution is adjusted to a final concentration of 20 µM, and then is introduced into cells. In the case of producing a siRNA, for example, conditions such as that: (1) there are no 4 or more contiguous G or C bases, (2) there are no 4 or more contiguous A or T bases, or (3) there are no 9 or more G or C bases, may also be added. The siRNA of the present invention is 19 bases long, 20 bases long, 21 bases long, 22 bases long, 23 bases long, 24 bases long, 25 bases long, 26 bases long, 27 bases long, 28 bases long, 29 bases long or 30 bases long. The siRNA of the present invention preferably has a length of 19 bases. The siRNA of the present invention also preferably has a length of 20 bases. The siRNA of the present invention also preferably has a length of 21 bases. The siRNA of the present invention also preferably has a length of 22 bases. The siRNA of the present invention also preferably has a length of 23 bases. The siRNA of the present invention also preferably has a length of 24 bases.

The terms "expresses" and "expression" mean enabling or causing the information in a gene, an RNA sequence or a DNA sequence to be made known (for example, producing a protein by activating cellular functions that participate in the transcription and translation of the corresponding gene). A DNA sequence is expressed so as to form an "expression product" (for example, an RNA (for example, mRNA) or a protein) within a cell or under the action of a cell. The expression product itself may be said to be "expressed" by the cell.

The term "transformation" means introducing a nucleic acid into a cell. The gene or sequence to be introduced may be called a "clone." The host cell receiving the introduced DNA or RNA is "transformed," and this is a "transformant" or a "clone." The DNA or RNA that is introduced into a host cell may be derived from any source, and may be derived from a cell of the same genus or species as the host cell, or derived from a cell of a different genus or species.

The term "vector" includes a medium (for example, a plasmid) which allows a DNA sequence or an RNA sequence to be introduced into a host cell, so that the medium transforms the host, and if necessary, promotes expression and/or replication of the introduced sequence.

Examples of the vector that may be used in the present invention include plasmids, viruses, bacteriophages, integratable DNA fragments, and other vehicles which can promote the integration of nucleic acid into the genome of the host. Plasmids are vectors of the most generally used form and all of which that provide equivalent functions or are known or are becoming known in the art, are appropriate for use in the present specification. See, for example, Pouwels, et al., Cloning Vectors: A Laboratory Manual, 1985, and Supplements, Elsevier, N.Y., and Rodriguez, et al. (Ed), Vectors: A Survey of Molecular Cloning Vectors and Their Uses, 1988, Buttersworth, Boston, Mass.

The term "expression system" means a host cell and a compatible vector, which can express a protein or nucleic acid that is carried by the vector and introduced into the host cell under appropriate conditions. Common expression systems include E. coli host cells and plasmid vectors, insect host cells and baculovirus vectors, and mammalian host cells and vectors.

Expression of a nucleic acid that encodes the polypeptide set forth in SEQ ID NO: 2, 8, 10, 12 or 14 of the present invention may be carried out, preferably in eukaryotic cells, according to a conventional method. As for host cells that are appropriate for the expression of nucleic acid, higher eukaryotes may be mentioned, such host cells include established tissue culture cell lines derived from animal cells (animal cells of both non-mammalian origin (for example, insect cells) and mammalian origin (for example, human, primates and rodents cells)).

Higher eukaryotic tissue culture cells may also be used for the recombinant production of the polypeptide set forth in SEQ ID NO: 2, 8, 10, 12 or 14 of the present invention. Any higher eukaryotic tissue culture cell lines (insect baculovirus expression systems may be mentioned) may be used, but mammalian cells are preferable. Transformation, transfection and proliferation of such cells constitute a conventional procedure. Examples of useful cell lines include HeLa cells, Chinese hamster ovary (CHO) cell lines, J774 cells, Caco2 cells, baby rat kidney (BRK) cell lines, insect cell lines, avian cell lines, and monkey (COS) cell lines. An expression vector for such cell lines usually contains an origin of replication, a promoter, a translation initiation site, RNA splice sites (if genomic DNA is used), a polyadenylation site, and a transcription termination site. Such a vector also usually contains a selection gene or an amplification gene. A suitable expression vector may be a plasmid, virus or retrovirus that carries a promoter derived from a source such as, for example, adenovirus, SV40, parvovirus, vaccinia virus or cytomegalovirus. Examples of the expression vector include pCR (registered trademark) 3.1, pcDNA1, pCD (Okayama, et al., Mol. Cell. Biol. 5: 1136), pMC1 neo Poly-A (Thomas, et al., (1987) Cell 51: 503), pREP8, pSVSPORT, derivatives thereof, and baculovirus vectors (for example, pAC373 or pAC610).

The present invention also includes a fusion product containing the polypeptide set forth in SEQ ID NO: 2, 8, 10, 12 or 14 and the polynucleotide set forth in SEQ ID NO: 1, 7, 9, 11 or 13 of the present invention, and a second polypeptide moiety or a second polynucleotide moiety (may be referred to as a "tag"). A fusion polypeptide of the present invention may be conveniently constructed by, for example, inserting the polynucleotide of the present invention or a fragment thereof into an expression vector. The fusion product of the present invention may contain a tag that facilitates purification or detection. Examples of such a tag include glutathione-S-transferase (GST), hexahistidine (His6) tags, maltose binding protein (MBP) tags, hemagglutinin (HA) tags, cellulose binding protein (CBP) tags, and myc tags. Detectable tags (for example, $^{32}$P, $^{35}$S, $^{3}$H, $^{99m}$Tc, $^{123}$I, $^{111}$In, $^{68}$Ga, $^{18}$F, $^{125}$I, $^{131}$I, $^{113m}$In, $^{76}$Br, $^{67}$Ga, $^{99m}$Tc, $^{123}$I, $^{111}$In and $^{68}$Ga) may also be used to label the polypeptide and the polynucleotide of the present invention. Methods for constructing and using such fusion products are well known in the art.

The term "operably linked" as used herein implies that a sequence of interest is located such that expression (operation) thereof is under the control of a certain transcription/translation regulatory sequence (for example, a promoter, an enhancer or the like) or translation regulatory sequence. In order for a promoter to be operably linked to a gene, the promoter is usually located immediately upstream to the gene, but is not necessarily located adjacently.

Any technology may be used herein for the introduction of a nucleic acid molecule into cells, and examples include transformation, transduction, transfection and the like. Such technologies for the introduction of nucleic acid molecules are well known and commonly used in the art, and are described in, for example, edited by Ausubel F. A. et al., (1998), Current Protocols in Molecular Biology, Wiley, New York, N.Y.; Sambrook J, et al. (1987) Molecular Cloning: A Laboratory Manual, $2^{nd}$ Ed. and $3^{rd}$ Ed., Cold Spring Harbor Laboratory Press, Cold Spring Harbor, N.Y.; Supplement Experimental Medicine "Experimental Methods in Transfection & Expression Analysis," Yodosha, 1997; and the like. Introduction of genes can be confirmed by using the methods described in the present specification, such as Northern blot analysis and Western blot analysis, or other well-known, commonly used technologies.

As for the method of introducing a vector, any of the above-described methods for introducing DNA into cells can be used, and for example, transfection, transduction, transformation, and the like (for example, a calcium phosphate method, a liposome method, a DEAE dextran method, an electroporation method, a method using a particle gun (gene gun), and the like) may be used.

(Method for the Screening of Activity Regulator of Anion Transport Protein)

It is possible to perform screening of an activity regulator of an anion transport protein, according to various methods using the protein of the present invention. For example, it is possible to perform screening of an activity regulator of an anion transport protein by:

(a) reconstituting ATPase (for example, vacuolar ATPase) and the membrane protein of the present invention into liposomes, (b) adding (1) radiolabeled ATP only, and (2) radiolabeled ATP and a candidate agent, respectively, to the liposomes, and incubating the liposomes, (c) precipitating the liposomes through centrifugation, and comparing the amount of radiolabeled ATP taken up into the liposomes in the instance of (1) and the same amount in the instance of (2), and (d) determining whether the candidate agent has affected the ATP transport activity.

Alternatively, it is also possible to perform screening of an activity regulator of an anion transport protein by:

(a) preparing cells that express the membrane protein of the present invention (for example, transforming cells using the gene of the present invention), (b) adding (1) radiolabeled ATP only, and (2) radiolabeled ATP and a candidate agent, respectively, to the cells, and incubating the cells, (c) disrupting the cells, preparing membrane fractions, and comparing the amount of radiolabeled ATP present in the membrane fraction in the instance of (1) and the same amount in the instance of (2), and (d) determining whether the candidate agent has affected the ATP transport activity.

(Screening of Medicinal Candidate Drug)

An inhibitor or activity regulator of the transporter (polypeptide and/or nucleic acid) of the present invention serves as a controlling agent for cellular/biological reactions in which puringergic chemical mediators directly or indirectly participate. This is because, without being bound by any one theory, when the transporter activity of a nucleotide (for example, ATP), which is a neurotransmitter, is inhibited, the amount of nucleotide that is exocytosed is decreased, and the puringergic chemical transmission involving a purine receptor, which is a type of nucleotide receptor, is decreased or lost. As a result, the transport of excitatory neurotransmitters into synaptic vesicles is inhibited, and as a result, the electrical excitation caused by excitatory neurotransmitters is suppressed. Furthermore, it is understood that such inhibitory action also inhibits the signal transduction not only of purine (nucleotide) but also of nucleosides. This is because, since a released nucleotide (for example, ATP) is rapidly decomposed to adenosine by extracellular ecto-ATPase, and this adenosine causes various responses through adenosine receptors. If the amount of adenosine produced is decreased or lost due to the above-described inhibitory action, it is anticipated that the signal transduction involving adenosine will be also decreased or lost per se. For that reason, an inhibitor against the transporter of the present invention can be used for the treatment, prevention and/or prognosis of diseases and/or conditions associated with, for example, excessive neural excitation (for example, epilepsy). Therefore, when the polypeptide and/or nucleic acid of the present invention is used to provide inhibitors thereof, anti-inflammatory agents, and therapeutic drugs for diseases selected from the group consisting of tremor, epilepsy, Parkinson's disease, Alzheimer's disease, osteopetrosis and osteoporosis, can be provided.

Examples of the inhibitors of the transporter of the present invention as described above include antibodies, siRNA, antisense RNA, and RNA aptamers, but are not limited to these.

Furthermore, it is also possible to develop a function activator which augments the activity of the transporter of the present invention, by employing the transporter of the present invention. The inventors of the present invention confirmed that chloride ions bring about the activation of a nucleotide transporter of the present invention. Such a function activator may be a mimicer of chloride ions, but is not limited to this.

Hereinafter, the present invention will be described by way of examples, but the following examples are provided only for the purpose of illustration. The scope of the invention is intended to be limited to neither the detailed description of the invention nor the following examples, and is defined by the claims.

EXAMPLES

Figure 1:
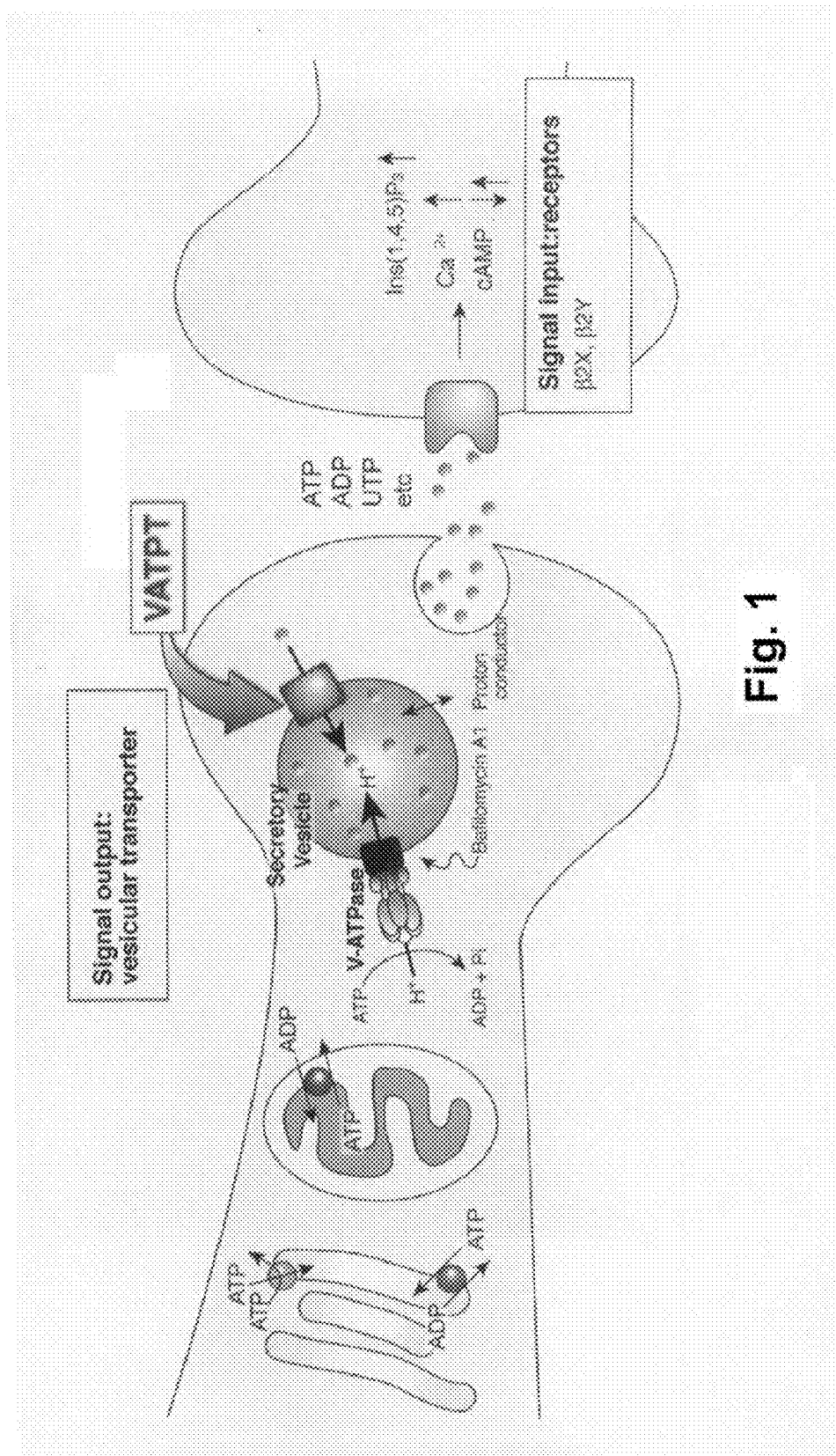
FIG. 1 is a diagram schematically depicting the ATP chemical transmission system. VNUT is the protein of the present invention.

The ATP transport activity in secretory vesicles that has been most thoroughly analyzed in researches down to date, is found in the chromaffin granules of adrenal medulla (Bankston L A, Guidotti G. (1996) J. Biol. Chem. 271, 17132-17138). Chromaffin granules contain approximately 0.1 M ATP and several ten mM ADP. It is known that transport of ATP in the granule membrane is such that Km with respect to ATP or ADP is relatively high, as high as up to several mM, and within the electrochemical potential difference of protons formed by vacuolar ATPase, the inner part of the membrane utilizes the positive membrane potential as an energy source for the transport. It is also known that the transport is promoted by about 10 mM chloride ions. Therefore, transport of nucleotides including ATP in the granule membrane is thought to be attributable to a secondary active transporter. This hypothetical ATP transporter is called a vesicular nucleotide transporter (VNUT) (FIG. 1).

Nothing was known with regard to this hypothetical ATP transporter, not about the structure or even its existence. Thus, the inventors of the present invention established a hypothesis, based on the fact that ATP is an anion under physiological conditions, that this transporter is an anion transporter. The inventors then attempted to clone the ATP transporter based on the hypothesis.

Figure 3:
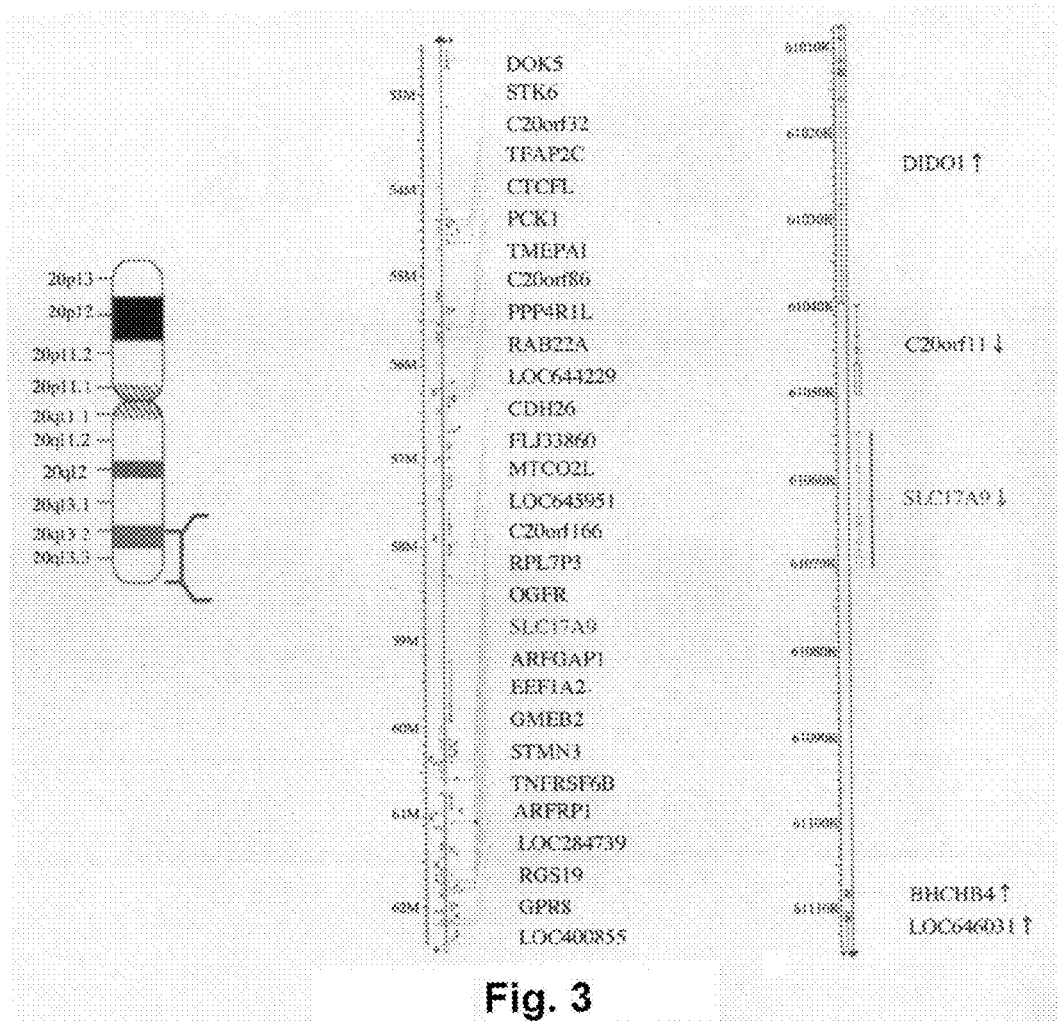
FIG. 3 is a diagram showing the genetic locus of SLC17A9 on human chromosome.

The SLC17A family consists of anion transporters (FIG. 2). Among the members of SLC17A, SLC17A1 through SLC17A4 (also called as NPT1 through NPT4) are Na$^+$-dependent phosphate transporters. SLC17A6 through SLC17A8 are vesicular glutamate transporters present in secretory vesicles. The inventors of the present invention found, through a search of mammalian genome sequences, that there exists a ninth member of the SLC17A family, SLC17A9, which has not been identified. It was found that this SLC17A9 gene is present on human chromosome 20 (FIG. 3). The nucleic acid sequence of human SLC17A9 (SEQ ID NO: 1) is presented in FIG. 4, and the amino acid sequence (SEQ ID NO: 2) is presented in FIG. 5. As shown in FIG. 5 as TMD1 through TMD12, the SLC17A9 membrane protein was predicted to have 12 transmembrane regions.

The present inventors predicted that this new member SLC17A9 would be a VNUT, based on the fact that the properties regarding ATP transport activity in the chromaffin granules, namely, a high Km value, chloride ion dependency and driving force, are similar to those of the vesicular glutamate transporters of SLC17A6 to SLC17A8.

It was difficult to measure in vitro the functions of a recombinant transporter whose inner part is driven by a positive membrane potential. Thus, the present inventors have developed a method for measuring the in vitro function of a vesicular glutamate transporter (Juge N, Yoshida Y, Yatsushiro S, Omote H, Moriyama Y. (2006) J. Biol. Chem., 281, 39499-39506). By using this testing method, this operating hypothesis can be verified. The present inventors verified this operating hypothesis according to a unique method, and found that the membrane protein encoded by SLC17A9 gene is a VNUT itself. The experiments used to obtain this finding will be described in the following examples.

Example 1

Isolation of SLC17A9 Gene by PCR (PCR)

A 0.2 mM dNTP mixed liquid, 1 pmol of primers, and 1.5U of Ex Taq (Takara) were added into Ex TaqBuffer (Takara) to a volume of 500, and PCR was performed using the resultant. The primers used were a forward primer (SEQ ID NO: 3; 5'-CACCATGACCCTGACAAGCAGGCGCCAGGA-3') and a reverse primer (SEQ ID NO: 4; 5'-CTAGAGGTCCT-CATGGGTAGAGCTC-3'). The PCR conditions included heating for 3 minutes at 94° C., subsequent 30 repetitions of a cycle of 3 minutes at 94° C., 30 seconds at 56° C., and 2 minutes at 72° C., and then heating for 5 minutes at 72° C.

(Linking to Entry Vector)

A PCR fragment was incorporated into an entry vector (pENTR, Invitrogen) using a TOPO cloning kit (Invitrogen). The reaction solution (6 μ) was a solution containing 1 μl of a salt solution (Invitrogen), 10 fmol of the vector (Invitrogen), and 20 fmol of the PCR product. The reaction was carried out at room temperature for 10 minutes, to thereby incorporate SLC17A9 into the entry vector. This was used as a TOPO reaction liquid.

(Transformation)

To 50 μl of *Escherichia coli* (*E. coli*) Mach-1 competent cells (Invitrogen), 2 μl of the TOPO reaction liquid was added. The mixture was left to stand on ice for 30 minutes, and then 250 μl of SOC medium (Invitrogen) was added thereto. The mixture was allowed to react for one hour at 37° C., and the entire amount was inoculated onto an LB plate containing 50 μg/ml of kanamycin. The plate was cultured overnight at 37° C., and single colonies were picked up and were cultured overnight in 3 ml of an LB medium containing 50 μg/ml of kanamycin. From the cultured *E. coli*, a vector containing SLC17A9 (pENTR/SLC17A9) was obtained using a QIAprep Spin Miniprep Kit (Qiagen). Using this vector, cDNA sequencing of SLC17A9 was performed.

The nucleic acid sequence of human SLC17A9 is presented in FIG. 4, and the amino acid sequence is presented in FIG. 5. Furthermore, an alignment of the amino acid sequence of human SLC17A9 with the amino acid sequences of SLC17A9 of other organisms is presented in FIG. 6.

Example 2

Expression and Purification of SLC17A9 Membrane Protein (Recombination into pDEST10)

The cDNA of SLC17A9 was cloned into a pDEST10 vector from the pENTR/SLC17A9 produced in Example 1, using LR clonase. To 150 ng of the pENTR/SLC17A9 plasmid were added 300 ng of a pDEST10 plasmid and 4 μl of LR clonase, and the mixture was incubated for one hour at 25° C. Subsequently, 2 μl of proteinase K was added thereto, and the mixture was incubated for 30 minutes at 37° C. The reaction liquid was used to transform DH5α competent cells of *E. coli*. The resultant plasmid was recovered from the transformed DH5α cells using a QIAprep Spin Miniprep Kit (Qiagen), and was designated as pDEST10/SLC17A9.

(Production of Recombinant bacmid)

The cDNA of SLC17A9 was incorporated into the baculovirus genome (bacmid) using the pDEST10/SLC17A9, using the Baculovirus Expression System with Gateway Technology (Invitrogen).

Specifically, 20 ng of pDEST10/SLC17A9 was added to 25 μl of DH10Bac competent cells (Invitrogen), the cells were left to stand on ice for 30 minutes, and 225 μl of SOC medium was added at 42° C. over 30 seconds. The mixture was incubated for 4 hours at 37° C., and the cells were inoculated onto an LB plate containing 50 μg/ml of kanamycin, 7 μg/ml of gentamycin and 10 μg/ml of tetracycline, and were incubated overnight at 37° C. The bacmid was then recovered by a miniprep method.

(Miniprep Method; for bacmid)

The miniprep method used in the production of recombinant bacmid was carried out by the following procedure. First, DH10Bac cells carrying the recombinant bacmid was inoculated into 3 ml of an LB medium containing 50 μg/ml of kanamycin, 7 μg/ml of gentamycin and 10 μg/ml of tetracycline, and the cells were cultured at 37° C. The cultured *E. coli* cells were suspended in 2000 of solution 1 (50 mM glucose, 25 mM Tris/HCl pH 8.0, and 10 mM EDTA pH 8.0), subsequently 200 μl of solution 2 (0.2M NaOH and 1% SDS) was added, and the mixture was mixed by inversion. The resultant was left to stand for 5 minutes at room temperature, subsequently 200 μl of solution 3 (3M KOAc and 11.5% (v/v) acetic acid) was added thereto, and the mixture was mixed by inversion. The resultant was then left to stand for 10 minutes at 4° C., and then was centrifuged (13,000 rpm, 15 minutes, 4° C.), and the supernatant was removed. A precipitate resulting therefrom was further washed two times with 70% ethanol. To this, a TE buffer solution (10 mM Tris/HCl pH 8.0, and 0.1 mM EDTA) was aseptically added, and the resultant was stored at 4° C.

(Preparation of Virus)

The virus used in the present invention was prepared by the following procedure. First, $9 \times 10^5$ Sf9 cells were inoculated onto a 35-mm petri dish. The medium was replaced with Grace's Insect Medium (GIBCO) added with 0.35 mg/ml of sodium hydrogen carbonate, and then 1 μg of the bacmid containing SLC17A9 and 6 μl of cellfectin (Invitrogen) were used to infect Sf9 by a lipofection method. The cells were incubated for 5 hours at 27° C., the medium was then replaced with 2 ml of complete TMN-FH, and the cells were cultured until the signs of infection were visible. The medium was recovered, and the resulting product was designated as P1 virus. Then, $6 \times 10^6$ Sf9 cells were inoculated (50% confluent) onto a 100-mm petri dish, 1 ml of a virus solution obtained by 10-fold serial dilution was added thereto, and the petri dish was shaken for one hour at room temperature. The content of the petri dish was mixed such that the ratio of complete TMN-FH:4% SeaPlaque Agarose would be 3:1, the medium of the petri dish was removed, and then the petri dish was sealed using 10 ml of multilayered agarose for 7 to 10 days at 27° C. to culture the cells. The plaques formed thereon were picked up, and infected again. After 72 hours, this medium was recovered in the same manner as in the case of the P1 virus, and the resulting product was designated as P2 virus.

(Recovery of Cells and Solubilization of Membrane Fraction)

HighFive cells were infected with the P2 virus at M.O.I.=1, and the cells were cultured at 27° C. After 60 hours of infection, the cells were recovered using a cell scraper, and were centrifuged at 700×g for 10 minutes, and the supernatant was removed. The remnant was suspended in a disruption buffer solution (20 mM Tris-HCl pH 8.0, 100 mM potassium acetate, 10% glycerol, 5 mM DTT, 1 μg/ml pepstatin A (Peptide Laboratory), and 1 μg/ml leupeptin (Peptide Laboratory)), the suspension was centrifuged again at 700×g for 10 minutes, and the supernatant was removed. The resultant was suspended in a disruption buffer solution and treated by ultrasonication (with a TOMY ultrasonic disruptor, Output 4, seconds ×8 times), subsequently the suspension was centrifuged at 700×g for 10 minutes, and the supernatant was removed. The remnant was ultracentrifuged at 100,000×g for one hour at 4° C., and the resulting precipitate was designated as a membrane fraction. This fraction was suspended by adding a solubilizing buffer solution (20 mM MOPS-Tris pH 7.0, 2% octyl glucoside (Dojindo Laboratories, Ltd.), 10% glycerol, 1 μg/ml pepstatin A, and 1 μg/ml leupeptin) and using a homogenizer. The suspension was subjected to centrifuge operation at 100,000×g for 30 minutes, and the supernatant was designated as a solubilized fraction.

(Purification of SLC17A9 Using Affinity Column)

An Econo column was packed with QIAGEN Ni-NTA Superflow resin (1 mL; 50% slurry), and the column was washed with distilled water, and then equilibrated with a solubilizing buffer solution at pH 8.0. The aforementioned solubilized fraction was added to this column, and the solubilized fraction was allowed to adsorb while the content was stirred for 4 hours at 4° C. This resultant was washed with 15 ml of a washing buffer solution (20 mM MOPS-Tris pH 7.0, 1% octyl glucoside, 20% glycerol, 5 mM imidazole, 1 μg/ml pepstatin A, and 1 μg/ml leupeptin), and purified SLC17A9 was eluted using an elution buffer solution (20 mM MOPS-Tris pH 7.0, 1% octyl glucoside, 20% glycerol, 60 mM imidazole, 1 μmg/ml pepstatin A, and 1 μg/ml leupeptin).

Figure 7:
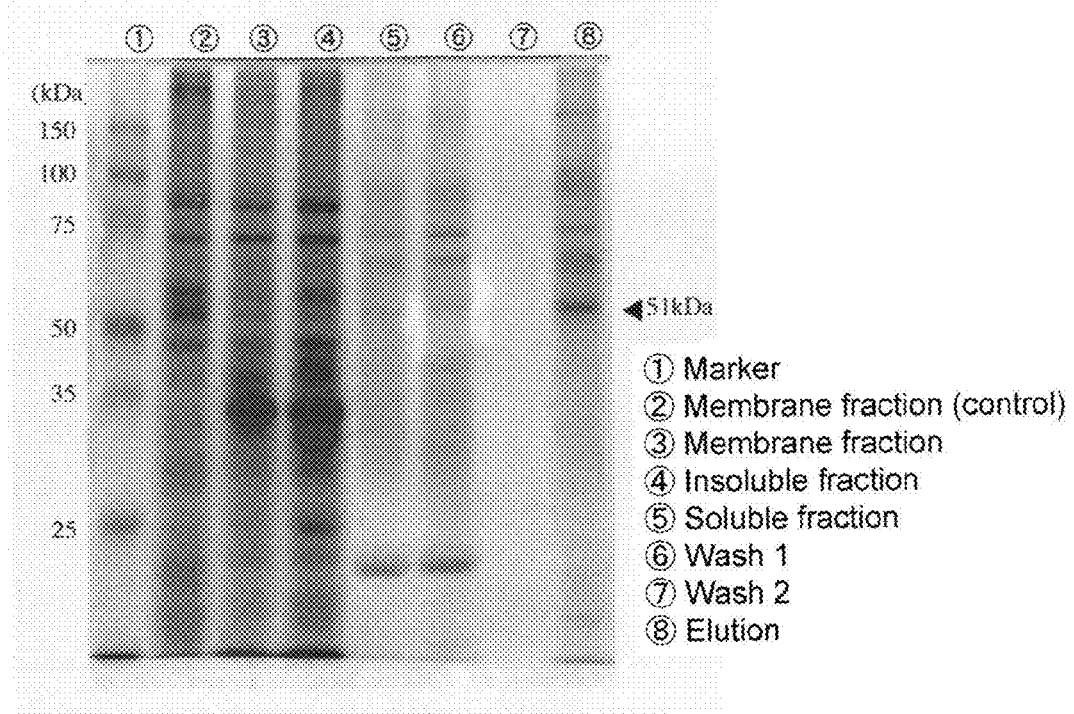
FIG. 7 is a photograph of SDS polyacrylamide electrophoresis of purified SLC17A9 and of various fractions in the middle of purification.

The results of SDS gel electrophoresis of the purified SLC17A9 are presented in FIG. 7. It can be seen from these results that SLC17A9 was purified according to the method of the current example.

Example 3

Purification of $F_oF_1$-ATPase $F°F^1$ protein, which is a proton pump, was prepared according to the procedure described in Moriyama Y, et al., J. Biol. Chem. 266, 22141-22146 (1991).

*E. coli* DK8 containing pBWU13, which is a high expression plasmid of $F_oF_1$, was cultured in Tanaka medium (34 mM monopotassium phosphate, 64 mM dipotassium phosphate, 20 mM ammonium sulfate, 0.3 mM magnesium chloride, 1 μM iron sulfate, 1 μM calcium chloride, 1 μM zinc chloride, 100 μg/ml isoleucin, 100 μg/ml valine, and 2 μg/ml thiamine) supplemented with 0.5% glycerol, and then the bacterial cells were recovered. The subsequent preparation processes were all carried out at 4° C.

About 10 g of the bacterial cells (DK8/pBWU13) was suspended in 40 ml of a membrane preparation buffer solution (50 mM Tris-HCl (pH 8.0), 2 mM magnesium chloride, 0.5 mM EDTA, 1 mM PMSF, 1 μg/ml leupeptin, 1 μg/ml pepstatin A, 10% (v/v) glycerol, and 1 mM DTT at 4° C.), and the cells were disrupted with a French press (1,500 kg/cm$^2$). The disrupted cell liquid was centrifuged at 17,000×g for 10 minutes, and the resulting supernatant was further centrifuged at 210,000×g for 1 hour 20 minutes. A precipitate of the resulting membrane vesicle was suspended in a buffer solution for $F_oF_1$ preparation (20 mM MOPS/NaOH (pH 7.0), 1 mM magnesium sulfate, 1 mM DTT, 1 mM PMSF, and 0.8% octyl glucoside), and the suspension was centrifuged again. In 3 ml of a buffer solution for $F_oF_1$ preparation supplemented with 2% octyl glucoside was suspended 60 mg of the membrane vesicle prepared as a precipitate, to solubilize $F_oF_1$. The solubilized solution was centrifuged at 260,000×g for 30 minutes, and $F_oF_1$ was recovered from the supernatant fraction. The recovered $F_oF_1$ was purified by glycerol density gradient (10% (w/v) to 30% (w/v)) centrifugation (5 hours at 330,000×g). The glycerol density gradient was produced with a buffer solution for $F_oF_1$ preparation, supplemented with 1% octyl glucoside. After the density gradient centrifugation, the resultant was divided and separated into 10 fractions from the bottom of the centrifuge tube, and the first 4 fractions were recovered as $F_oF_1$ and were stored at −80° C.

Example 4

Reconstitution of $F_oF_1$ATPase and Purified SLC17A9 into Liposomes

In a buffer solution (20 mM MOPS/NaOH pH 7.0, 0.5 mM DTT) was suspended 20 mg of soybean lecithin (Sigma type IIS), and the suspension was sonicated in a bath type sonicator until clear. The prepared liposomes were divided into small aliquots and stored at −80° C.

Subsequently, 90 μg of the $F_oF_1$-ATPase purified by the technique of Example 3, and 20 μg of SLC17A9 purified by Example 2 were mixed into 600 μg of the liposomes, and the mixture was left to stand for 15 minutes at −80° C., and was frozen. This was immediately taken out and rapidly thawed. The resultant was diluted 20-fold with F buffer solution (20 mM MOPS-Tris pH 7.0, 100 mM potassium acetate, and 5 mM magnesium acetate), and was centrifuged at 160,000×g for 60 minutes. To the precipitate was added 400 μg of F buffer solution and homogenized to obtain reconstituted proteoliposomes.

Example 5

Expression Pattern of SLC17A9 Gene

Figure 8:
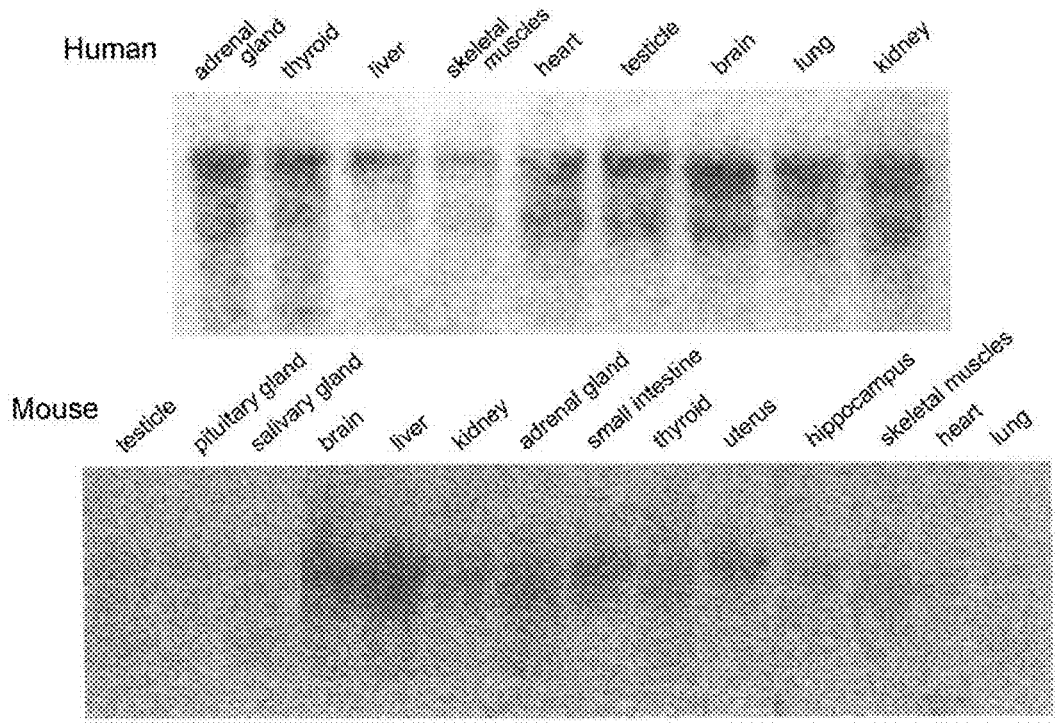
FIG. 8 is a photograph showing the results of a Northern blot of human and mouse SLC17A9 genes.

An RNA panel was produced as follows. First, total RNA (liver, skeletal muscles, heart, testicle, lung, kidney, adrenal gland, and thyroid) purchased from Clontech, Inc. (currently Takara Bio Company) was subjected to electrophoresis using 1% formaldehyde gel. The separated RNA was transferred to a Hybond N$^+$ membrane of Amersham Biosciences, Inc., and the RNA was fixed by crosslinking under ultraviolet radiation. This membrane was used to perform Northern blot analysis. Nucleotides 1029 to 1274 (296 bp) of human SLC17A9 was used as a probe, and was labeled with $^{32}$P-dCTP of GE Healthcare UL Limited. The hybridized membrane was photosensitized overnight using an imaging plate manufactured by FujiFilm Corporation, and this plate was scanned using an imaging analyzer manufactured by Fujifilm Corporation. As shown in FIG. 8, it was demonstrated that SLC17A9 gene is expressed in various tissues including adrenal medulla.

Example 6

Localization OF SLC17A9 Protein

An anti-SLC17A9 antibody was produced by the following method. A plasmid which expresses a peptide prepared by fusing a sequence from the amino-terminal to the 40$^{th}$ residue of human SLC17A9 (SEQ ID NO: 5: MTLTSRRQD-SQEARPECQAWTGTLLLGTCLLYCARSSMPI) into GST, was introduced into *Escherichia coli* strain BL21, the cells were induced with 1 mM IPTG for 3 hours, and then the *E. coli* cells were recovered. These *E. coli* cells were disrupted by ultrasonication, and then were centrifuged at 15,000×g for 30 minutes. The supernatant was recovered, and the fused protein of interest was recovered using a Glutathione Sepharose 4B column. It was confirmed by SDS gel electrophoresis that the obtained protein was a single protein, and the protein was injected to a white rabbit together with an adjuvant. After several injections (after about one month), the blood was collected and stored as serum. An anti-mouse SLC17A9 antibody was produced by the same procedure as that for the anti-human SLC17A9 antibody, using an amino acid sequence corresponding to a sequence from the amino-terminal to the 89$^{th}$ arginine residue (SEQ ID NO: 6:

MQPIPEETRKTPSAAAEDTRWSRPECQAWTGILLLGTCLLYCARVTMPVC

TVAMSQDFGWNKKEAGIVLSSFFWGYCLTQVVGGHLGDR).

Western blot analysis was performed using the primary antibody (serum), which had been diluted 1000-fold, according to the method by Moriyama and Nelson (Moriyama, Y. and Nelson, N (1988) J. Biol. Chem. 263, 8521-8527).

Specifically, the protein on the electrophoresed SDS polyacrylamide gel was subjected to electrophoresis in a buffer solution containing 9 g of Tris, 30 g of glycine, 0.6 g of SDS and 600 ml of methanol (total volume 3 L), at 350 mV for 2 hours, and was transferred to nitrocellulose. After the transfer, the protein was kept warm for 4 hours in a buffer solution prepared by adding 1% BSA to TEN buffer solution, and then the primary antibody was added to the same buffer solution and kept warm for 2 hours. Subsequently, the protein was washed two times for 15 minutes with a buffer solution prepared by adding 0.05% Tween 20 to TEN buffer solution, and then the protein was reacted for 30 minutes with the secondary antibody in the same buffer solution. After the reaction, the liquid was decanted, and the protein was washed for another 4 hours. After the washing, the peroxidase on the antibody remaining in nitrocellulose was allowed to react by an ECR method.

Figure 9:
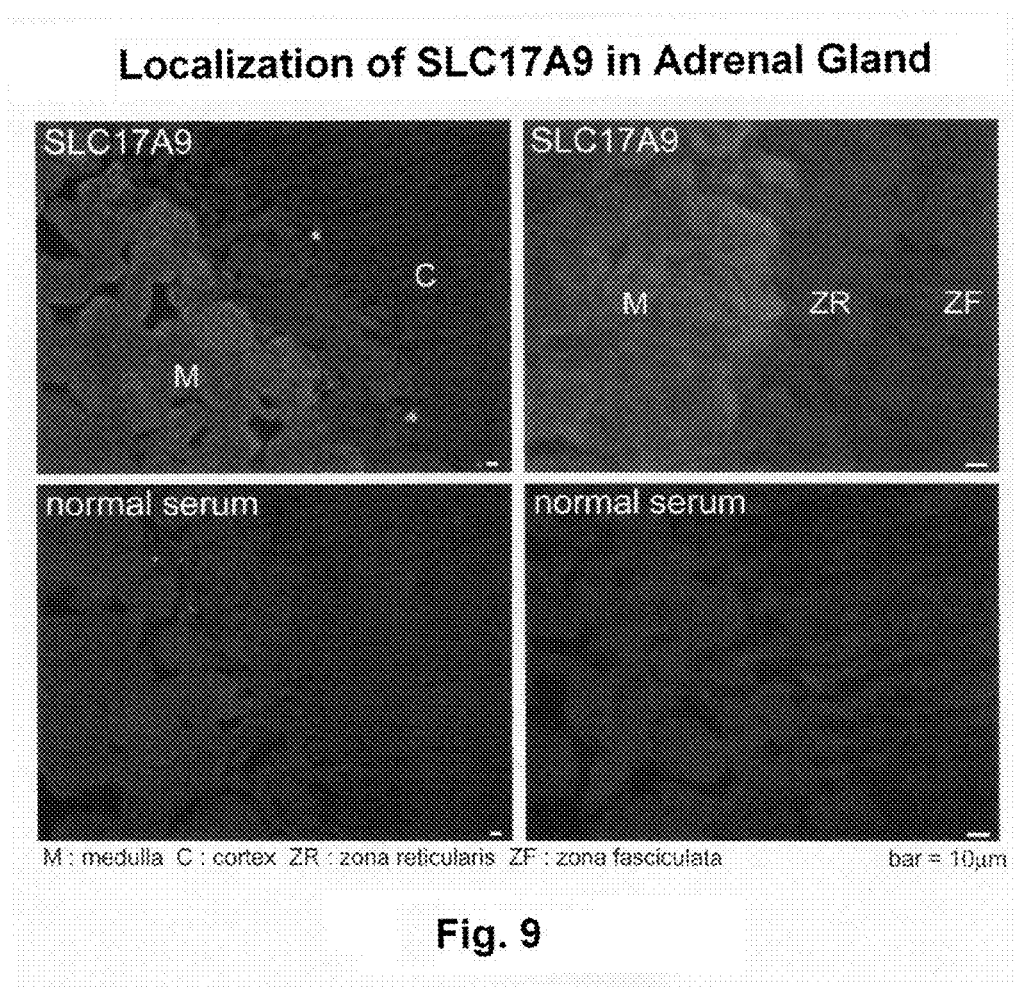
FIG. 9 is a photograph showing the results of a Western blot indicating localization of SLC17A9 protein in chromaffin granules.

As a result, it was found that SLC17A9 is present in the chromaffin granules (FIG. 9).

From the results of these Example 5 and Example 6, it was verified that SLC17A9 is a membrane protein responsible for the transport of ATP in the chromaffin granules, that is, a VNUT.

Example 7

Measurement of ATP Transport Activity

Figure 10:
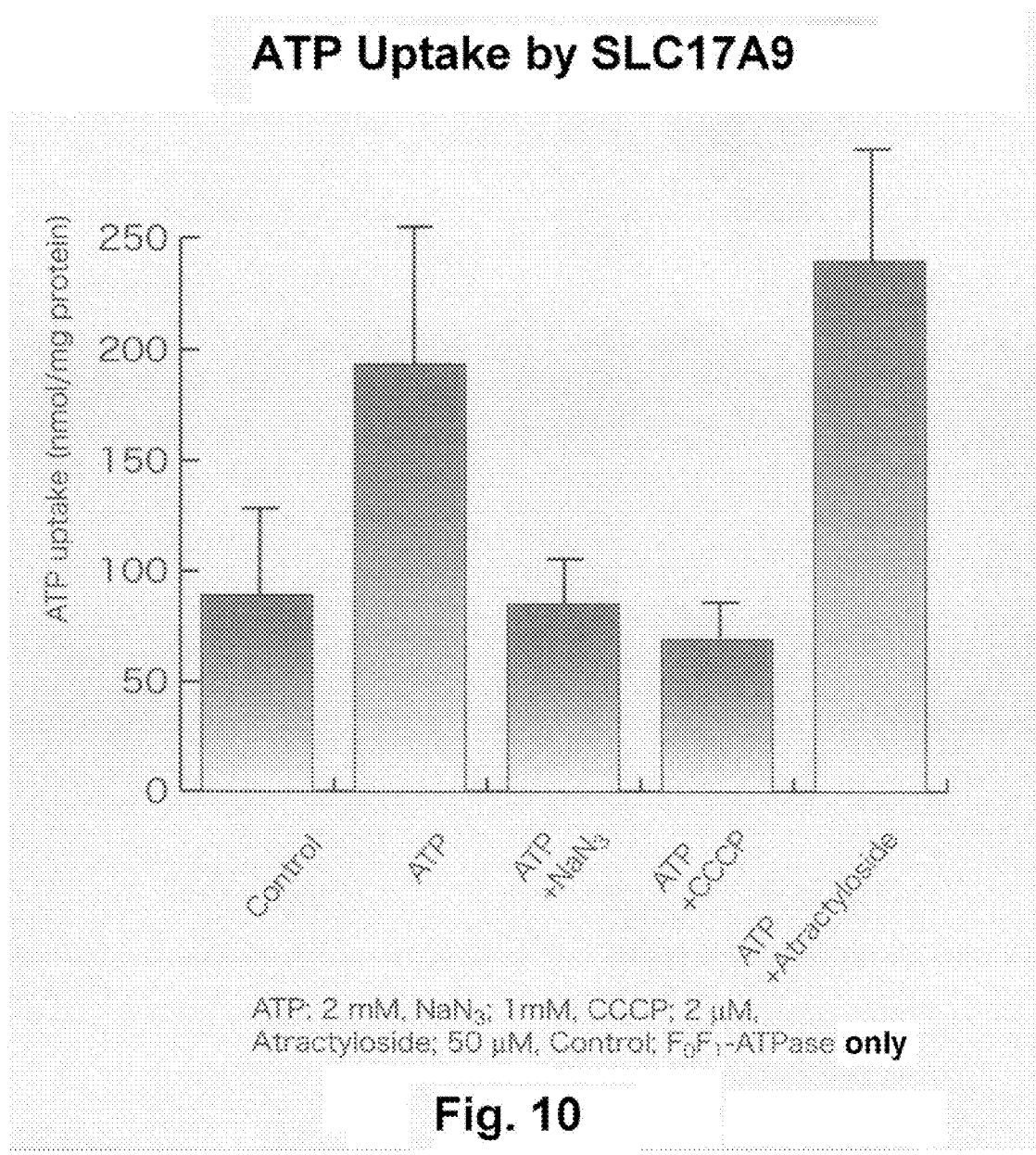
FIG. 10 shows the results indicating the uptake of ATP by SLC17A9.

16 μl of the proteoliposomes prepared in Example 4 and F buffer solution were added, and the mixture was incubated for 2 minutes in a water bath at 27° C. Subsequently, ATP (1.3 µCi) was added to a final concentration of 2 mM, and the reaction was initiated. 125-µl aliquots of the sample liquid were taken and applied to a Sephadex G-50 fine spin column. The reaction system was centrifuged at 180×g for 2 minutes to terminate the reaction. The eluate was dissolved in 3 ml of a clear-sol, and the radioactivity (corresponding to the ATP taken up by the liposomes) present in the solution was measured using a liquid scintillation counter. Also, as shown in the diagram, 1 mM $NaN_3$ (+$NaN_3$), 2 µM CCCP (+CCCP) and 50 µM atractyloside (+Atractyloside) were used. The results are presented in FIG. 10. It was shown that uptake of ATP into liposomes was observed by adding ATP, and that this uptake essentially requires SLC17A9, and this uptake is driven by the membrane potential.

Example 8

Screening of Activity Regulator of ATP Transport Activity

16 µl of the proteoliposomes prepared in Example 4 and F buffer solution were added, and the mixture was incubated for 2 minutes in a water bath of 27° C. Subsequently, a candidate drug was added (representatively, in an amount of about 1/100 to 1/1000 of the total reaction volume, to a final concentration of about 1 µM to 1 mM). Subsequently, ATP (1.3 µCi) was added to a final concentration of 2 mM, and the reaction was initiated. 125-µl aliquots of the sample liquid were taken and applied to a Sephadex G50 fine spin column. The reaction system was centrifuged at 180×g for 2 minutes, to terminate the reaction. The eluate was dissolved in 3 ml of a clear-sol, and the radioactivity (corresponding to the ATP taken up by the liposomes) present in the solution was measured using a liquid scintillation counter. The results were compared with the results obtained without adding the candidate drug (for example, results of Example 5), and thereby it can be determined as to whether this candidate drug promotes or inhibits/suppresses the ATP transport activity.

Example 9

SLC17A9 in Mouse Adrenal Medulla

To confirm the location of SLC17A9 in mouse adrenal medulla, gold colloid silver-sensitized electron microscopy was performed as follows. In a mouse anesthetized with ether, physiological saline was perfused from the heart, and then 0.1 M sodium phosphate buffer solution (pH 7.4) having 4% paraformaldehyde dissolved therein was perfused. The adrenal gland was isolated and washed with PBS. The adrenal gland was dehydrated with ethanol, was embedded in an LR-White resin, and then was sliced (80 nm thick). The slices were incubated in a PBS supplemented with 2% goat serum and 2% BSA (blocking solution) for 10 minutes. Subsequently, the slices were incubated together with a rabbit anti-mouse SLC17A9 antibody diluted with the blocking solution to 20 times, for one hour at room temperature. The slices were sufficiently washed with the blocking solution, and then were incubated for 30 minutes in a blocking solution containing an anti-rabbit IgG gold colloid (the diameter of metal particles was 10 nm). The slices were washed 6 times with a 0.1M Na-cacodylate buffer solution (pH 7.4), and then were fixed for 10 minutes using 2.5% glutaraldehyde. After further washing, the slices were double-stained with uranium acetate and lead citrate, and were analyzed with a Hitachi H-7100 electron microscope.

Figure 11:
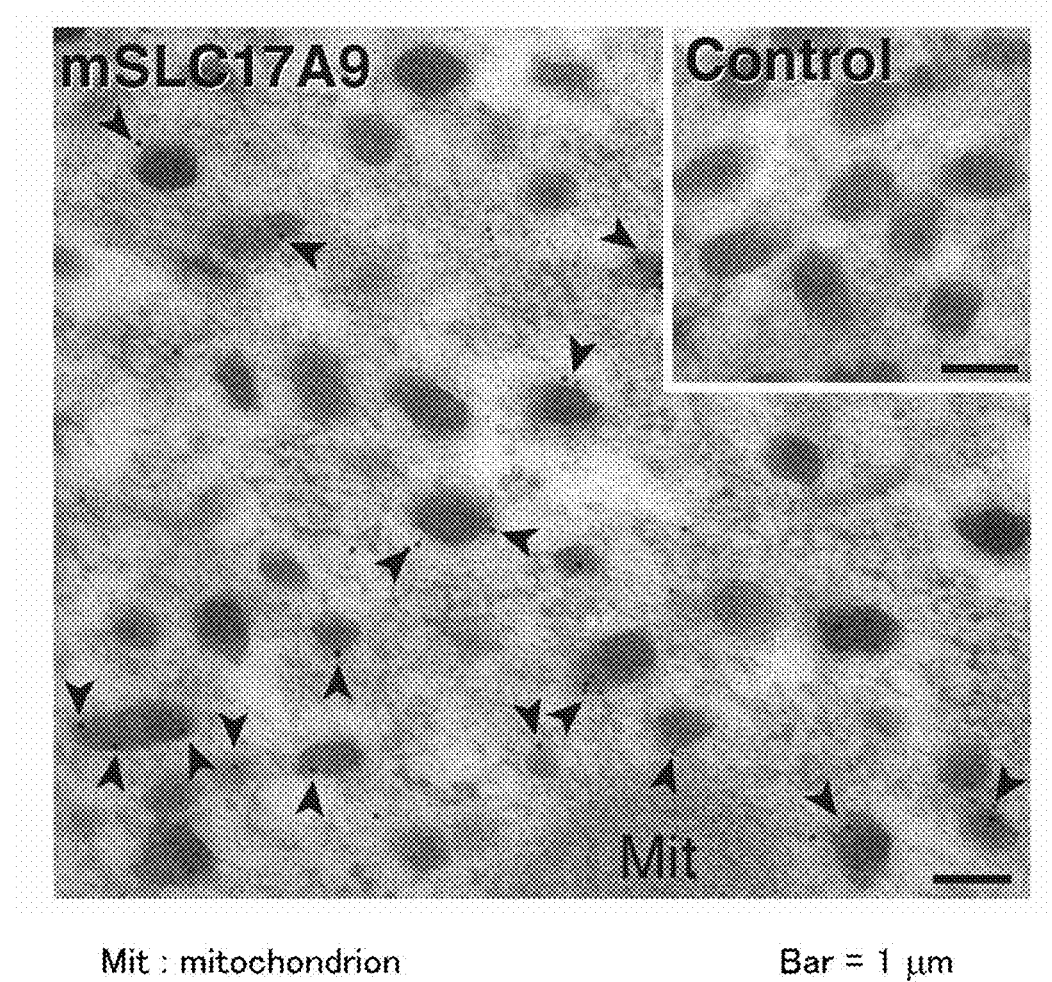
FIG. 11 is a photograph showing an immunoelectron microscopic image of mouse SLC17A9 in adrenal medulla.

The results are presented in FIG. 11. FIG. 11 is a photograph showing an immunoelectron microscopic image of mouse SLC17A9 in adrenal medulla. The presence of mouse SLC17A9 is indicated by gold colloid. The gold colloid is present in the chromaffin granules, indicating that the SLC17A9 protein is on the granules. In the diagram, Mit represents mitochondria. The scale bar indicates 0.1 µm.

Example 10

Expression of SLC17A9 in Bovine Adrenal Gland and Chromaffin Granules

Figure 12:
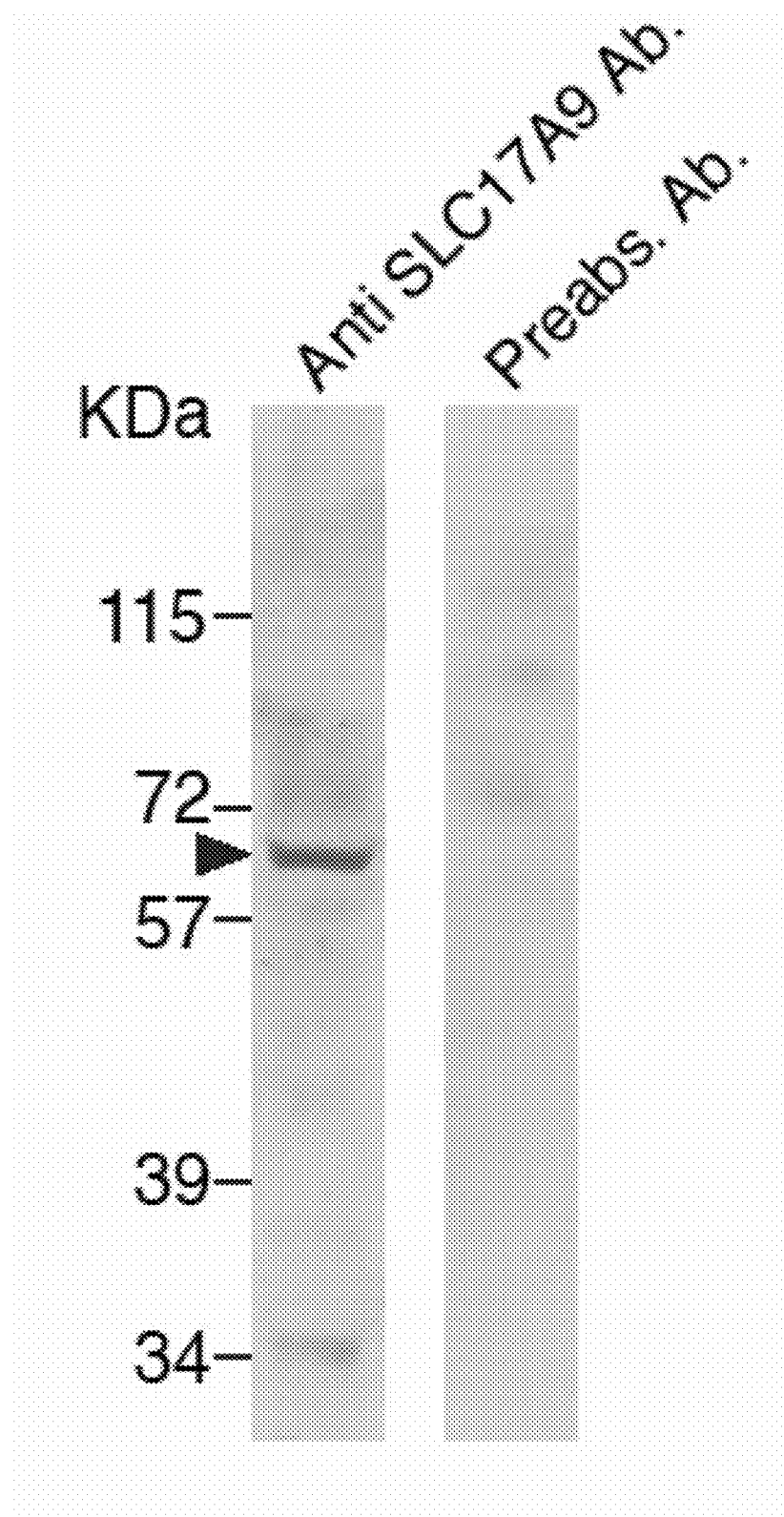
FIG. 12 is a photograph showing the results of a Western blot analysis confirming the expression of SLC17A9 in the bovine adrenal gland and chromaffin granule membrane.

Bovine chromaffin granule membrane was prepared by the method by Nelson et al. (Nelson N, Cidon S, Moriyama Y. (1988) Method Enzymol 157, 619-633), and Western blot analysis was performed using an anti-mouse SLC17A9 antibody. As a result, there was one distinct protein that is recognized by the anti-mouse SLC17A9 antibody, and the presence of a counterpart of SLC17A9 could be confirmed (left lane). The recognition reaction of this protein by the anti-mouse SLC17A9 antibody was absorbed by an antigen peptide (L8 to R97 of mouse SLC17A9) (right lane). The results are presented in FIG. 12.

Example 11

Formation of Membrane Potential by SLC17A9 Reconstituted Proteoliposomes

10 µg of purified SLC17A9 and 0.5 mg of soybean-derived lipids were mixed and incubated at −80° C. for 5 minutes or more. The mixture was thawed quickly by holding the tube in the hands, and was diluted 60-fold with a buffer solution containing 20 mM MOPS-Tris (pH 7.0), 0.15M sodium acetate, 2 mM magnesium acetate and 0.5 mM DTT. This dilution was centrifuged at 200,000×g at 4° C. for one hour, the supernatant was discarded, and the precipitate was resuspended in a buffer solution containing 20 mM MOPS-Tris (pH 7.0), 0.15M sodium acetate, 2 mM magnesium acetate and 0.5 mM DTT, to obtain SLC17A9 reconstituted proteoliposomes. As a control, liposomes without SLC17A9 were used.

The measurement of membrane potential difference using Oxonol-V was carried out by the method described in Moriyama Y and Yamamoto A (1995) J. Biol. Chem. 270, 22314-22320, using a fluorescent spectrophotometer.

The nucleotide transport activity was measured by the following procedure. The reconstituted proteoliposomes were incubated in a buffer solution containing 20 mM MOPS-Tris (pH 7.0), 0.15M potassium acetate, 2 mM magnesium acetate and 4 mM potassium chloride, at 27° C. for 2 minutes, and valinomycin was added thereto to a final concentration of 2 µM. The mixture was incubated for further 2 minutes. The point of addition of 0.1 mM [$\alpha$-$^{32}$P]ATP (3.7 GBq/mmol) was defined as the initiation of activity measurement. At a predetermined time point, 130 µL of the reaction liquid was recovered and centrifuged through a Sephadex G-50 (fine) spin column at 760×g for 2 minutes. The uptake of ATP was measured by measuring the radioactivity included in the reaction liquid that had passed through the column using a liquid scintillation counter. In the measurement of the transport activity for ADP and GTP, [2,8-$^3$H]ADP (0.37 GBq/mmol) and [$\alpha$-$^{32}$P]GTP (3.7 GBq/mmol) were used instead of ATP as the substrate.

In an experiment for an inhibitor, a predetermined concentration of an inhibitor was added upon incubation of the proteoliposomes. The results are presented in FIGS. 13(A) and 13(B). As shown in FIG. 13(A), fluorescence quenching of Oxonol-V was measured. A membrane potential difference was formed at the reconstituted liposomes by adding valinomycin (Val), which is a $K^+$ ionophore. This reaction did not occur in ethanol. Membrane potentials were generated in a manner similar to the case of liposomes that did not contain SLC17A9. As shown in FIG. 13(B), the uptake of radioactive ATP (100 μM) was observed over time using the proteoliposomes reconstituted with human SLC17A9. The uptake of ATP was activated when valinomycin was added. Therefore, it became clear that SLC17A9 transports ATP in a membrane potential-dependent manner. This uptake did not occur in the liposomes where SLC17A9 protein was not present. The graph in the upper right corner shows the results for the observation of ATP uptake at various concentrations. The Km value for ATP was 0.8 mM.

The previously used reconstituted proteoliposomes contained $F_oF_1$-ATPase, but the reconstituted proteoliposomes of the current example were reconstituted without using $F_oF_1$-ATPase. Therefore, it became possible to measure the true effect of an inhibitor on a transporter, by using the reconstituted proteoliposomes of the current example.

Example 12

ATP Transport by SLC17A9 Reconstituted Proteoliposomes Requires Chloride

Figure 14:
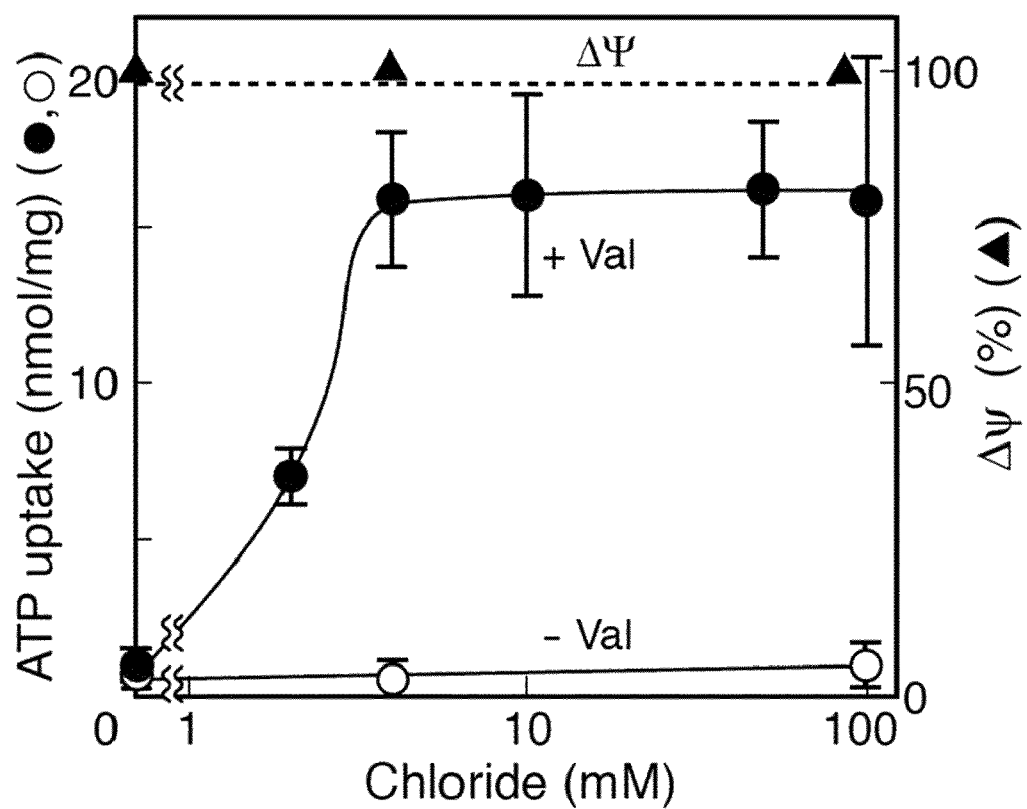
FIG. 14 is a graph showing the results of an observation of the ATP uptake in the presence of chloride ions at various concentrations.

ATP transport by SLC17A9 reconstituted proteoliposomes was observed using the same conditions as in Example 11, except that chloride ions at various concentrations were used. The ATP uptake activity reached a steady state at 4 mM of chloride ions, and was maintained. That is, it became clear that the SLC17A9 protein requires chloride ions in the ATP uptake. The results are presented in FIG. 14.

Example 13

Figure 15:
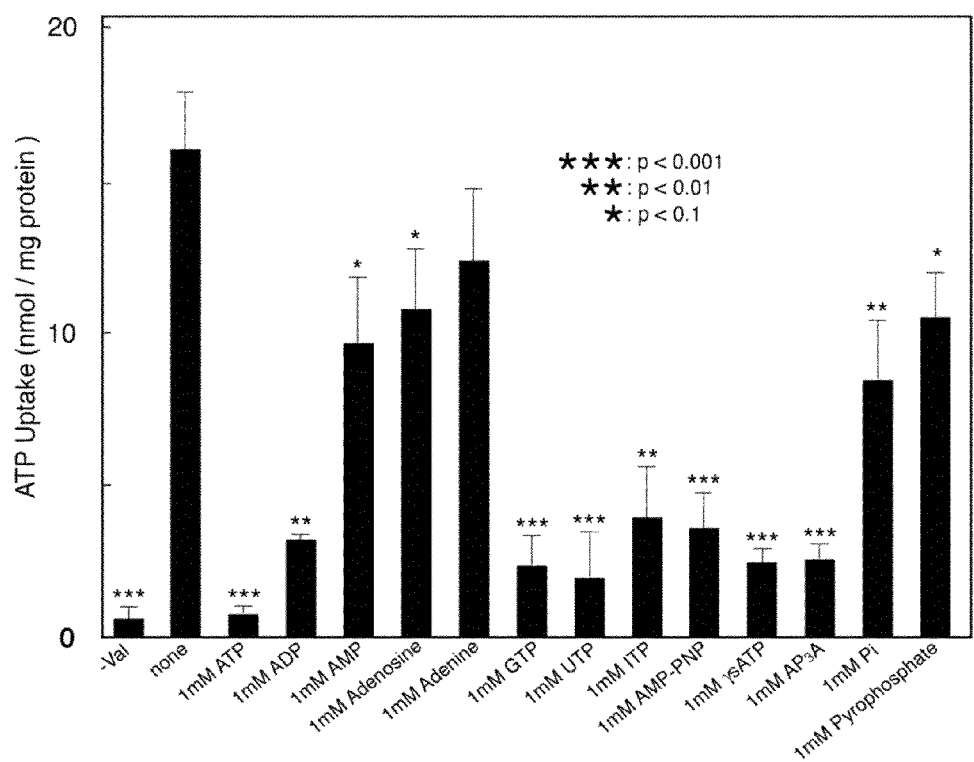
FIG. 15 is a graph showing the results obtained by an observation of the effect on the ATP uptake when various nucleotides (1 mM) were added.

Effect of Various Nucleotides on ATP Transport by SLC17A9 Reconstituted Proteoliposomes An experiment was performed to see whether various nucleotides (1 mM) affect the ATP transport by SLC17A9 reconstituted proteoliposomes. The results are presented in FIG. 15. These results suggest that ADP, GTP and the like are also recognized as transport substrates, in addition to ATP.

Example 14

ADP and GTP Transport by SLC17A9 Reconstituted Proteoliposomes

Figure 16:
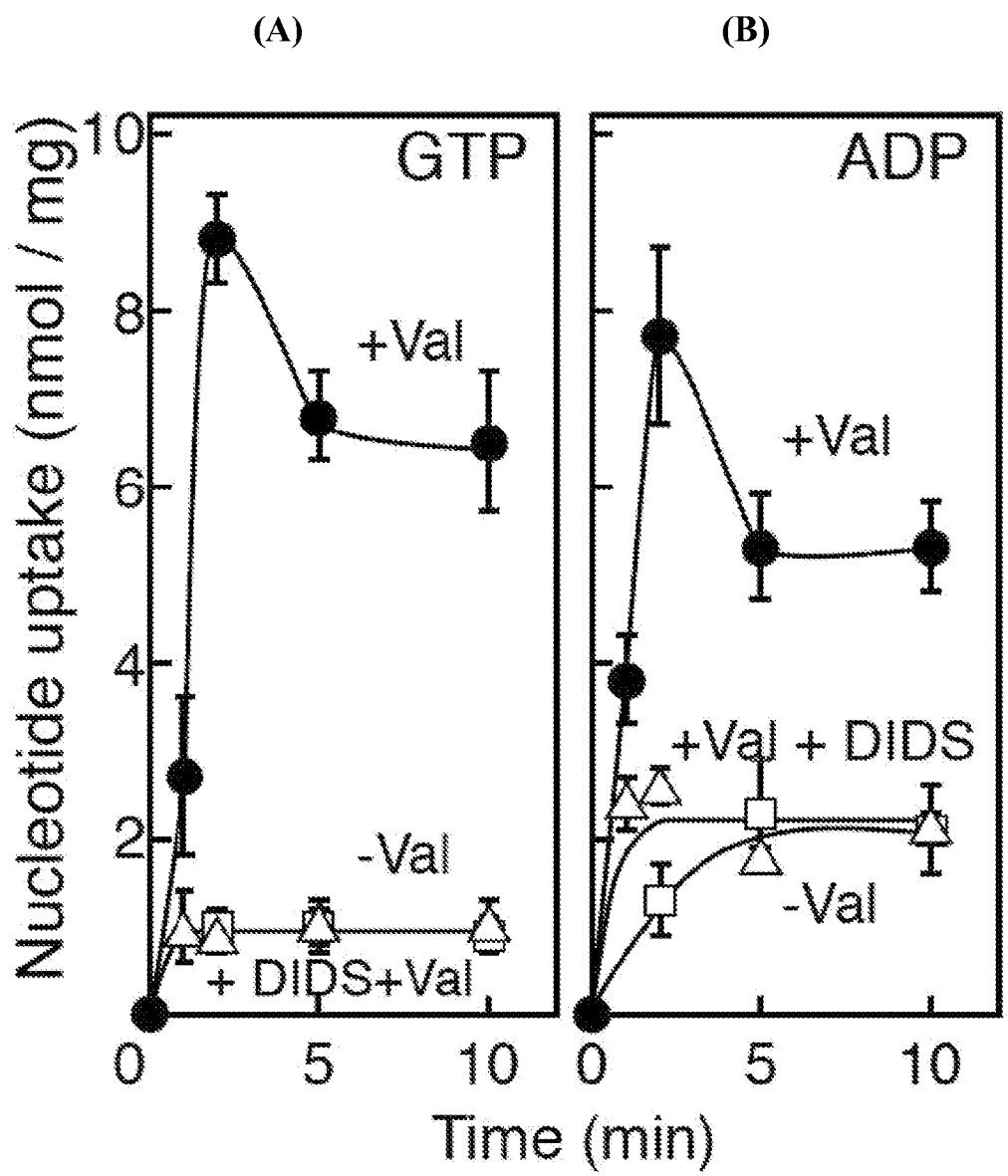
FIG. 16(A) and FIG. 16(B) are graphs obtained through an observation of the actual uptake of ADP and GTP (each 100 μM), respectively, over time.

The ADP and GTP transport by the SLC17A9 reconstituted proteoliposomes was measured, in order to determine whether SLC17A9 has a transport activity for nucleotides other than ATP (for example, ADP and GTP). FIG. 16(A) and FIG. 16(B) are graphs obtained by observing over time that ADP and GTP (100 μM respectively) were actually taken up into the SLC17A9 reconstituted proteoliposomes. It became clear that SLC17A9 is a nucleotide transporter that transports ATP as well as GTP.

Example 15

Measurement of Inhibitory Effect of ATP Transport Inhibitor

The concentration-dependent inhibition of the ATP uptake by DIDS (FIG. 17A) and Evans Blue (FIG. 17B) were measured. $ID_{50}$ values were 1.5 μM and 40 nM, respectively.

Figure 17:
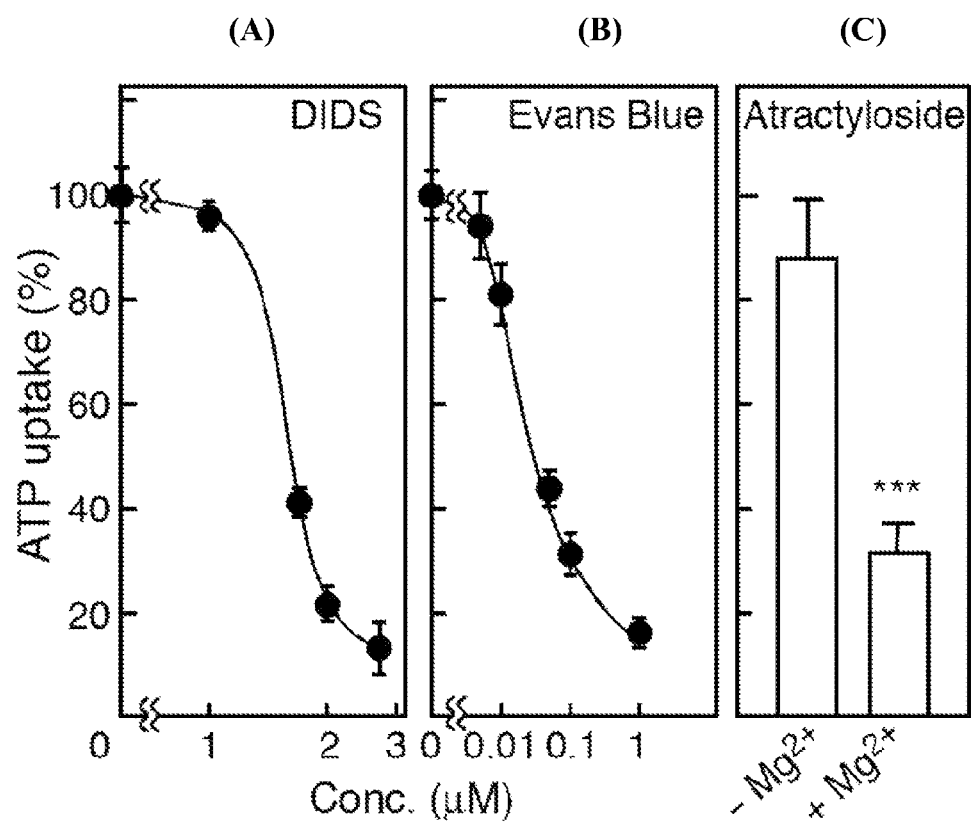
FIG. 17(A) and FIG. 17(B) are graphs obtained by measuring the concentration-dependent inhibition of the ATP uptake by DIDS (A) and Evans Blue (B).
FIG. 17(C) is a graph showing the results obtained by an observation of the effect on the ATP uptake when atractyloside (200 M) was added.

The effect of the addition of atractyloside (200 μM) on the ATP uptake was observed (FIG. 17(C)). Only when $Mg^{2+}$ was present, the ATP uptake was inhibited. From these two results, it became clear that an inhibitor of this transporter can be quantified with high accuracy by using the liposomes of the present invention.

Example 16

Transport Activity by Other Proteins Belonging to SLC17 Family

The ATP uptake of other proteins that belong to the SLC17 family, upon being reconstituted in a manner similar to the case of SLC17A9, was observed. Each of the transporter proteins that belong to the SLC17 family was purified in the same manner as in the case of SLC17A9, and was reconstituted according to the technique of Example 11. Also in regard to the transport activity, 0.1 mM $[\alpha\text{-}^{32}P]ATP$ was added in the same manner as in the case of SLC17A9, and the ATP uptake after 2 minutes was measured. The results are presented in the following Table 1.

TABLE 1

| Protein name | Gene name | ATP Transport (%) |
|---|---|---|
| SLC17A9 protein (VNUT) | SLC17A9 | 100.0 |
| NPT1 | SLC17A1 | 2.0 ± 1.1 |
| VGLUT2 | SLC17A6 | 0.1 ± 0.2 |
| VGLUT1 | SLC17A7 | 1.7 ± 0.7 |
| VGLUT3 | SLC17A8 | 7.1 ± 2.1 |
| Sialin | SLC17A5 | 2.1 ± 0.8 |

From these results, it was confirmed that the ATP transport activity by SLCA19 is unique and cannot be seen in other SLC family proteins.

Example 17

Localization of SLCA19 in Cells

Figure 18:
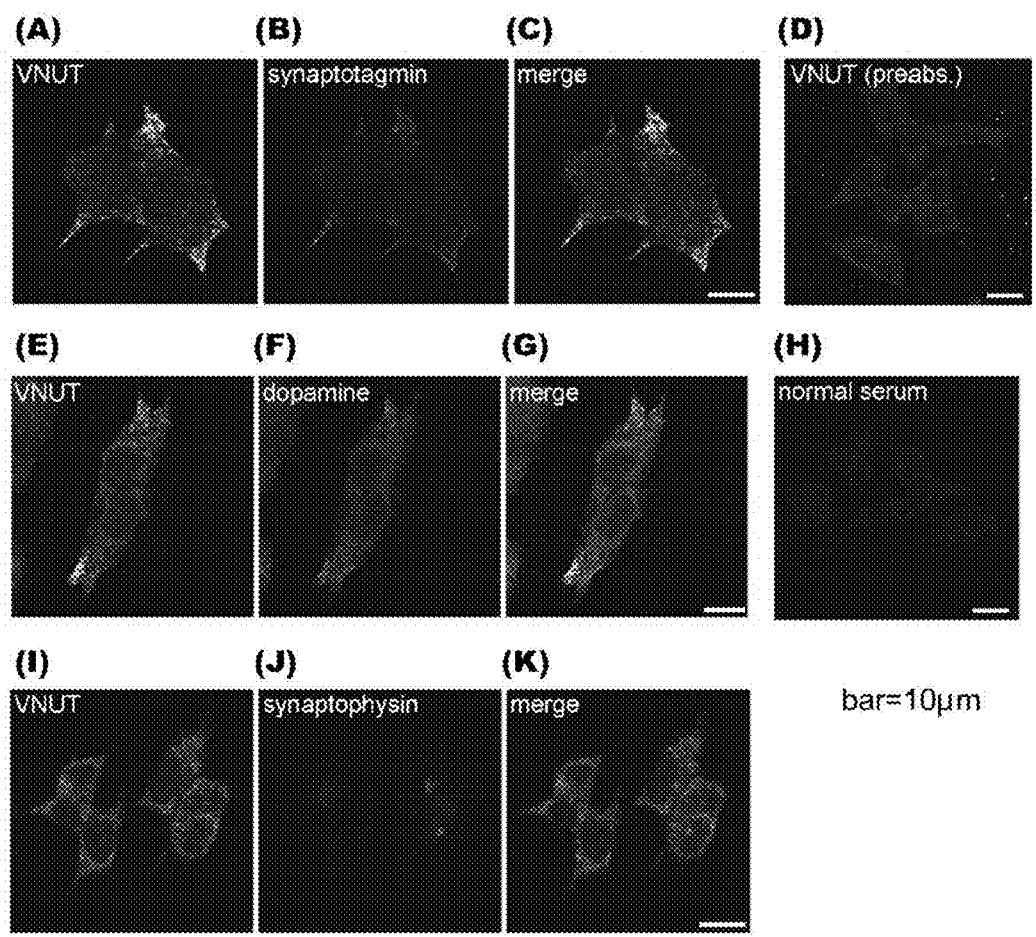
FIG. 18A-18K show the results of performing immunostaining of PC12 cells. The antibodies used are as follows: (A) anti-SLCA19 antibody only, (B) anti-synaptotagmin antibody only, (C) double staining with anti-SLCA19 antibody and anti-synaptotagmin antibody, (D) anti-SLCA19 antibody before absorption only, (E) anti-SLCA19 antibody only, (F) anti-dopamine antibody only, (G) double staining with anti-SLCA19 antibody and anti-dopamine antibody, (H)

An anti-SLCA19 antibody was combined with an anti-synaptotagmin antibody, an anti-dopamine antibody or an anti-synaptophysin antibody, and double immunostaining of PC12 cells was carried out. The results are presented in FIG. 18, which presents photographs showing the results of (A) staining in the presence of the anti-SLCA19 antibody only, (B) staining in the presence of the anti-synaptotagmin antibody only, (C) double staining in the presence of the anti-SLCA19 antibody and anti-synaptotagmin antibody, (D) staining in the presence of the anti-SLCA19 antibody only before absorption, (E) staining in the presence of the anti-SLCA19 antibody only, (F) staining in the presence of the anti-dopamine antibody only, (G) double staining in the presence of the anti-SLCA19 antibody and anti-dopamine antibody, (H) staining in the presence of ordinary serum (preimmune) only, (I) staining in the presence of the anti-SLCA19 antibody only, (J) staining in the presence of the anti-synaptophysin antibody only, and (K) double staining in the presence of the anti-SLCA19 antibody and anti-synaptophysin antibody. The respective combinations of (A) to (C), (E) to (G), and (I) to (K) show the results of fluorescent staining of same cells. The white bar represents 10 μm. From the results of the double immunostaining, it was shown that SLC17A9 co-localized with synaptotagmin, which is a marker of secretory granules. SLC17A9 also co-localized with dopamine.

However, SLC17A9 did not co-localize with synaptophysin, which is a marker of synaptic-like microvesicles. Therefore, it was shown from these results that SLC17A9 localizes in the secretory granules.

Example 18

Knockdown of SLC17A9 by RNAi

Knockdown of SLC17A9 by RNAi was carried out as follows. A sequence for RNAi designed by Qiagen HP OnGuard siRNA Design was used. The nucleic acid sequence of the RNAi used was UAUUCGAGAGAAUGUCACG (SEQ ID NO: 15). This sequence and HiPerFect transfection reagent (Qiagen) were used for transfection of 25 nM AllStars negative control siRNA or 25 nM rat SLC17A9 siRNA, and the resultant was cultured for 3 days, to thereby perform knockdown of SLC17A9. Subsequently, the amount of ATP released under KCl stimulus (for 30 minutes) was quantified according to the method described in the following document (Fabbro A, Skorinsva E, Grandolfo M, Nistri A, Giniatullin R (2004) Quantal release of ATP from clusters of PC12 cells. J Physiol 560: 505-517). The amounts of SCL17A9 mRNA in the knocked-down cells (RNAi) and control cells (control) were measured by real-time PCR, and as shown in FIG. 19(A), the amount of SLC17A9 mRNA was decreased by RNAi. The effect of RNAi on the ATP transport activity was tested, and as shown in FIG. 19(B), the KCl-dependent ATP release was suppressed by SLC17A9 RNAi (<0.01, * <0.001). It was confirmed by this experiment that the expression product of SLC17A9 was responsible for the ATP transport.

Example 19

Purification of Mouse Homologue of SLC17A9, Reconstitution and Transport Activity Measurement (1. Cloning of Mouse SLC17A9 (mSLC19A9) cDNA)

A mouse adrenal gland-derived total RNA (purchased from Clontech) was cloned by a PCR method using primers (5'-caccatgccatcccagcgctcta-3': SEQ ID NO: 16, and 5'-ttagaggtcctcatgagtggggac-3'SEQ ID NO:17). The PCR conditions were such that after 3 minutes at 94° C., a cycle of 30 seconds at 94° C.: 30 seconds at 56° C.: and 2 minutes at 72° C. was repeated 30 times, and then heating was performed for 5 minutes at 72° C. PCR was performed by adding 0.2 mM dNTP mix, 1 µmol of the primers and 1.5 U of Ex Taq (Takara) to 20 ng of the template, at a scale of 50 µL of 1×Ex Buffer.

Subsequently, the fragment obtained by PCR was inserted into an entry vector using a TOPO cloning kit (Invitrogen). Specifically, the reaction was performed using 10 fmol of a TOPO vector (Invitrogen) and 20 fmol of the PCR product in a Salt solution (Invitrogen), at room temperature at a scale of 6 µL. 2 µL of the reaction mixture was used to transform *Escherichia* Mach-1, and thereby a clone was obtained (designated as pENTER/mSLC17A9).

The insert of pENTER/mSLC17A9 was recombined into pDEST10. Specifically, 75 ng of pDEST10 (Invitrogen) and 4 of a clonase buffer (Invitrogen) were added to 150 ng of pENTER/mSLC17A9, and a TE buffer solution was added to a total amount of 44 µl. Furthermore, 1 µl of LR clonase enzyme mix (Invitrogen) was added thereto, and the mixture was allowed to react for 3 hours at 25° C. Subsequently, proteinase K (final concentration 0.2 mg/mL) was added, and the mixture was allowed to react for 10 minutes at 37° C. Then, 2 µL of the reaction mixture was used in the transformation of *E. coli* DH5α. The obtained plasmid was designated as pDEST10/mSLC17A9.

Subsequently, 20 pg of pDEST10/mSLC17A9 was added to 25 µl of DH10Bac competent cells (Invitrogen), and bacmid was recovered by a miniprep method.

(2. Preparation of Virus for Expression of Mouse SLC17A9 (mSLC19A9))

A virus was produced by the following procedure. Onto a 35-mm plate, $9 \times 10^5$ Sf9 cells were inoculated, and the medium was replaced with Grace's Insect Medium (GIBCO) (supplemented with 0.35 mg/mL of sodium hydrogen carbonate). 1 µg of the bacmid produced above and 64 of cellfectin (Invitrogen) were used to perform transfection by a lipofection method. After incubating the cells for 5 hours at 27° C., the cells were cultured for several days until signs of infection could be seen. After the signs of infection were seen, the medium was recovered and centrifuged (500 g, 5 minutes, 4° C.), and then only the supernatant was recovered. The resulting product was designated as P1 virus.

Subsequently, the virus was isolated by the following procedure. Onto a 100-mm plate were inoculated $6 \times 10^6$ Sf9 cells (50% confluent), 1 mL of a virus solution which had been treated by 10-fold serial dilution was added, and the mixture was shaken for one hour at room temperature. The medium in the mixture plate was removed, and then 10 mL of a mixture of complete TMN-FH:4% SeaPlaque Agarose=3:1 was formed into layers. After the agarose was solidified, the system was sealed at 27° C. for 7 to 10 days, and the cells were cultured. Plaques formed thereon were picked up and were reinfected. After 72 hours, this medium was recovered in the same manner as in the case of P1 virus, and the resulting product was designated as P2 virus. This P2 virus was infected into Sf9 cells at about M.O.I.=0.1 to 0.2, and was cultured at 27° C. for 5 days. This medium was recovered, and the resulting product was designated as high-titer virus.

The titer of viruses was measured by the following procedure. Onto a 100-mm plate were inoculated $6.0 \times 10^6$ Sf9 cells (50% confluent), and 1 mL of a virus solution which had been diluted to $10^{-5}$ to $10^{-8}$ by running a 10-fold dilution series, was added to the plate. The cells were infected while shaking in a see-saw action for one hour at room temperature. Three plates were provided for each concentration. Complete TNM-FH and 4% SeaPlaque agarose after autoclave sterilization were incubated in a water bath at 48° C., the same amount was aseptically mixed, and the mixture was incubated again in a water bath. 5 mL of this mixture was mixed with 5 mL of complete TNM-FH at room temperature, and the medium was removed from the petri dish after infection, and was formed into layers. After agarose was hardened, the system was carefully transferred into the incubator at 27° C., sealed and cultured. The plaques formed in about 7 days to 10 days were counted, and the titer per 1 mL of the high-titer virus was calculated.

(Recovery of Virus-infected Cells and Solubilization of Membrane Fraction)

High Five cells were infected at M.O.I.=1, and were cultured at 27° C. The cells after 60 hours of infection were recovered with a cell scraper and centrifuged at 700×g for 10 minutes, and the supernatant was removed. The remnant was suspended in a disruption buffer [20 mM Tris-HCl pH 8.0, 100 mM potassium acetate, 10% glycerol, 5 mM DTT, 1 µg/mL pepstatin A (Dojindo Laboratories, Ltd.), and 1 µg/mL leupeptin (Dojindo Laboratories, Ltd.)], the suspension was centrifuged once again at 700×g for 10 minutes, and the supernatant was removed. The remnant was suspended in the disruption buffer. This suspension was subjected to sonication (Output 4, 30 sec×8 times) with a TOMY ultrasonic disruptor, and then the resultant was centrifuged at 700×g for 10 minutes. The supernatant was recovered and subjected to ultracentrifugation at 100,000×g for one hour. The resulting pellet was designated as membrane fraction.

This pellet was placed in a solubilization buffer [20 mM MOPS-Tris pH 7.0, 2% octyl glucoside (Dojindo Laboratories, Ltd.), 10% glycerol, 1 μg/mL pepstatin A, and 1 μg/mL leupeptin], and the mixture was suspended using a homogenizer. The suspension was subjected to centrifugation operation at 100,000×g for 30 minutes, and the supernatant was designated as a membrane solubilized fraction.

(Purification of mSLC17A9 Protein Using Affinity Column)

QIAGEN Ni-NTA Superflow resin was packed into an Econo column (1 mL; 50% slurry), the column was washed with distilled water, and was equilibrated with a solubilization buffer at pH 8.0. To this column, the solubilized fraction prepared as described above was poured and was allowed to adsorb while stirring at 4° C. for 4 hours. This column was washed with 15 mL of a wash buffer [20 mM MOPS-Tris pH 7.0, 0.1% octyl glucoside, 20% glycerol, 5 mM imidazole, 1 μg/mL pepstatin A, and 1 μg/mL leupeptin], and was eluted with the same liquid containing 60 mM imidazole (Elution buffer). The eluted product was obtained as purified protein.

(Reconstitution)

20 μg of the purified mSLC17A9 protein and 0.5 mg of soybean-derived lipids were mixed, and the mixture was incubated at −80° C. for 5 minutes or longer. This mixture was thawed quickly by holding the tube in the hands, and was diluted 30-fold with a buffer solution containing 20 mM MOPS-Tris (pH 7.0), 0.15M sodium acetate, 2 mM magnesium acetate and 0.5 mM DTT. This dilution was centrifuged at 200,000×g at 4° C. for one hour, the supernatant was discarded, and the precipitate was resuspended in a buffer solution containing 20 mM MOPS-Tris (pH 7.0), 0.15M sodium acetate, 2 mM magnesium acetate and 0.5 mM DTT, to achieve reconstitution.

(Measurement of Nucleotide Transport Activity)

The reconstituted proteoliposomes were incubated in a buffer solution containing 20 mM MOPS-Tris (pH 7.0), 0.15M potassium acetate, 2 mM magnesium acetate and 4 mM potassium chloride at 27° C. for 2 minutes, and valinomycin was added to a final concentration of 2 μM. The mixture was further incubated for 2 minutes. The measurement of activity was initiated by addition of 0.1 mM [α-$^{32}$P] ATP (3.7 GBq/mmol). 130 μL of the reaction liquid was recovered at a predetermined time point, and was centrifuged through a Sephadex G-50 (fine) spin column at 760×g for 2 minutes. The uptake of ATP was measured by measuring radioactivity contained in the reaction liquid that had been passed through the column, using a liquid scintillation counter. Furthermore, in an inhibitor test, an inhibitor at a predetermined concentration was added in the case of incubating the proteoliposomes.

(Results)

Changes in the ATP transport over time caused by reconstituted mSLC17A9 protein were measured by the measurement method described above. The results are presented in FIG. 20. Sampling was carried out at each time point shown in the diagram. Val means valinomycin.

The kinetics of the ATP transport by the reconstituted mSLC17A9 protein is presented in FIG. 21. Filled squares (■) represent the amount of ATP uptake with addition of valinomycin; open circles (○) represent the amount of ATP uptake without addition of valinomycin; and filled circles (●) represent the differences, that is, the ATP concentration-dependency of the membrane potential-dependent transport. Km and Vmax values were calculated using KaleidaGraph, and were found to be 0.23 mM and 23.8 nmol/min/mg of protein, respectively.

Subsequently, a test on the inhibition of ATP transport by the reconstituted mSLC17A9 protein was carried out. Any of ATP, GTP or ADP was added at 2 mM, or any of Evans Blue or DIDS was added at 2 μM, and the uptake of radioactive ATP (for 2 minutes) was measured. The results are presented in FIG. 22. ATP specificity of the transport activity was confirmed. On the other hand, it was demonstrated that both GTP and ADP are recognized, and they compete with ATP.

As discussed above, the present invention was illustrated by way of preferred exemplary embodiments of the present invention, but the present invention is not intended to be comprehended to be limited to these exemplary embodiments. It should be understood that the scope of the present invention is definitely defined only by the claims. It should be understood that a person having ordinary skill in the art can carry out the present invention in a scope equivalent to the descriptions of the present invention and common technical knowledge, based on the descriptions of specific preferred exemplary embodiments of the present invention. It should be understood that all patents, patent applications and documents cited in the present specification are herein incorporated by reference to the same extent as if the disclosures are specifically described in the present specification.

Industrial Applicability

According to the present invention, a transporter responsible in ATP transport and a gene encoding the transporter were isolated. Therefore, according to the present invention, the ATP transport system can be artificially reconstituted. Furthermore, according to the present invention, there is provided a method for the screening of a medicament for treating and/or regulating pain in central nerves, blood coagulation by platelet-derived ATP, or the like, the method employing the transporter of the present invention.

The invention claimed is:

1. A method for screening for modulators of anion transport activity of an anion transport protein, the method comprising:
   (a) providing an artificial membrane comprising a polypeptide having an anion transport activity wherein said polypeptide is encoded by a nucleic acid that comprises a sequence having at least 95% homology with the nucleic acid sequence set forth in SEQ ID NO: 1;
   (b) contacting the artificial membrane with a candidate drug;
   (c) measuring the anion transport activity of the artificial membrane; and
   (d) determining, from the anion transport activity measured in step (c), whether the candidate drug is a modulator of anion transport activity of an anion transport protein;

wherein the anion transport activity is phosphate nucleotide transport activity.

2. The method according to claim 1, wherein the modulator of anion transport activity is determined to be an inhibitor.

3. The method according to claim 1, wherein the modulator of anion transport activity is determined to be an activity promoter.

4. The method according to claim 1, wherein the phosphate nucleotide is a nucleotide selected from the group consisting of ATP, GTP and ADP.

5. The method according to claim 1, wherein the anion transport activity is ATP transport activity.

* * * * *

SEQUENCE LISTING

```
<160> NUMBER OF SEQ ID NOS: 17

<210> SEQ ID NO 1
<211> LENGTH: 1293
<212> TYPE: DNA
<213> ORGANISM: Homo sapiens
<220> FEATURE:
<221> NAME/KEY: CDS
<222> LOCATION: (1)..(1293)
```

-continued

```
<400> SEQUENCE: 1 atg acc ctg aca agc agg cgc cag gac agt cag gag gcc agg ccc gag    48
Met Thr Leu Thr Ser Arg Arg Gln Asp Ser Gln Glu Ala Arg Pro Glu
1               5                   10                  15 tgc cag gca tgg acg ggg acg ctg ctg ctg ggc acg tgc ctt ctg tac    96
Cys Gln Ala Trp Thr Gly Thr Leu Leu Leu Gly Thr Cys Leu Leu Tyr
            20                  25                  30 tgc gcc cgc tcc agc atg ccc atc tgc acc gtc tcc atg agc cag gac   144
Cys Ala Arg Ser Ser Met Pro Ile Cys Thr Val Ser Met Ser Gln Asp
        35                  40                  45 ttc ggc tgg aac aag aag gag gcc ggc atc gtg ctc agc agc ttc ttc   192
Phe Gly Trp Asn Lys Lys Glu Ala Gly Ile Val Leu Ser Ser Phe Phe
    50                  55                  60 tgg ggc tac tgc ctg aca cag gtt gtg ggc ggc cac ctc ggg gat cgg   240
Trp Gly Tyr Cys Leu Thr Gln Val Val Gly Gly His Leu Gly Asp Arg
65                  70                  75                  80 att ggg ggt gag aag gtc atc ctg ctg tca gcc tct gcc tgg ggc tcc   288
Ile Gly Gly Glu Lys Val Ile Leu Leu Ser Ala Ser Ala Trp Gly Ser
                85                  90                  95 atc acg gcc gtc acc cca ctg ctc gcc cac ctg agc agt gcc cac ctg   336
Ile Thr Ala Val Thr Pro Leu Leu Ala His Leu Ser Ser Ala His Leu
            100                 105                 110 gcc ttc atg acc ttc tca cgc atc ctc atg ggc ttg ctc caa ggg gtt   384
Ala Phe Met Thr Phe Ser Arg Ile Leu Met Gly Leu Leu Gln Gly Val
        115                 120                 125 tac ttc cct gcc ctg acc agc ctg ctg tcg cag aag gtg cgg gag agt   432
Tyr Phe Pro Ala Leu Thr Ser Leu Leu Ser Gln Lys Val Arg Glu Ser
    130                 135                 140 gag cga gcc ttc acc tac agc atc gtg ggc gcc ggc tcc cag ttt ggg   480
Glu Arg Ala Phe Thr Tyr Ser Ile Val Gly Ala Gly Ser Gln Phe Gly
145                 150                 155                 160 acg ctg ctg acc ggg gcg gtg ggc tcc ctg ctc ctg gaa tgg tac ggc   528
Thr Leu Leu Thr Gly Ala Val Gly Ser Leu Leu Leu Glu Trp Tyr Gly
                165                 170                 175 tgg cag agc atc ttc tat ttc tcc ggc ggc ctc acc ttg ctt tgg gtg   576
Trp Gln Ser Ile Phe Tyr Phe Ser Gly Gly Leu Thr Leu Leu Trp Val
            180                 185                 190 tgg tac gtg tac agg tac ctg ctg agt gaa aaa gat ctc atc ctg gcc   624
Trp Tyr Val Tyr Arg Tyr Leu Leu Ser Glu Lys Asp Leu Ile Leu Ala
        195                 200                 205 ttg ggt gtc ctg gcc caa agc cgg ccg gtg tcc agg cac agc aga gtc   672
Leu Gly Val Leu Ala Gln Ser Arg Pro Val Ser Arg His Ser Arg Val
    210                 215                 220 ccc tgg aga cgg ctc ttc cgg aag cct gct gtc tgg gca gcc gtc gtc   720
Pro Trp Arg Arg Leu Phe Arg Lys Pro Ala Val Trp Ala Ala Val Val
225                 230                 235                 240 tcc cag ctc tct gca gcc tgc tcc ttc atc ctc ctc tcc tgg ctg        768
Ser Gln Leu Ser Ala Ala Cys Ser Phe Phe Ile Leu Leu Ser Trp Leu
                245                 250                 255 ccc acc ttc ttc gag gag acc ttc ccc gac gcc aag ggc tgg atc ttc   816
Pro Thr Phe Phe Glu Glu Thr Phe Pro Asp Ala Lys Gly Trp Ile Phe
            260                 265                 270 aac gtg gtt cct tgg ttg gtg gcg att ccg gcc agt cta ttc agc ggg   864
Asn Val Val Pro Trp Leu Val Ala Ile Pro Ala Ser Leu Phe Ser Gly
        275                 280                 285 ttt ctc tct gat cat ctc atc aat cag ggt tac aga gcc atc acg gtg   912
Phe Leu Ser Asp His Leu Ile Asn Gln Gly Tyr Arg Ala Ile Thr Val
    290                 295                 300 cgg aag ctc atg cag ggc atg ggc ctt ggc ctc tcc agc gtc ttt gct   960
Arg Lys Leu Met Gln Gly Met Gly Leu Gly Leu Ser Ser Val Phe Ala
```

```
                    305                 310                 315                 320
ctg tgc ctg ggc cac acc tcc agc ttc tgt gag tct gtg gtc ttt gca    1008
Leu Cys Leu Gly His Thr Ser Ser Phe Cys Glu Ser Val Val Phe Ala
                    325                 330                 335 tca gcc tcc atc ggc ctc cag acc ttc aac cac agt ggc att tct gtt    1056
Ser Ala Ser Ile Gly Leu Gln Thr Phe Asn His Ser Gly Ile Ser Val
                    340                 345                 350 aac atc cag gac ttg gcc ccg tcc tgc gcc ggc ttt ctg ttt ggt gtg    1104
Asn Ile Gln Asp Leu Ala Pro Ser Cys Ala Gly Phe Leu Phe Gly Val
                    355                 360                 365 gcc aac aca gcc ggg gcc ttg gca ggt gtc gtg ggt gtg tgt cta ggc    1152
Ala Asn Thr Ala Gly Ala Leu Ala Gly Val Val Gly Val Cys Leu Gly
                    370                 375                 380 ggc tac ttg atg gag acc acg ggc tcc tgg act tgc ctg ttc aac ctt    1200
Gly Tyr Leu Met Glu Thr Thr Gly Ser Trp Thr Cys Leu Phe Asn Leu
385                 390                 395                 400 gtg gcc atc atc agc aac ctg ggg ctg tgc acc ttc ctg gtg ttt gga    1248
Val Ala Ile Ile Ser Asn Leu Gly Leu Cys Thr Phe Leu Val Phe Gly
                    405                 410                 415 cag gct cag agg gtg gac ctg agc tct acc cat gag gac ctc tag        1293
Gln Ala Gln Arg Val Asp Leu Ser Ser Thr His Glu Asp Leu
                    420                 425                 430

<210> SEQ ID NO 2
<211> LENGTH: 430
<212> TYPE: PRT
<213> ORGANISM: Homo sapiens

<400> SEQUENCE: 2

Met Thr Leu Thr Ser Arg Arg Gln Asp Ser Gln Glu Ala Arg Pro Glu
1               5                   10                  15

Cys Gln Ala Trp Thr Gly Thr Leu Leu Gly Thr Cys Leu Leu Tyr
                20                  25                  30

Cys Ala Arg Ser Ser Met Pro Ile Cys Thr Val Ser Met Ser Gln Asp
            35                  40                  45

Phe Gly Trp Asn Lys Lys Glu Ala Gly Ile Val Leu Ser Ser Phe Phe
        50                  55                  60

Trp Gly Tyr Cys Leu Thr Gln Val Val Gly His Leu Gly Asp Arg
65                  70                  75                  80

Ile Gly Gly Glu Lys Val Ile Leu Leu Ser Ala Ser Ala Trp Gly Ser
                85                  90                  95

Ile Thr Ala Val Thr Pro Leu Leu Ala His Leu Ser Ser Ala His Leu
            100                 105                 110

Ala Phe Met Thr Phe Ser Arg Ile Leu Met Gly Leu Leu Gln Gly Val
        115                 120                 125

Tyr Phe Pro Ala Leu Thr Ser Leu Leu Ser Gln Lys Val Arg Glu Ser
    130                 135                 140

Glu Arg Ala Phe Thr Tyr Ser Ile Val Gly Ala Gly Ser Gln Phe Gly
145                 150                 155                 160

Thr Leu Leu Thr Gly Ala Val Gly Ser Leu Leu Leu Glu Trp Tyr Gly
                165                 170                 175

Trp Gln Ser Ile Phe Tyr Phe Ser Gly Gly Leu Thr Leu Leu Trp Val
            180                 185                 190

Trp Tyr Val Tyr Arg Tyr Leu Leu Ser Glu Lys Asp Leu Ile Leu Ala
        195                 200                 205

Leu Gly Val Leu Ala Gln Ser Arg Pro Val Ser Arg His Ser Arg Val
    210                 215                 220
```

Pro Trp Arg Arg Leu Phe Arg Lys Pro Ala Val Trp Ala Val Val
225                 230                 235                 240

Ser Gln Leu Ser Ala Ala Cys Ser Phe Phe Ile Leu Leu Ser Trp Leu
            245                 250                 255

Pro Thr Phe Phe Glu Glu Thr Phe Pro Asp Ala Lys Gly Trp Ile Phe
        260                 265                 270

Asn Val Val Pro Trp Leu Val Ala Ile Pro Ala Ser Leu Phe Ser Gly
    275                 280                 285

Phe Leu Ser Asp His Leu Ile Asn Gln Gly Tyr Arg Ala Ile Thr Val
290                 295                 300

Arg Lys Leu Met Gln Gly Met Gly Leu Gly Leu Ser Ser Val Phe Ala
305                 310                 315                 320

Leu Cys Leu Gly His Thr Ser Ser Phe Cys Glu Ser Val Val Phe Ala
                325                 330                 335

Ser Ala Ser Ile Gly Leu Gln Thr Phe Asn His Ser Gly Ile Ser Val
            340                 345                 350

Asn Ile Gln Asp Leu Ala Pro Ser Cys Ala Gly Phe Leu Phe Gly Val
        355                 360                 365

Ala Asn Thr Ala Gly Ala Leu Ala Gly Val Val Gly Val Cys Leu Gly
    370                 375                 380

Gly Tyr Leu Met Glu Thr Thr Gly Ser Trp Thr Cys Leu Phe Asn Leu
385                 390                 395                 400

Val Ala Ile Ile Ser Asn Leu Gly Leu Cys Thr Phe Leu Val Phe Gly
                405                 410                 415

Gln Ala Gln Arg Val Asp Leu Ser Ser Thr His Glu Asp Leu
            420                 425                 430

<210> SEQ ID NO 3
<211> LENGTH: 30
<212> TYPE: DNA
<213> ORGANISM: Artificial
<220> FEATURE:
<223> OTHER INFORMATION: PRIMER

<400> SEQUENCE: 3
caccatgacc ctgacaagca ggcgccagga                                        30

<210> SEQ ID NO 4
<211> LENGTH: 25
<212> TYPE: DNA
<213> ORGANISM: Artificial
<220> FEATURE:
<223> OTHER INFORMATION: PRIMER

<400> SEQUENCE: 4
ctagaggtcc tcatgggtag agctc                                             25

<210> SEQ ID NO 5
<211> LENGTH: 40
<212> TYPE: PRT
<213> ORGANISM: Homo sapiens

<400> SEQUENCE: 5

Met Thr Leu Thr Ser Arg Arg Gln Asp Ser Gln Glu Ala Arg Pro Glu
1               5                   10                  15

Cys Gln Ala Trp Thr Gly Thr Leu Leu Gly Thr Cys Leu Leu Tyr
            20                  25                  30

Cys Ala Arg Ser Ser Met Pro Ile
        35                  40

```
<210> SEQ ID NO 6
<211> LENGTH: 90
<212> TYPE: PRT
<213> ORGANISM: Mus musculus

<400> SEQUENCE: 6

Met Gln Pro Ile Pro Glu Glu Thr Arg Lys Thr Pro Ser Ala Ala Ala
1               5                   10                  15

Glu Asp Thr Arg Trp Ser Arg Pro Glu Cys Gln Ala Trp Thr Gly Ile
            20                  25                  30

Leu Leu Leu Gly Thr Cys Leu Leu Tyr Cys Ala Arg Val Thr Met Pro
        35                  40                  45

Val Cys Thr Val Ala Met Ser Gln Asp Phe Gly Trp Asn Lys Lys Glu
50                  55                  60

Ala Gly Ile Val Leu Ser Ser Phe Phe Trp Gly Tyr Cys Leu Thr Gln
65                  70                  75                  80

Val Val Gly Gly His Leu Gly Asp Arg Ile
                85                  90

<210> SEQ ID NO 7
<211> LENGTH: 1344
<212> TYPE: DNA
<213> ORGANISM: Mus musculus
<220> FEATURE:
<221> NAME/KEY: CDS
<222> LOCATION: (1)..(1344)

<400> SEQUENCE: 7 atg cca tcc cag cgc tct agc ctg atg cag cca atc cca gag gag acc      48
Met Pro Ser Gln Arg Ser Ser Leu Met Gln Pro Ile Pro Glu Glu Thr
1               5                   10                  15 cgc aag acc cct tct gcg gca gca gag gat aca cgg tgg tcc agg cct      96
Arg Lys Thr Pro Ser Ala Ala Ala Glu Asp Thr Arg Trp Ser Arg Pro
            20                  25                  30 gaa tgc cag gcc tgg aca gga atc ctg ctc ctg ggc acc tgc ctg ctg     144
Glu Cys Gln Ala Trp Thr Gly Ile Leu Leu Leu Gly Thr Cys Leu Leu
        35                  40                  45 tac tgc gcc cga gtc acc atg ccc gtc tgt act gtt gcc atg agc cag     192
Tyr Cys Ala Arg Val Thr Met Pro Val Cys Thr Val Ala Met Ser Gln
50                  55                  60 gac ttt ggc tgg aac aag aag gag gct ggt atc gtg ctc agc agc ttc     240
Asp Phe Gly Trp Asn Lys Lys Glu Ala Gly Ile Val Leu Ser Ser Phe
65                  70                  75                  80 ttc tgg ggc tac tgc ctg act cag gtg gtg ggc ggc cac ctt ggg gat     288
Phe Trp Gly Tyr Cys Leu Thr Gln Val Val Gly Gly His Leu Gly Asp
                85                  90                  95 cgc atc gga gga gag aag gtc atc ttg ctg tca gcc tcc gcc tgg ggc     336
Arg Ile Gly Gly Glu Lys Val Ile Leu Leu Ser Ala Ser Ala Trp Gly
            100                 105                 110 ttc att act gtc acc aca cca ctg ctt gcg cac ctc ggc agc ggc cac     384
Phe Ile Thr Val Thr Thr Pro Leu Leu Ala His Leu Gly Ser Gly His
        115                 120                 125 ctg gcc ttc ctg aca ttc tct cga atc ctc acc ggt ctg ctc caa ggt     432
Leu Ala Phe Leu Thr Phe Ser Arg Ile Leu Thr Gly Leu Leu Gln Gly
130                 135                 140 gtc tac ttt cca gcc ctg acc agt ctg ctg tcc cag aaa gta cag gag     480
Val Tyr Phe Pro Ala Leu Thr Ser Leu Leu Ser Gln Lys Val Gln Glu
145                 150                 155                 160 agc gag aga gcc ttt acc tac agc act gtg ggt gct ggc tcc cag gtc     528
Ser Glu Arg Ala Phe Thr Tyr Ser Thr Val Gly Ala Gly Ser Gln Val
                165                 170                 175
```

```
ggg acc ctg gtg act ggg ggc gta ggc tcc gtg ctc ctg gac cag tgt      576
Gly Thr Leu Val Thr Gly Gly Val Gly Ser Val Leu Leu Asp Gln Cys
        180                 185                 190 ggc tgg cag agt gtc ttc tac ttc tca ggt ggc ctc acc ttg ctc tgg      624
Gly Trp Gln Ser Val Phe Tyr Phe Ser Gly Gly Leu Thr Leu Leu Trp
    195                 200                 205 gcg tac tat gtg tac agg tac ctg ctg aat gag aaa gac ctt gtc ctg      672
Ala Tyr Tyr Val Tyr Arg Tyr Leu Leu Asn Glu Lys Asp Leu Val Leu
210                 215                 220 gcc ctg gga ttc ctt gct caa ggc cta cct gtg acc aag ccc tcc aaa      720
Ala Leu Gly Phe Leu Ala Gln Gly Leu Pro Val Thr Lys Pro Ser Lys
225                 230                 235                 240 gtg ccc tgg aga caa cta ttc cgg aag gcc tct gtc tgg gcg gca atc      768
Val Pro Trp Arg Gln Leu Phe Arg Lys Ala Ser Val Trp Ala Ala Ile
            245                 250                 255 tgc tcc cag ttg tgc tct gct tgc tcc ttc ttc att cta ctc tcc tgg      816
Cys Ser Gln Leu Cys Ser Ala Cys Ser Phe Phe Ile Leu Leu Ser Trp
        260                 265                 270 ctg ccc acc ttc ttc aag gag acc ttc ccc aac tcc aag ggc tgg gtc      864
Leu Pro Thr Phe Phe Lys Glu Thr Phe Pro Asn Ser Lys Gly Trp Val
    275                 280                 285 ttc aat gta gtc ccc tgg atg ctg gca att cct gct agt cta ttc agt      912
Phe Asn Val Val Pro Trp Met Leu Ala Ile Pro Ala Ser Leu Phe Ser
290                 295                 300 ggg ttc atc tcc gac cgc ctt atc agt cag ggt tac aga gtc atc acg      960
Gly Phe Ile Ser Asp Arg Leu Ile Ser Gln Gly Tyr Arg Val Ile Thr
305                 310                 315                 320 gtg cgt aag ttc atg cag gtc atg ggc ctt ggt ctg tca agc att ttt     1008
Val Arg Lys Phe Met Gln Val Met Gly Leu Gly Leu Ser Ser Ile Phe
            325                 330                 335 gcc ctg tgt ctg ggt cat acc aca agc ttc ctc aag gct atg atc ttt     1056
Ala Leu Cys Leu Gly His Thr Thr Ser Phe Leu Lys Ala Met Ile Phe
        340                 345                 350 gca tca gct tcc att ggc ttc cag acc ttc aac cac agt ggt att tca     1104
Ala Ser Ala Ser Ile Gly Phe Gln Thr Phe Asn His Ser Gly Ile Ser
    355                 360                 365 gtc aac att cag gac ctg gcc cca tcc tgt gct ggc ttc ctg ttt ggt     1152
Val Asn Ile Gln Asp Leu Ala Pro Ser Cys Ala Gly Phe Leu Phe Gly
370                 375                 380 gta gcc aac act gca ggg gcc tta gca ggt gtg gta ggc gtg tgt ctg     1200
Val Ala Asn Thr Ala Gly Ala Leu Ala Gly Val Val Gly Val Cys Leu
385                 390                 395                 400 agt ggc tac ctg atc gag acc act ggt tcc tgg acc tgt gtg ttc cac     1248
Ser Gly Tyr Leu Ile Glu Thr Thr Gly Ser Trp Thr Cys Val Phe His
            405                 410                 415 ctg gta gcc atc atc agc aac ctg ggg ctg ggc acc ttc ctg gtg ttc     1296
Leu Val Ala Ile Ile Ser Asn Leu Gly Leu Gly Thr Phe Leu Val Phe
        420                 425                 430 ggg aag gcg cag agg gtg gac ctg gtc ccc act cat gag gac ctc taa     1344
Gly Lys Ala Gln Arg Val Asp Leu Val Pro Thr His Glu Asp Leu
    435                 440                 445

<210> SEQ ID NO 8
<211> LENGTH: 447
<212> TYPE: PRT
<213> ORGANISM: Mus musculus

<400> SEQUENCE: 8

Met Pro Ser Gln Arg Ser Ser Leu Met Gln Pro Ile Pro Glu Glu Thr
1               5                   10                  15
```

```
Arg Lys Thr Pro Ser Ala Ala Ala Glu Asp Thr Arg Trp Ser Arg Pro
         20                  25                  30

Glu Cys Gln Ala Trp Thr Gly Ile Leu Leu Leu Gly Thr Cys Leu Leu
             35                  40                  45

Tyr Cys Ala Arg Val Thr Met Pro Val Cys Thr Val Ala Met Ser Gln
 50                  55                  60

Asp Phe Gly Trp Asn Lys Lys Glu Ala Gly Ile Val Leu Ser Ser Phe
 65                  70                  75                  80

Phe Trp Gly Tyr Cys Leu Thr Gln Val Gly Gly His Leu Gly Asp
                 85                  90                  95

Arg Ile Gly Gly Glu Lys Val Ile Leu Leu Ser Ala Ser Ala Trp Gly
                100                 105                 110

Phe Ile Thr Val Thr Thr Pro Leu Leu Ala His Leu Gly Ser Gly His
             115                 120                 125

Leu Ala Phe Leu Thr Phe Ser Arg Ile Leu Thr Gly Leu Leu Gln Gly
         130                 135                 140

Val Tyr Phe Pro Ala Leu Thr Ser Leu Leu Ser Gln Lys Val Gln Glu
145                 150                 155                 160

Ser Glu Arg Ala Phe Thr Tyr Ser Thr Val Gly Ala Gly Ser Gln Val
                 165                 170                 175

Gly Thr Leu Val Thr Gly Gly Val Gly Ser Val Leu Leu Asp Gln Cys
             180                 185                 190

Gly Trp Gln Ser Val Phe Tyr Phe Ser Gly Gly Leu Thr Leu Leu Trp
         195                 200                 205

Ala Tyr Tyr Val Tyr Arg Tyr Leu Leu Asn Glu Lys Asp Leu Val Leu
     210                 215                 220

Ala Leu Gly Phe Leu Ala Gln Gly Leu Pro Val Thr Lys Pro Ser Lys
225                 230                 235                 240

Val Pro Trp Arg Gln Leu Phe Arg Lys Ala Ser Val Trp Ala Ala Ile
                 245                 250                 255

Cys Ser Gln Leu Cys Ser Ala Cys Ser Phe Phe Ile Leu Leu Ser Trp
             260                 265                 270

Leu Pro Thr Phe Phe Lys Glu Thr Phe Pro Asn Ser Lys Gly Trp Val
         275                 280                 285

Phe Asn Val Val Pro Trp Met Leu Ala Ile Pro Ala Ser Leu Phe Ser
290                 295                 300

Gly Phe Ile Ser Asp Arg Leu Ile Ser Gln Gly Tyr Arg Val Ile Thr
305                 310                 315                 320

Val Arg Lys Phe Met Gln Val Met Gly Leu Gly Leu Ser Ser Ile Phe
                 325                 330                 335

Ala Leu Cys Leu Gly His Thr Thr Ser Phe Leu Lys Ala Met Ile Phe
             340                 345                 350

Ala Ser Ala Ser Ile Gly Phe Gln Thr Phe Asn His Ser Gly Ile Ser
         355                 360                 365

Val Asn Ile Gln Asp Leu Ala Pro Ser Cys Ala Gly Phe Leu Phe Gly
     370                 375                 380

Val Ala Asn Thr Ala Gly Ala Leu Ala Gly Val Val Gly Val Cys Leu
385                 390                 395                 400

Ser Gly Tyr Leu Ile Glu Thr Thr Gly Ser Trp Thr Cys Val Phe His
                 405                 410                 415

Leu Val Ala Ile Ile Ser Asn Leu Gly Leu Gly Thr Phe Leu Val Phe
             420                 425                 430

Gly Lys Ala Gln Arg Val Asp Leu Val Pro Thr His Glu Asp Leu
         435                 440                 445
```

<210> SEQ ID NO 9
<211> LENGTH: 1344
<212> TYPE: DNA
<213> ORGANISM: Rattus norvegicus
<220> FEATURE:
<221> NAME/KEY: CDS
<222> LOCATION: (1)..(1344)

<400> SEQUENCE: 9

| | | | | | | | | | | | | | | | | |
|---|---|---|---|---|---|---|---|---|---|---|---|---|---|---|---|---|
| atg | cca | tcc | cag | cgc | tct | agc | ctg | atg | cag | cca | atc | cca | gag | gag | acc | 48 |
| Met | Pro | Ser | Gln | Arg | Ser | Ser | Leu | Met | Gln | Pro | Ile | Pro | Glu | Glu | Thr | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| cgc | aag | acc | cct | tct | gcg | gca | gca | gag | gac | aaa | cgg | tgg | tcc | agg | cct | 96 |
| Arg | Lys | Thr | Pro | Ser | Ala | Ala | Ala | Glu | Asp | Lys | Arg | Trp | Ser | Arg | Pro | |
| | | 20 | | | | | 25 | | | | | 30 | | | | |

| | | | | | | | | | | | | | | | | |
|---|---|---|---|---|---|---|---|---|---|---|---|---|---|---|---|---|
| gaa | tgc | cag | cta | tgg | acg | ggg | atg | ttg | ctc | ctg | ggc | acc | tgc | ttg | ctg | 144 |
| Glu | Cys | Gln | Leu | Trp | Thr | Gly | Met | Leu | Leu | Leu | Gly | Thr | Cys | Leu | Leu | |
| | | | 35 | | | | | 40 | | | | | 45 | | | |

| | | | | | | | | | | | | | | | | |
|---|---|---|---|---|---|---|---|---|---|---|---|---|---|---|---|---|
| tac | tgc | acg | cgt | gtc | acc | atg | cct | gtc | tgt | acc | gtt | gcc | atg | agc | cag | 192 |
| Tyr | Cys | Thr | Arg | Val | Thr | Met | Pro | Val | Cys | Thr | Val | Ala | Met | Ser | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| gac | ttc | ggc | tgg | aac | aag | aag | gag | gct | ggt | atc | gtg | ctc | agc | agc | ttc | 240 |
| Asp | Phe | Gly | Trp | Asn | Lys | Lys | Glu | Ala | Gly | Ile | Val | Leu | Ser | Ser | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | tgg | ggc | tac | tgc | ctg | act | cag | gtg | gtg | ggc | ggc | cac | ctt | ggg | gat | 288 |
| Phe | Trp | Gly | Tyr | Cys | Leu | Thr | Gln | Val | Val | Gly | Gly | His | Leu | Gly | Asp | |
| | | | | 85 | | | | | 90 | | | | | 95 | | |

| | | | | | | | | | | | | | | | | |
|---|---|---|---|---|---|---|---|---|---|---|---|---|---|---|---|---|
| cgc | att | gga | ggt | gag | aag | gtc | atc | ttg | ctg | tca | gcc | tct | gcc | tgg | ggc | 336 |
| Arg | Ile | Gly | Gly | Glu | Lys | Val | Ile | Leu | Leu | Ser | Ala | Ser | Ala | Trp | Gly | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | atc | act | gtc | acc | aca | cca | ctg | ctt | gcc | cac | ctc | ggc | agc | ggc | cac | 384 |
| Phe | Ile | Thr | Val | Thr | Thr | Pro | Leu | Leu | Ala | His | Leu | Gly | Ser | Gly | His | |
| | | 115 | | | | | 120 | | | | | 125 | | | | |

| | | | | | | | | | | | | | | | | |
|---|---|---|---|---|---|---|---|---|---|---|---|---|---|---|---|---|
| ctg | gcc | ttc | gtg | aca | ttc | tct | cga | ata | ctc | acc | ggt | ctg | ctc | caa | ggt | 432 |
| Leu | Ala | Phe | Val | Thr | Phe | Ser | Arg | Ile | Leu | Thr | Gly | Leu | Leu | Gln | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| gtc | tac | ttt | cca | gcc | ctg | acc | agt | ctg | ctg | tcc | cag | aga | gtg | cag | gag | 480 |
| Val | Tyr | Phe | Pro | Ala | Leu | Thr | Ser | Leu | Leu | Ser | Gln | Arg | Val | Gln | Glu | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agc | gag | aga | tcc | ttt | act | tac | agc | act | gtg | ggt | gct | ggc | tcc | cag | gtc | 528 |
| Ser | Glu | Arg | Ser | Phe | Thr | Tyr | Ser | Thr | Val | Gly | Ala | Gly | Ser | Gln | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| ggg | act | ctg | gtg | act | ggg | ggc | ata | ggg | tct | gtg | ctc | ctg | gac | cgg | tgt | 576 |
| Gly | Thr | Leu | Val | Thr | Gly | Gly | Ile | Gly | Ser | Val | Leu | Leu | Asp | Arg | Cys | |
| | | | 180 | | | | | 185 | | | | | 190 | | | |

| | | | | | | | | | | | | | | | | |
|---|---|---|---|---|---|---|---|---|---|---|---|---|---|---|---|---|
| ggc | tgg | cag | agt | gtc | ttc | tac | ttc | tca | ggc | ggc | ctc | acc | ttg | ctc | tgg | 624 |
| Gly | Trp | Gln | Ser | Val | Phe | Tyr | Phe | Ser | Gly | Gly | Leu | Thr | Leu | Leu | Trp | |
| | | 195 | | | | | 200 | | | | | 205 | | | | |

| | | | | | | | | | | | | | | | | |
|---|---|---|---|---|---|---|---|---|---|---|---|---|---|---|---|---|
| gtg | tac | tac | gtg | tac | aag | tac | ctg | ctg | gat | gag | aaa | gac | ctt | gtc | ctg | 672 |
| Val | Tyr | Tyr | Val | Tyr | Lys | Tyr | Leu | Leu | Asp | Glu | Lys | Asp | Leu | Val | Leu | |
| | 210 | | | | | 215 | | | | | 220 | | | | | |

| | | | | | | | | | | | | | | | | |
|---|---|---|---|---|---|---|---|---|---|---|---|---|---|---|---|---|
| gcc | ctg | ggt | gtc | ctg | gca | caa | ggc | cta | cct | gtg | acc | agg | ccc | tcc | aaa | 720 |
| Ala | Leu | Gly | Val | Leu | Ala | Gln | Gly | Leu | Pro | Val | Thr | Arg | Pro | Ser | Lys | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gtg | ccc | tgg | aga | caa | ctc | ttc | cgg | aag | gcc | tct | gtc | tgg | gcg | gta | atc | 768 |
| Val | Pro | Trp | Arg | Gln | Leu | Phe | Arg | Lys | Ala | Ser | Val | Trp | Ala | Val | Ile | |
| | | | | 245 | | | | | 250 | | | | | 255 | | |

| | | | | | | | | | | | | | | | | |
|---|---|---|---|---|---|---|---|---|---|---|---|---|---|---|---|---|
| tgc | tca | cag | ctg | tcc | tca | gct | tgc | tct | ttc | ttc | att | cta | ctc | tcc | tgg | 816 |
| Cys | Ser | Gln | Leu | Ser | Ser | Ala | Cys | Ser | Phe | Phe | Ile | Leu | Leu | Ser | Trp | |
| | | | 260 | | | | | 265 | | | | | 270 | | | |

```
cta ccc acc ttc ttc aag gag acc ttc ccc cac tcc aag ggc tgg gtc      864
Leu Pro Thr Phe Phe Lys Glu Thr Phe Pro His Ser Lys Gly Trp Val
        275                 280                 285 ttc aat gtg gta ccc tgg ttg ctg gca att cct gcc agt ttg ttc agc      912
Phe Asn Val Val Pro Trp Leu Leu Ala Ile Pro Ala Ser Leu Phe Ser
290                 295                 300 ggg ttc atc tct gac cgc ctc atc agt cag ggt tac aga gtc atc acg      960
Gly Phe Ile Ser Asp Arg Leu Ile Ser Gln Gly Tyr Arg Val Ile Thr
305                 310                 315                 320 gtg cgt aag ttc atg cag gtc atg ggc ctt ggt ctg tca agc att ttt     1008
Val Arg Lys Phe Met Gln Val Met Gly Leu Gly Leu Ser Ser Ile Phe
                325                 330                 335 gcc ctg tgt ctg ggt cac acc aca agc ttc ctc aag tct atg atc ttt     1056
Ala Leu Cys Leu Gly His Thr Thr Ser Phe Leu Lys Ser Met Ile Phe
        340                 345                 350 gcg tca gcg tcc att ggc ttc cag acc ttc aac cac agt ggt att tca     1104
Ala Ser Ala Ser Ile Gly Phe Gln Thr Phe Asn His Ser Gly Ile Ser
355                 360                 365 gtc aac att cag gac ctg gcc cca tcc tgt gct ggt ttc ctg ttt ggt     1152
Val Asn Ile Gln Asp Leu Ala Pro Ser Cys Ala Gly Phe Leu Phe Gly
370                 375                 380 gta gcc aac act gca ggg gcc ttg gca ggt gtg gta ggc gtg tgt cta     1200
Val Ala Asn Thr Ala Gly Ala Leu Ala Gly Val Val Gly Val Cys Leu
385                 390                 395                 400 ggt ggc tat ctg atc gag acc act ggc tcc tgg acc tgt gtg ttc cac     1248
Gly Gly Tyr Leu Ile Glu Thr Thr Gly Ser Trp Thr Cys Val Phe His
                405                 410                 415 ctg gtg gcc atc gtc agc aac ctg gga ctg ggc acc ttt ctg gtg ttt     1296
Leu Val Ala Ile Val Ser Asn Leu Gly Leu Gly Thr Phe Leu Val Phe
        420                 425                 430 ggg aag gca cag agg gtg gac ctg gta ccc act cat gag gac ctc tag     1344
Gly Lys Ala Gln Arg Val Asp Leu Val Pro Thr His Glu Asp Leu
435                 440                 445

<210> SEQ ID NO 10
<211> LENGTH: 447
<212> TYPE: PRT
<213> ORGANISM: Rattus norvegicus

<400> SEQUENCE: 10

Met Pro Ser Gln Arg Ser Ser Leu Met Gln Pro Ile Pro Glu Glu Thr
1               5                   10                  15

Arg Lys Thr Pro Ser Ala Ala Ala Glu Asp Lys Arg Trp Ser Arg Pro
            20                  25                  30

Glu Cys Gln Leu Trp Thr Gly Met Leu Leu Leu Gly Thr Cys Leu Leu
        35                  40                  45

Tyr Cys Thr Arg Val Thr Met Pro Val Cys Thr Val Ala Met Ser Gln
    50                  55                  60

Asp Phe Gly Trp Asn Lys Lys Glu Ala Gly Ile Val Leu Ser Ser Phe
65                  70                  75                  80

Phe Trp Gly Tyr Cys Leu Thr Gln Val Val Gly Gly His Leu Gly Asp
                85                  90                  95

Arg Ile Gly Gly Glu Lys Val Ile Leu Leu Ser Ala Ser Ala Trp Gly
            100                 105                 110

Phe Ile Thr Val Thr Thr Pro Leu Leu Ala His Leu Gly Ser Gly His
        115                 120                 125

Leu Ala Phe Val Thr Phe Ser Arg Ile Leu Thr Gly Leu Leu Gln Gly
    130                 135                 140

Val Tyr Phe Pro Ala Leu Thr Ser Leu Leu Ser Gln Arg Val Gln Glu
```

```
                145                 150                 155                 160
Ser Glu Arg Ser Phe Thr Tyr Ser Thr Val Gly Ala Gly Ser Gln Val
                165                 170                 175

Gly Thr Leu Val Thr Gly Gly Ile Gly Ser Val Leu Leu Asp Arg Cys
                180                 185                 190

Gly Trp Gln Ser Val Phe Tyr Phe Ser Gly Gly Leu Thr Leu Leu Trp
                195                 200                 205

Val Tyr Tyr Val Tyr Lys Tyr Leu Leu Asp Glu Lys Asp Leu Val Leu
    210                 215                 220

Ala Leu Gly Val Leu Ala Gln Gly Leu Pro Val Thr Arg Pro Ser Lys
225                 230                 235                 240

Val Pro Trp Arg Gln Leu Phe Arg Lys Ala Ser Val Trp Ala Val Ile
                245                 250                 255

Cys Ser Gln Leu Ser Ser Ala Cys Ser Phe Ile Leu Leu Ser Trp
                260                 265                 270

Leu Pro Thr Phe Phe Lys Glu Thr Phe Pro His Ser Lys Gly Trp Val
                275                 280                 285

Phe Asn Val Val Pro Trp Leu Leu Ala Ile Pro Ala Ser Leu Phe Ser
    290                 295                 300

Gly Phe Ile Ser Asp Arg Leu Ile Ser Gln Gly Tyr Arg Val Ile Thr
305                 310                 315                 320

Val Arg Lys Phe Met Gln Val Met Gly Leu Gly Leu Ser Ser Ile Phe
                325                 330                 335

Ala Leu Cys Leu Gly His Thr Thr Ser Phe Leu Lys Ser Met Ile Phe
                340                 345                 350

Ala Ser Ala Ser Ile Gly Phe Gln Thr Phe Asn His Ser Gly Ile Ser
                355                 360                 365

Val Asn Ile Gln Asp Leu Ala Pro Ser Cys Ala Gly Phe Leu Phe Gly
    370                 375                 380

Val Ala Asn Thr Ala Gly Ala Leu Ala Gly Val Val Gly Val Cys Leu
385                 390                 395                 400

Gly Gly Tyr Leu Ile Glu Thr Thr Gly Ser Trp Thr Cys Val Phe His
                405                 410                 415

Leu Val Ala Ile Val Ser Asn Leu Gly Leu Gly Thr Phe Leu Val Phe
                420                 425                 430

Gly Lys Ala Gln Arg Val Asp Leu Val Pro Thr His Glu Asp Leu
                435                 440                 445

<210> SEQ ID NO 11
<211> LENGTH: 1362
<212> TYPE: DNA
<213> ORGANISM: Bos taurus
<220> FEATURE:
<221> NAME/KEY: CDS
<222> LOCATION: (1)..(1362)

<400> SEQUENCE: 11 atg cag ccg ccc cca gac gag acc cgc agg gac gcg gcg gag gac acc      48
Met Gln Pro Pro Pro Asp Glu Thr Arg Arg Asp Ala Ala Glu Asp Thr
1               5                   10                  15 cag tgg tcc agg cct gag tgc cag gta tgg aca ggg aca ctg ctg ttg      96
Gln Trp Ser Arg Pro Glu Cys Gln Val Trp Thr Gly Thr Leu Leu Leu
            20                  25                  30 ggc acg tgc ctg ctc tac tgc gcc cgc gtc agc atg cct gtc tgc gcc     144
Gly Thr Cys Leu Leu Tyr Cys Ala Arg Val Ser Met Pro Val Cys Ala
        35                  40                  45 gcc tcc atg agc cag gac ttc ggc tgg aac aag aaa gag gct ggc gtc     192
```

```
                                                     -continued

Ala Ser Met Ser Gln Asp Phe Gly Trp Asn Lys Lys Glu Ala Gly Val
     50              55              60 gtg ctc agc agc ttc ttc tgg ggc tac tgc ctg act cag gtg gtg ggc    240
Val Leu Ser Ser Phe Phe Trp Gly Tyr Cys Leu Thr Gln Val Val Gly
 65              70              75              80 ggc cac ctg ggg gac cgg atc ggc ggc gag aag gtc atc ctg ctc tcg    288
Gly His Leu Gly Asp Arg Ile Gly Gly Glu Lys Val Ile Leu Leu Ser
                 85              90              95 gct tct gcc tgg ggc ttc atc acc gtg gcc act cca ctg ctc gcg cac    336
Ala Ser Ala Trp Gly Phe Ile Thr Val Ala Thr Pro Leu Leu Ala His
            100             105             110 ctt ggc agc gcc cac ctg gcc ttc atg acc ttc tct cgc atc ctc acc    384
Leu Gly Ser Ala His Leu Ala Phe Met Thr Phe Ser Arg Ile Leu Thr
        115             120             125 ggc ttg ctc caa ggg gtt tac ttc cct gca ctg acc agc ctg ctg tcc    432
Gly Leu Leu Gln Gly Val Tyr Phe Pro Ala Leu Thr Ser Leu Leu Ser
    130             135             140 cag aag gtg cgg gag agt gaa cga gcc ttc acc tac agc act gtg ggg    480
Gln Lys Val Arg Glu Ser Glu Arg Ala Phe Thr Tyr Ser Thr Val Gly
145             150             155             160 gcc ggc tcc cag ttc ggg aca ctg gtg acc ggg gct gtg ggc tcc ctg    528
Ala Gly Ser Gln Phe Gly Thr Leu Val Thr Gly Ala Val Gly Ser Leu
                165             170             175 ctc ctg gac tgg tac ggc tgg ccg agt gtc ttc tac ttt tcg ggt gga    576
Leu Leu Asp Trp Tyr Gly Trp Pro Ser Val Phe Tyr Phe Ser Gly Gly
            180             185             190 ctc acc ctg ctg tgg gtg ggt tac gtg tac agg tgt ctc ctg agt gag    624
Leu Thr Leu Leu Trp Val Gly Tyr Val Tyr Arg Cys Leu Leu Ser Glu
        195             200             205 aga ggt cca tcc tcc cac ctg gat ggc ttt cac gtg gac ctg cct ccc    672
Arg Gly Pro Ser Ser His Leu Asp Gly Phe His Val Asp Leu Pro Pro
    210             215             220 cct tca gat ctc atc ctg gcc ctg ggc atc ctg gcg caa ggc ctg ccc    720
Pro Ser Asp Leu Ile Leu Ala Leu Gly Ile Leu Ala Gln Gly Leu Pro
225             230             235             240 gtg tct aga cac acc aag gtg ccc tgg aga cag ctc ttc cga aag cct    768
Val Ser Arg His Thr Lys Val Pro Trp Arg Gln Leu Phe Arg Lys Pro
                245             250             255 tct gtc tgg gca gcc atc atc tcc cag cta tct gcg gcc tgc tcg ttc    816
Ser Val Trp Ala Ala Ile Ile Ser Gln Leu Ser Ala Ala Cys Ser Phe
            260             265             270 ttc atc ctc ctc tcc tgg ctg ccg acc ttc ttt aag gag acc ttc ccc    864
Phe Ile Leu Leu Ser Trp Leu Pro Thr Phe Phe Lys Glu Thr Phe Pro
        275             280             285 agc tcc aag ggc tgg gtc ttc aac gtg gtg ccc tgg ctg gtg gcc att    912
Ser Ser Lys Gly Trp Val Phe Asn Val Val Pro Trp Leu Val Ala Ile
    290             295             300 ccc gcc agt ctg ctc agc ggg ctt ctc tct gat cat ctc atc aat cag    960
Pro Ala Ser Leu Leu Ser Gly Leu Leu Ser Asp His Leu Ile Asn Gln
305             310             315             320 ggt tac agg acc atc acc gtt cgg aag ttc atg cag gtg atg ggc ctc   1008
Gly Tyr Arg Thr Ile Thr Val Arg Lys Phe Met Gln Val Met Gly Leu
                325             330             335 ggc ctg tcc agt gtt ttt gcc ctg tgt ctg ggc cac acg tcg agc ttt   1056
Gly Leu Ser Ser Val Phe Ala Leu Cys Leu Gly His Thr Ser Ser Phe
            340             345             350 tgt aac tcc gtg gtc ttc gcg tca gcc tcc att ggc ctc cag acc ttc   1104
Cys Asn Ser Val Val Phe Ala Ser Ala Ser Ile Gly Leu Gln Thr Phe
        355             360             365 aac cac agt ggc att tcc gtt aat atc cag gat ctg gcc cct tcc tgt   1152
```

```
                 Asn His Ser Gly Ile Ser Val Asn Ile Gln Asp Leu Ala Pro Ser Cys
                     370                 375                 380 gcc ggc ttt ctg ttt ggc gtg gcc aac aca gct ggg gcc ttg gca ggt     1200
Ala Gly Phe Leu Phe Gly Val Ala Asn Thr Ala Gly Ala Leu Ala Gly
385                 390                 395                 400 gta gtg ggc gtg tgc ctg ggc ggc tac ctc att gag acc acg ggc tcc     1248
Val Val Gly Val Cys Leu Gly Gly Tyr Leu Ile Glu Thr Thr Gly Ser
                405                 410                 415 tgg acg tct gtg ttc aac cta gtg gcc gcc atc agc agc ctg ggg ctg     1296
Trp Thr Ser Val Phe Asn Leu Val Ala Ala Ile Ser Ser Leu Gly Leu
                420                 425                 430 tgc acc ttc ctt gtg ttt ggg aag gcc cag cgg gtc gac ctg agc ccc     1344
Cys Thr Phe Leu Val Phe Gly Lys Ala Gln Arg Val Asp Leu Ser Pro
                435                 440                 445 gcc cat gag gac ctc tag                                              1362
Ala His Glu Asp Leu
    450

<210> SEQ ID NO 12
<211> LENGTH: 453
<212> TYPE: PRT
<213> ORGANISM: Bos taurus

<400> SEQUENCE: 12

Met Gln Pro Pro Asp Glu Thr Arg Arg Asp Ala Ala Glu Asp Thr
1               5                   10                  15

Gln Trp Ser Arg Pro Glu Cys Gln Val Trp Thr Gly Thr Leu Leu
                20                  25                  30

Gly Thr Cys Leu Leu Tyr Cys Ala Arg Val Ser Met Pro Val Cys Ala
                35                  40                  45

Ala Ser Met Ser Gln Asp Phe Gly Trp Asn Lys Lys Glu Ala Gly Val
    50                  55                  60

Val Leu Ser Ser Phe Phe Trp Gly Tyr Cys Leu Thr Gln Val Val Gly
65                  70                  75                  80

Gly His Leu Gly Asp Arg Ile Gly Gly Glu Lys Val Ile Leu Leu Ser
                85                  90                  95

Ala Ser Ala Trp Gly Phe Ile Thr Val Ala Thr Pro Leu Leu Ala His
                100                 105                 110

Leu Gly Ser Ala His Leu Ala Phe Met Thr Phe Ser Arg Ile Leu Thr
            115                 120                 125

Gly Leu Leu Gln Gly Val Tyr Phe Pro Ala Leu Thr Ser Leu Leu Ser
        130                 135                 140

Gln Lys Val Arg Glu Ser Glu Arg Ala Phe Thr Tyr Ser Thr Val Gly
145                 150                 155                 160

Ala Gly Ser Gln Phe Gly Thr Leu Val Thr Gly Ala Val Gly Ser Leu
                165                 170                 175

Leu Leu Asp Trp Tyr Gly Trp Pro Ser Val Phe Tyr Phe Ser Gly Gly
                180                 185                 190

Leu Thr Leu Leu Trp Val Gly Tyr Val Tyr Arg Cys Leu Leu Ser Glu
            195                 200                 205

Arg Gly Pro Ser Ser His Leu Asp Gly Phe His Val Asp Leu Pro Pro
    210                 215                 220

Pro Ser Asp Leu Ile Leu Ala Leu Gly Ile Leu Ala Gln Gly Leu Pro
225                 230                 235                 240

Val Ser Arg His Thr Lys Val Pro Trp Arg Gln Leu Phe Arg Lys Pro
                245                 250                 255

Ser Val Trp Ala Ala Ile Ile Ser Gln Leu Ser Ala Ala Cys Ser Phe
```

```
                 260                 265                 270
        Phe Ile Leu Leu Ser Trp Leu Pro Thr Phe Phe Lys Glu Thr Phe Pro
                     275                 280                 285

Ser Ser Lys Gly Trp Val Phe Asn Val Val Pro Trp Leu Val Ala Ile
                     290                 295                 300

Pro Ala Ser Leu Leu Ser Gly Leu Leu Ser Asp His Leu Ile Asn Gln
        305                 310                 315                 320

Gly Tyr Arg Thr Ile Thr Val Arg Lys Phe Met Gln Val Met Gly Leu
                         325                 330                 335

Gly Leu Ser Ser Val Phe Ala Leu Cys Leu Gly His Thr Ser Ser Phe
                         340                 345                 350

Cys Asn Ser Val Val Phe Ala Ser Ala Ser Ile Gly Leu Gln Thr Phe
                         355                 360                 365

Asn His Ser Gly Ile Ser Val Asn Ile Gln Asp Leu Ala Pro Ser Cys
                     370                 375                 380

Ala Gly Phe Leu Phe Gly Val Ala Asn Thr Ala Gly Ala Leu Ala Gly
        385                 390                 395                 400

Val Val Gly Val Cys Leu Gly Gly Tyr Leu Ile Glu Thr Thr Gly Ser
                         405                 410                 415

Trp Thr Ser Val Phe Asn Leu Val Ala Ala Ile Ser Ser Leu Gly Leu
                         420                 425                 430

Cys Thr Phe Leu Val Phe Gly Lys Ala Gln Arg Val Asp Leu Ser Pro
                         435                 440                 445

Ala His Glu Asp Leu
                450

<210> SEQ ID NO 13
<211> LENGTH: 1368
<212> TYPE: DNA
<213> ORGANISM: Canis familiaris
<220> FEATURE:
<221> NAME/KEY: CDS
<222> LOCATION: (1)..(1368)

<400> SEQUENCE: 13 atg agc tgg gga cac gga cct gag gct cag gac cgg tca aag cag gat        48
Met Ser Trp Gly His Gly Pro Glu Ala Gln Asp Arg Ser Lys Gln Asp
1               5                   10                  15 gaa gcc ccg ctg gcc agt ggt gcc gtc gac ggt tcc cca acg gtc atc        96
Glu Ala Pro Leu Ala Ser Gly Ala Val Asp Gly Ser Pro Thr Val Ile
                20                  25                  30 cgc agg gtc gag gtg tct ggg ccc gag tgc cag gtg tgg aca ggg acg       144
Arg Arg Val Glu Val Ser Gly Pro Glu Cys Gln Val Trp Thr Gly Thr
            35                  40                  45 ctg ctg ctg ggc aca tgc ctc ctg tac tgt gcc cgc gtc agc atg ccc       192
Leu Leu Leu Gly Thr Cys Leu Leu Tyr Cys Ala Arg Val Ser Met Pro
        50                  55                  60 gtg tgc acc gtg tcc atg agc cag gac ttc ggc tgg aac aag aag gag       240
Val Cys Thr Val Ser Met Ser Gln Asp Phe Gly Trp Asn Lys Lys Glu
65                  70                  75                  80 gcc ggc atc gtg ctc agc agc ttc ttc tgg ggc tac tgc ctg acc cag       288
Ala Gly Ile Val Leu Ser Ser Phe Phe Trp Gly Tyr Cys Leu Thr Gln
                85                  90                  95 gtg gtg ggc ggc cac ctg ggg gac cgg atc ggg gga gag aag gtc atc       336
Val Val Gly Gly His Leu Gly Asp Arg Ile Gly Gly Glu Lys Val Ile
                100                 105                 110 ctg ctg tcc gcc tcc gcc tgg ggc ttc atc act gcc gcc acc ccg ctg       384
Leu Leu Ser Ala Ser Ala Trp Gly Phe Ile Thr Ala Ala Thr Pro Leu
            115                 120                 125
```

```
ctc gcc cac ctc agc agc gcc cac ctg gtc ttc atg acc ttc tct cgc      432
Leu Ala His Leu Ser Ser Ala His Leu Val Phe Met Thr Phe Ser Arg
    130                 135                 140 atc ctc aca ggc ttg ctc caa ggg gtg tac ttc ccg gcg ctg acc agc      480
Ile Leu Thr Gly Leu Leu Gln Gly Val Tyr Phe Pro Ala Leu Thr Ser
145                 150                 155                 160 ctc ctg tcc cag aag gtg cga gag agc gag cgc gcc ttc acc tac agc      528
Leu Leu Ser Gln Lys Val Arg Glu Ser Glu Arg Ala Phe Thr Tyr Ser
                165                 170                 175 gcc gtg ggg gct ggc tcc cag tgc ggg acg ctg gtg acg ggg gcc gtg      576
Ala Val Gly Ala Gly Ser Gln Cys Gly Thr Leu Val Thr Gly Ala Val
            180                 185                 190 ggc tcc ctg ctc ctg gac tgg tac ggc tgg ccg agc gtc ttc tac ttc      624
Gly Ser Leu Leu Leu Asp Trp Tyr Gly Trp Pro Ser Val Phe Tyr Phe
        195                 200                 205 tcc ggc ggg ctc acc ctg ctg tgg gtg tgt tac gtg tac agg tac ctg      672
Ser Gly Gly Leu Thr Leu Leu Trp Val Cys Tyr Val Tyr Arg Tyr Leu
    210                 215                 220 ctc act gga aaa gag ctc atc ctg gcc ttg ggc gtt ctg gcg caa ggc      720
Leu Thr Gly Lys Glu Leu Ile Leu Ala Leu Gly Val Leu Ala Gln Gly
225                 230                 235                 240 ctg ccg gtg tcc agg cac acc aag gtt ccc tgg aga cag ctc ttc cgg      768
Leu Pro Val Ser Arg His Thr Lys Val Pro Trp Arg Gln Leu Phe Arg
                245                 250                 255 aag cct tcc gtc tgg gca gcc atc tcc tcc cag ctg tcg tcc gcg tgc      816
Lys Pro Ser Val Trp Ala Ala Ile Ser Ser Gln Leu Ser Ser Ala Cys
            260                 265                 270 tcc ttc ttc atc ctc ctc tcc tgg ctg ccc acc ttc ttt cag gag aca      864
Ser Phe Phe Ile Leu Leu Ser Trp Leu Pro Thr Phe Phe Gln Glu Thr
        275                 280                 285 ttc ccc agc tcc aag ggc tgg gtc ttc aac gtg gtg ccc tgg ctg gtg      912
Phe Pro Ser Ser Lys Gly Trp Val Phe Asn Val Val Pro Trp Leu Val
    290                 295                 300 gcc atc ccc gcc agt ctg ttc agc ggg ttc ctc tct gac cat cta atc      960
Ala Ile Pro Ala Ser Leu Phe Ser Gly Phe Leu Ser Asp His Leu Ile
305                 310                 315                 320 aat cag ggt tac agg acc att gct gtg cgg aag ttc atg cag gtg atg     1008
Asn Gln Gly Tyr Arg Thr Ile Ala Val Arg Lys Phe Met Gln Val Met
                325                 330                 335 ggc ctc ggg ctg tcc agc gtt ttt gcc ctg tgc ttg ggc cac acc tcg     1056
Gly Leu Gly Leu Ser Ser Val Phe Ala Leu Cys Leu Gly His Thr Ser
            340                 345                 350 agc ttc tgt aag tcc gtg gtc ttc gcg tcg gcg tcc att ggc ctg cag     1104
Ser Phe Cys Lys Ser Val Val Phe Ala Ser Ala Ser Ile Gly Leu Gln
        355                 360                 365 acc ttc aac cac agt ggc att tcg gtc aac att cag gac ctg gct cca     1152
Thr Phe Asn His Ser Gly Ile Ser Val Asn Ile Gln Asp Leu Ala Pro
    370                 375                 380 tcc tgt gcc ggc ttc ctg ttc ggt gtg gcc aat acc gcc ggg gcc ttg     1200
Ser Cys Ala Gly Phe Leu Phe Gly Val Ala Asn Thr Ala Gly Ala Leu
385                 390                 395                 400 gca ggt gtc gtg ggc gtg tgc ctg ggc ggc tac ctc atc gag acc acg     1248
Ala Gly Val Val Gly Val Cys Leu Gly Gly Tyr Leu Ile Glu Thr Thr
                405                 410                 415 ggc tcc tgg act tcc atg ttc aac ctg gtg gct gcc atc agc ggc ctg     1296
Gly Ser Trp Thr Ser Met Phe Asn Leu Val Ala Ala Ile Ser Gly Leu
            420                 425                 430 ggg ctg tgc acc ttc ctg ctg ttc gga gag gcc cag cgg gtg gac ctg     1344
Gly Leu Cys Thr Phe Leu Leu Phe Gly Glu Ala Gln Arg Val Asp Leu
        435                 440                 445
```

```
agc ccc acc cac gag gac ctc tag                                    1368
Ser Pro Thr His Glu Asp Leu
    450             455
```

<210> SEQ ID NO 14
<211> LENGTH: 455
<212> TYPE: PRT
<213> ORGANISM: Canis familiaris

<400> SEQUENCE: 14

```
Met Ser Trp Gly His Gly Pro Glu Ala Gln Asp Arg Ser Lys Gln Asp
1               5                   10                  15

Glu Ala Pro Leu Ala Ser Gly Ala Val Asp Gly Ser Pro Thr Val Ile
            20                  25                  30

Arg Arg Val Glu Val Ser Gly Pro Glu Cys Gln Val Trp Thr Gly Thr
        35                  40                  45

Leu Leu Leu Gly Thr Cys Leu Leu Tyr Cys Ala Arg Val Ser Met Pro
    50                  55                  60

Val Cys Thr Val Ser Met Ser Gln Asp Phe Gly Trp Asn Lys Lys Glu
65                  70                  75                  80

Ala Gly Ile Val Leu Ser Ser Phe Phe Trp Gly Tyr Cys Leu Thr Gln
                85                  90                  95

Val Val Gly Gly His Leu Gly Asp Arg Ile Gly Gly Glu Lys Val Ile
            100                 105                 110

Leu Leu Ser Ala Ser Ala Trp Gly Phe Ile Thr Ala Ala Thr Pro Leu
        115                 120                 125

Leu Ala His Leu Ser Ser Ala His Leu Val Phe Met Thr Phe Ser Arg
    130                 135                 140

Ile Leu Thr Gly Leu Leu Gln Gly Val Tyr Phe Pro Ala Leu Thr Ser
145                 150                 155                 160

Leu Leu Ser Gln Lys Val Arg Glu Ser Glu Arg Ala Phe Thr Tyr Ser
                165                 170                 175

Ala Val Gly Ala Gly Ser Gln Cys Gly Thr Leu Val Thr Gly Ala Val
            180                 185                 190

Gly Ser Leu Leu Leu Asp Trp Tyr Gly Trp Pro Ser Val Phe Tyr Phe
        195                 200                 205

Ser Gly Gly Leu Thr Leu Leu Trp Val Cys Tyr Val Tyr Arg Tyr Leu
    210                 215                 220

Leu Thr Gly Lys Glu Leu Ile Leu Ala Leu Gly Val Leu Ala Gln Gly
225                 230                 235                 240

Leu Pro Val Ser Arg His Thr Lys Val Pro Trp Arg Gln Leu Phe Arg
                245                 250                 255

Lys Pro Ser Val Trp Ala Ala Ile Ser Ser Gln Leu Ser Ala Cys
            260                 265                 270

Ser Phe Phe Ile Leu Leu Ser Trp Leu Pro Thr Phe Phe Gln Glu Thr
        275                 280                 285

Phe Pro Ser Ser Lys Gly Trp Val Phe Asn Val Val Pro Trp Leu Val
    290                 295                 300

Ala Ile Pro Ala Ser Leu Phe Ser Gly Phe Leu Ser Asp His Leu Ile
305                 310                 315                 320

Asn Gln Gly Tyr Arg Thr Ile Ala Val Arg Lys Phe Met Gln Val Met
                325                 330                 335

Gly Leu Gly Leu Ser Ser Val Phe Ala Leu Cys Leu Gly His Thr Ser
            340                 345                 350

Ser Phe Cys Lys Ser Val Val Phe Ala Ser Ala Ser Ile Gly Leu Gln
```

-continued

```
                    355                 360                 365
Thr Phe Asn His Ser Gly Ile Ser Val Asn Ile Gln Asp Leu Ala Pro
    370                 375                 380
Ser Cys Ala Gly Phe Leu Phe Gly Val Ala Asn Thr Ala Gly Ala Leu
385                 390                 395                 400
Ala Gly Val Val Gly Val Cys Leu Gly Gly Tyr Leu Ile Glu Thr Thr
                405                 410                 415
Gly Ser Trp Thr Ser Met Phe Asn Leu Val Ala Ala Ile Ser Gly Leu
                420                 425                 430
Gly Leu Cys Thr Phe Leu Leu Phe Gly Glu Ala Gln Arg Val Asp Leu
                435                 440                 445
Ser Pro Thr His Glu Asp Leu
    450                 455

<210> SEQ ID NO 15
<211> LENGTH: 19
<212> TYPE: RNA
<213> ORGANISM: Artificial
<220> FEATURE:
<223> OTHER INFORMATION: RNA for knock down

<400> SEQUENCE: 15
uauucgagag aaugucacg                                                 19

<210> SEQ ID NO 16
<211> LENGTH: 23
<212> TYPE: DNA
<213> ORGANISM: Artificial
<220> FEATURE:
<223> OTHER INFORMATION: primer

<400> SEQUENCE: 16
caccatgcca tcccagcgct cta                                            23

<210> SEQ ID NO 17
<211> LENGTH: 24
<212> TYPE: DNA
<213> ORGANISM: Artificial
<220> FEATURE:
<223> OTHER INFORMATION: primer

<400> SEQUENCE: 17
ttagaggtcc tcatgagtgg ggac                                           24
```